United States Patent
Virag et al.

(10) Patent No.: US 10,655,148 B2
(45) Date of Patent: May 19, 2020

(54) COMPOSITIONS AND METHODS FOR HELPER STRAIN-MEDIATED FUNGAL GENOME MODIFICATION

(71) Applicant: DANISCO US INC., Palo Alto, CA (US)

(72) Inventors: Aleksandra Virag, Palo Alto, CA (US); Michael Ward, Palo Alto, CA (US)

(73) Assignee: DANISCO US INC, Palo Alto, CA (US)

(*) Notice: Subject to any disclaimer, the term of this patent is extended or adjusted under 35 U.S.C. 154(b) by 0 days.

(21) Appl. No.: 15/536,892

(22) PCT Filed: Dec. 16, 2015

(86) PCT No.: PCT/US2015/066178
§ 371 (c)(1),
(2) Date: Jun. 16, 2017

(87) PCT Pub. No.: WO2016/100562
PCT Pub. Date: Jun. 23, 2016

(65) Prior Publication Data
US 2017/0362610 A1 Dec. 21, 2017

Related U.S. Application Data

(60) Provisional application No. 62/092,444, filed on Dec. 16, 2014.

(51) Int. Cl.
*C12N 15/90* (2006.01)
*C12N 15/04* (2006.01)

(52) U.S. Cl.
CPC ........... *C12N 15/902* (2013.01); *C12N 15/04* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 5,683,899 A | 11/1997 | Stuart | |
| 6,090,581 A * | 7/2000 | Gavrias | C07K 14/38 435/252.1 |
| 8,697,359 B1 | 4/2014 | Zhang | |

FOREIGN PATENT DOCUMENTS

| | | |
|---|---|---|
| WO | 2008/138835 A1 | 11/2008 |
| WO | 2013/141680 A1 | 9/2013 |

OTHER PUBLICATIONS

P. De Boer et al., Highly efficient gene targeting in Pencillium chrysogenum using the bi-partite approach in deltalig4 or deltaku70 mutants, Fungal Genetics and Biology, Oct. 2010, pp. 839-846, vol. 47 (10).

James E. Dicarlo et al., Genome engineering in *Saccharomyces cerevisiae* using CRISPR-Cas systems, Nucleic Acids Research, 2013, pp. 4336-4343, vol. 41, No. 7.

D. Ebbole et al., A rapid and simple method for isolation of Neurospora crassa homokaryons using microconidia, Fungal Genetics Reports, 1990, vol. 37, Article 7.

(Continued)

*Primary Examiner* — Addison D Ault

(57) ABSTRACT

Compositions and methods are provided employing a helper strain system for promoting genetic alterations in a fungal host cell, e.g., a filamentous fungal host cell.

15 Claims, 10 Drawing Sheets

Specification includes a Sequence Listing.

(56) References Cited

OTHER PUBLICATIONS

Ines Fonfara et al., Phylogeny of Cas9 determines functional exchangeability of dual-RNA and Cas9 among orthologous type II CRISPR-Cas systems, Nucleic Acids Research, 2014, pp. 2577-2590, vol. 42, No. 4.

Zhang Guangtao et al., Gene targeting in a nonhomologous end joining deficient Hypocrea jecorina, Journal of Biotechnology, 2009, pp. 146-151, vol. 139.

Dewei Jiang et al., Molecular tools for functional genomics in filamentous fungi: Recent advances and new strategies, Biotechnology Advances, 2013, pp. 1562-1574, vol. 31.

Akihiro Kato et al., Deletion of a Novel F-Box Protein, MUS-10, in Neurospora crassa Leads to Altered Mitochondrial Morphology, Instability of mtDNA and Senescence, Genetics, Aug. 2010, pp. 1257-1269, vol. 185.

Kiminori Kurashima et al., A uvs-5 Strain Is Deficient for a Mitofusin Gene Homologue, fzo1, Involved in Maintenance of Long Life Span in Neurospora crassa, Eukaryotic Cell, Feb. 2013, pp. 233-243, vol. 12, No. 2.

M. Levy et al., Efficient gene replacement and direct hyphal transformation in Sclerotinia sclerotiorum, Molecular Plant Pathology, 2008, pp. 719-725, vol. 9 (5).

Frank J. Maier et al., Development of a highly efficient gene targeting system for Fusarium graminearum using the disruption of a polyketide synthase gene as a visible marker, FEMS Yeast Research, 2005, pp. 653-662, 5.

Prashant Mali et al., Cas9 as a versatile tool for engineering biology, Nat Methods, Oct. 2013, pp. 957-963, vol. 10, No. 10.

Osamu Mizutani et al., A defect of LigD (human Lig4 homolog) for nonhomologous end joining significantly improves efficiency of gene-targeting in Aspergillus oryzae, Fungal Genetics and Biology, 2008, pp. 878-889, vol. 45.

Marcus Roper et al., Nuclear dynamics in a fungal chimera, PNAS, Aug. 6, 2013, pp. 12875-12880, vol. 110, No. 32.

Tadashi Takahashi et al., Enhanced gene targeting frequency in ku70 and ku80 disruption mutants of Aspergillus sojae and Aspergillus oryzae, Mol. Gen Genomics, 2006, pp. 460-470, vol. 275.

International Search Report—PCT/US2015/066178—dated Apr. 21, 2016.

\* cited by examiner

COMPOSITIONS AND METHODS FOR HELPER STRAIN-MEDIATED FUNGAL GENOME MODIFICATION

CROSS-REFERENCE TO RELATED APPLICATIONS

The present application claims priority to U.S. Provisional Application Ser. No. 62/092,444, filed Dec. 16, 2014, which is hereby incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "20190821 NB40692USPCT SequenceListing.TXT" created on Aug. 21, 2019, and having a size of 101 kilobytes and is filed concurrently with the specification. The sequence listing contained in this ASCII formatted document is part of the specification and is herein incorporated by reference in its entirety.

BACKGROUND

A pre-requisite for applying the helper strain concept for fungal genome modification is the ability to form a heterokaryon by fusing two different cell types: the helper strain (HS) and the target strain (TS). In some fungal cells (e.g., *N. crassa*), this fusion can be accomplished by simply mixing the spores of the HS and TS and allowing them to germinate together on selective medium. In other fungal cells (e.g., *T. reesei*), cell fusion does not occur so readily, and it is necessary to make protoplasts to facilitate fusion. Once the cells from the HS and TS are fused, the shared cytoplasm allows the benefit that the HS provides to be available to the TS. In *N. crassa*, the cells are connected into a syncytium which allows the cytoplasm as well as organelles to migrate between cell compartments (Roper, M. Simonin, A., Hickey, P. C., Leeder, A., and Glass, N. L. 2013. Nuclear dynamics in fungal chimera. Proc. Nat. Acad. Sci. 110 (32), 12875-12880). The beneficial components produced by the HS nuclei are, therefore, freely distributed throughout the mycelium. The compartments of *T. reesei*, on the other hand, are separated by septae that limit the migration of cell components.

Once the benefit from the heterokaryon is utilized, the component strains need to be separated. This is achieved by sporulating the heterokaryon, plating the individual conidiospores, and verifying strains that derived from single uninucleate spores. In *N. crassa* microconidia, containing a single nucleus, can be produced on media containing iodoacetate (Ebbole, D. and Sachs, M. S. 1990. A rapid and simple method for isolation of *Neurospora crassa* homokaryons using microconidia. Fungal Genet. Newslett. 37), while some *T. reesei* strains have predominantly multinucleate conidiospores. In *T. reesei*, if a strain that produces multinucleate conidiospores cannot be substituted with one that produces uninucleate conidiospores, additional rounds of spore-purification need to be performed, lengthening the procedure.

As a result of these and other differences, the helper strain concept has not been incorporated into methods for routine manipulation and strain improvement in *T. reesei*.

Thus, there still remains a need for developing efficient and effective helper strain-mediated genome engineering methods and compositions for many fungal host cells, including *T. reesei*.

BRIEF SUMMARY

Compositions and methods are provided employing a helper strain system for promoting genetic alterations in a fungal host cell, e.g., a filamentous fungal host cell.

Aspects of the disclosure are drawn to compositions and methods for homologous recombination of a donor DNA with a genomic locus in a fungal cell, e.g., a filamentous fungal cell.

Therefore, aspect of the disclosure include methods for homologous recombination of a donor DNA with a genomic locus in a fungal cell, the method comprising: (a) generating a heterokaryon between a helper fungal strain and a target fungal strain, wherein the helper fungal strain comprises an expression construct that silences the non-homologous end joining (NHEJ) mechanism; (b) introducing a donor DNA into the heterokaryon, wherein the donor DNA comprises a region of homology to a genomic locus in the target strain sufficient for homologous recombination at the genomic locus; (c) generating and plating spores from the heterokaryon cells of (b); and (d) identifying cells from the plated spores in which (i) the donor DNA has integrated into the genome by homologous recombination at the genomic locus, and (ii) the expression construct that silences the non-homologous end joining (NHEJ) mechanism is not present.

In certain embodiments, the expression construct silences one or more of: ku80, ku70, rad50, mre11, xrs2, lig4, and xrs. In certain embodiments, the expression construct silences ku80, ku70, or both.

In certain embodiments, the method further comprises introducing a functional Cas/guide RNA complex into the heterokaryon, wherein the Cas/guide RNA complex has a target site within the genomic locus. In certain embodiments, the Cas is a Cas nickase. In some instances, the Cas endonuclease is operably linked to one or more nuclear targeting signal (also referred to as a nuclear localization signal/sequence; NLS). SEQ ID NO:1 and SEQ ID NO:2 provide an example of a filamentous fungal cell optimized Cas9 gene with NLS sequences at the N- and C-termini and the encoded amino acid sequence, respectively. Many different NLSs are known in eukaryotes. They include monopartite, bipartite and tripartite types. Any convenient NLS can be used, the monopartite type being somewhat more convenient with examples including the SV40 NLS (SEQ ID NO:9), a NLS derived from the *T. reesei* blr2 (blue light regulator 2; SEQ ID NO:10) gene, or a combination of both.

In certain embodiments, the donor DNA comprises a polynucleotide sequence of interest, wherein homologous recombination at the genomic locus results in insertion of the polynucleotide sequence of interest in the genomic locus.

In certain embodiments, the Cas endonuclease is a Cas9 endonuclease or variant thereof. In certain embodiments, the Cas9 endonuclease or variant thereof comprises a full length Cas9 or a functional fragment thereof from a species selected from the group consisting of: *Streptococcus* sp., *S. pyogenes*, *S. mutans*, *S. thermophilus*, *Campylobacter* sp., *C. jejuni*, *Neisseria* sp., *N. meningitides*, *Francisella* sp., *F. novicida*, and *Pasteurella* sp., *P. multocida*.

In certain embodiments, introducing the functional Cas/guide RNA complex into the heterokaryon comprises introducing a DNA construct comprising an expression cassette for the Cas endonuclease into the fungal cells.

In certain embodiments, introducing the functional Cas/guide RNA complex into the heterokaryon comprises introducing a DNA construct comprising an expression cassette for the guide RNA into the fungal cells.

In certain embodiments, the introducing step comprises directly introducing the Cas endonuclease into the fungal cells.

In certain embodiments, the introducing step comprises directly introducing the guide RNA into the fungal cells.

In certain embodiments, the fungal cell is a filamentous fungal cell. In certain embodiments, the fungal cell is a Eumycotina or Pezizomycotina fungal cell. In certain embodiments, the fungal cell is selected from the group consisting of *Trichoderma, Penicillium, Aspergillus, Humicola, Chrysosporium, Fusarium, Myceliophthora, Neurospora, Hypocrea*, and *Emericella*. In certain embodiments, the fungal cell is a *Trichoderma* sp. cell. In certain embodiments, the fungal cell is a *Trichoderma* sp., e.g., *Trichoderma reesei*.

In some embodiments, the donor DNA has partially integrated into the genome at the genomic locus of the fungal cell. In some embodiments, the donor DNA has completely integrated into the genome at the genomic locus of the fungal cell.

In certain embodiments, integration of the donor DNA results in a modification of the genomic locus. In specific embodiments, the modification is selected from the group consisting of a deletion of one or more nucleotides, an insertion of one or more nucleotides, insertion of an expression cassette encoding a protein of interest, a substitution of one or more nucleotides, and any combination thereof.

In certain embodiments, the identifying step comprises culturing cells grown from the spores from step (c) under conditions to select for or screen for the integration of the donor DNA at the genomic locus or the modification of the genomic locus.

Aspects of the present disclosure are drawn to recombinant fungal cells produced by the methods described above as well as those for use as parental host cells in performing the methods.

Additional embodiments of the methods and compositions of the present disclosure are shown herein.

BRIEF DESCRIPTION OF THE DRAWINGS

The disclosure can be more fully understood from the following detailed description and the accompanying drawings, which form a part of this application.

Figure 5:
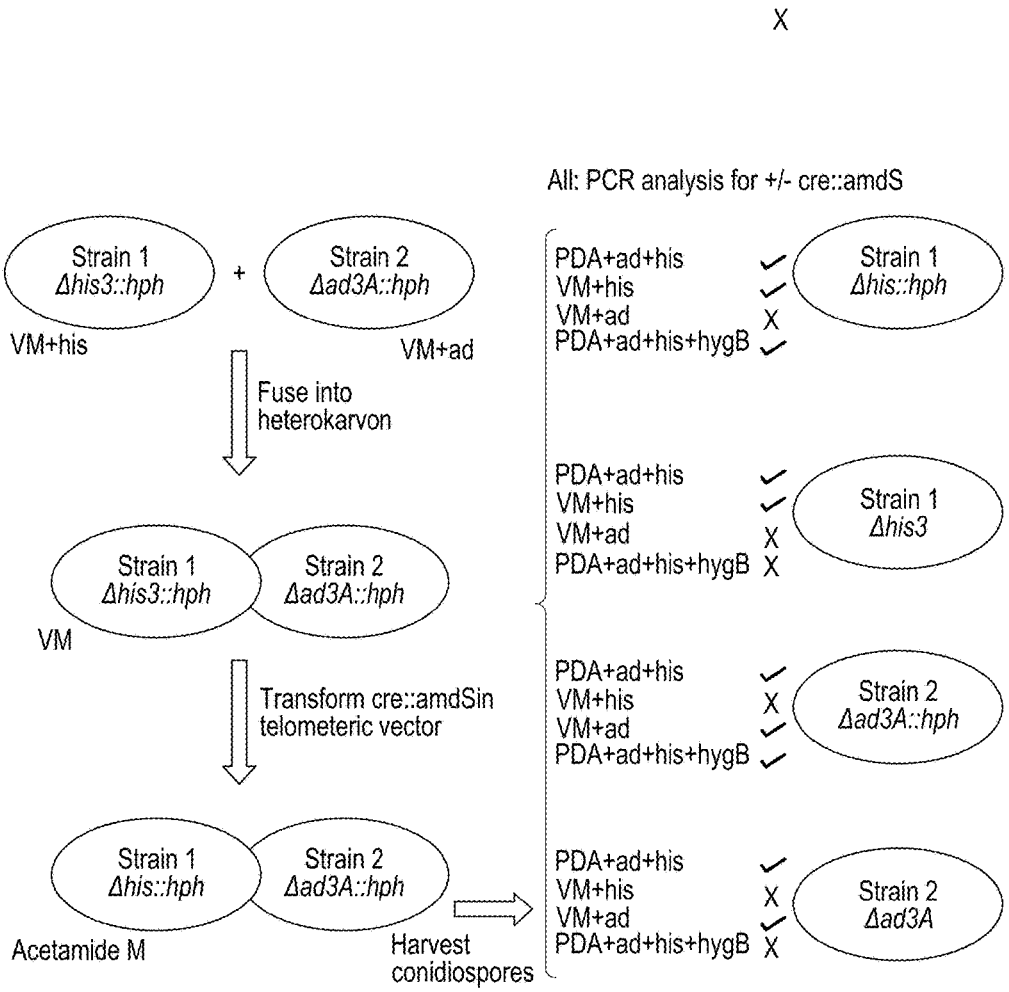
FIG. 5. Heterokaryon transformation where multiple strains are simultaneously transformed with a construct.
Figure 7:
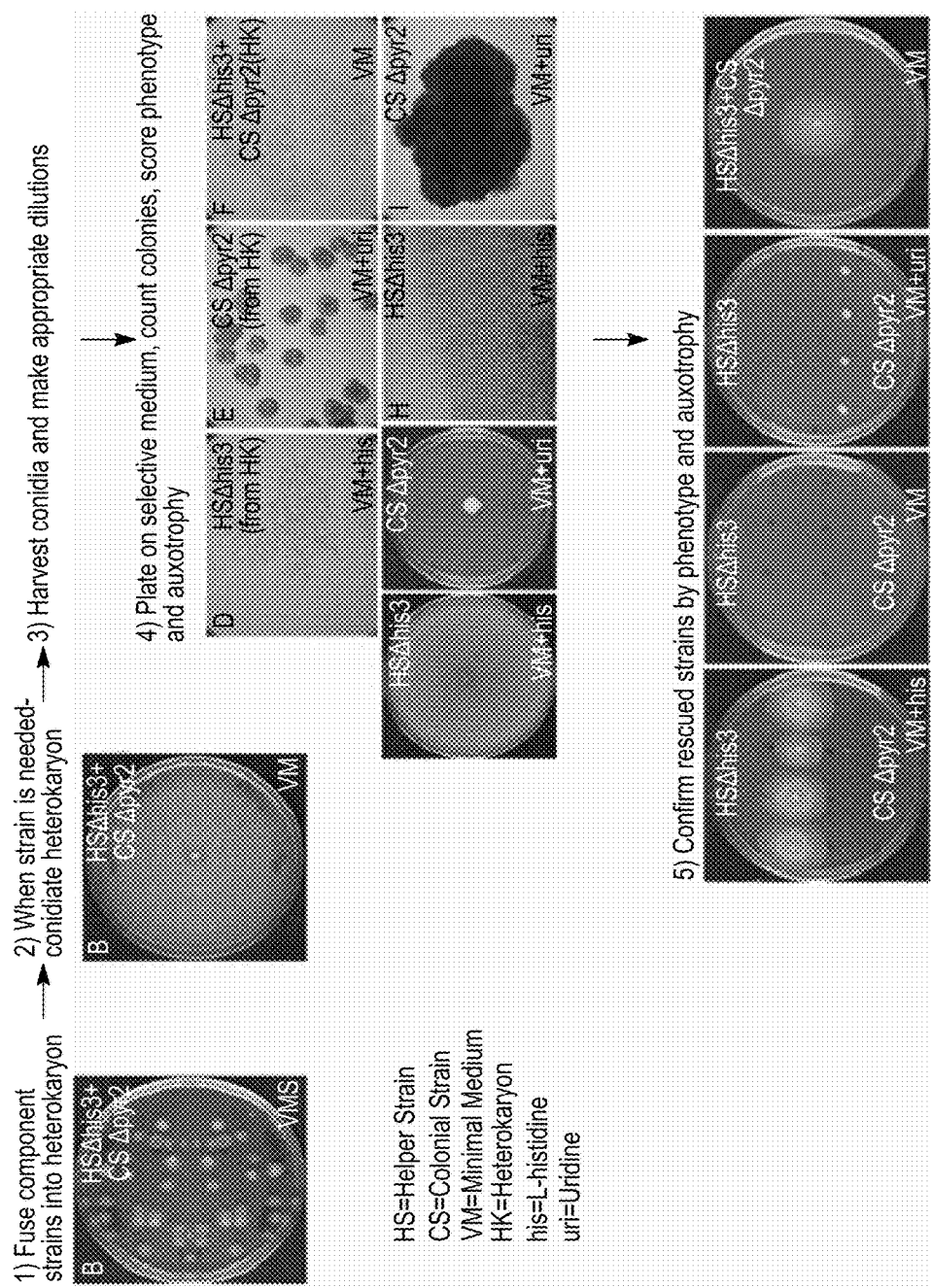
FIG. 7. Use of helper strain for complementing colonial growth and determining allele dominance.

Abbreviations in FIGS. 5 and 7:

his 3=multidomain structural gene encoding histidinol dehydrogenase (EC 1.1.1.23), phosphoribosyl-ATP-pyrophosphohydrolase (EC 3.6.1.31) from *T. reesei*, and phosphoribosyl-AMP cyclohydrolase (EC 3.5.4.19)

hph=gene encoding hygromycin phosphotransferase gene from *E. coli*, ad3A=gene encoding phosphoribosylaminoimidazole-succinocarboxamide synthase (EC 6.3.2.6) from *T. reesei*.

pyr2=orotidine 5'-monophosphate pyrophosphorylase gene

Figure 8:
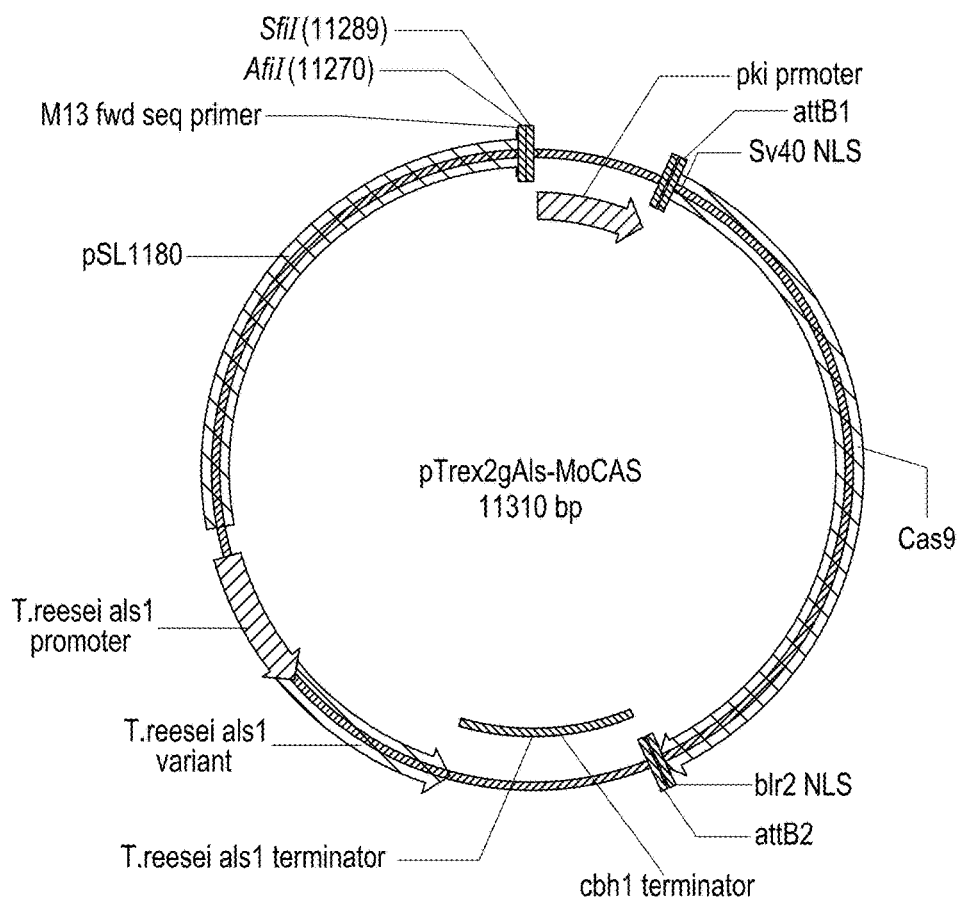

FIG. 8. Illustration of a his3 deletion construct pAVdelta-his3.

DETAILED DESCRIPTION

Compositions and methods are provided employing a helper strain system for promoting genetic alterations in a fungal host cell, e.g., a filamentous fungal host cell.

Before the present compositions and methods are described in greater detail, it is to be understood that the present compositions and methods are not limited to particular embodiments described, and as such may, of course, vary. It is also to be understood that the terminology used herein is for the purpose of describing particular embodiments only, and is not intended to be limiting, since the scope of the present compositions and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless the term is otherwise specifically defined in context. In another example, the phrase "a pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present compositions and methods are not entitled to antedate such publication by virtue of prior invention. Further, the dates of publication provided may be different from the actual publication dates which may need to be independently confirmed.

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

Definitions

The terms "functional fragment", "fragment that is functionally equivalent", "functionally equivalent fragment", and the like, are used interchangeably and refer to a portion or subsequence of a parent polypeptide that retains the qualitative enzymatic activity of the parent polypeptide. It is noted here that a functional fragment may have altered quantitative enzymatic activity as compared to the parent polypeptide.

The terms "functional variant", "variant that is functionally equivalent", "functionally equivalent variant", and the like are used interchangeably and refer to a variant of a parent polypeptide that retains the qualitative enzymatic activity of the parent polypeptide. It is noted here that a functional variant may have altered quantitative enzymatic activity as compared to the parent polypeptide.

Fragments and variants can be obtained via any convenient method, including site-directed mutagenesis and synthetic construction.

The term "genome" as it applies to a fungal cell cells encompasses not only chromosomal DNA found within the nucleus, but organelle DNA found within subcellular components (e.g., mitochondria) of the cell.

A "codon-modified gene" or "codon-preferred gene" or "codon-optimized gene" is a gene having its frequency of codon usage designed to mimic the frequency of preferred codon usage of the host cell. The nucleic acid changes made to codon-optimize a gene are "synonymous", meaning that they do not alter the amino acid sequence of the encoded polypeptide of the parent gene. However, both native and variant genes can be codon-optimized for a particular host cell, and as such no limitation in this regard is intended.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. As is well-known in the art, promoters can be categorized according to their strength and/or the conditions under which they are active, e.g., constitutive promoters, strong promoters, weak promoters, inducible/repressible promoters, tissue-specific/developmentally regulated promoters, cell-cycle dependent promoters, etc.

"RNA transcript" refers to the product resulting from RNA polymerase-catalyzed transcription of a DNA sequence. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. "Sense" RNA refers to RNA transcript that includes the mRNA and can be translated into protein within a cell or in vitro. "Antisense RNA" refers to an RNA transcript that is complementary to all or part of a target primary transcript or mRNA, and that, under certain conditions, blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated into a polypeptide but yet has an effect on cellular processes. The terms "complement" and "reverse complement" are used interchangeably herein with respect to mRNA transcripts, and are meant to define the antisense RNA of the message.

As used herein, "functionally attached" or "operably linked" means that a regulatory region or functional domain of a polypeptide or polynucleotide sequence having a known or desired activity, such as a promoter, enhancer region, terminator, signal sequence, epitope tag, etc., is attached to or linked to a target (e.g., a gene or polypeptide) in such a manner as to allow the regulatory region or functional domain to control the expression, secretion or function of that target according to its known or desired activity. For example, a promoter is operably linked with a coding sequence when it is capable of regulating the expression of that coding sequence (i.e., the coding sequence is under the transcriptional control of the promoter).

The term "recombinant," when used in reference to a biological component or composition (e.g., a cell, nucleic acid, polypeptide/enzyme, vector, etc.) indicates that the biological component or composition is in a state that is not found in nature. In other words, the biological component or composition has been modified by human intervention from its natural state. For example, a recombinant cell encompass a cell that expresses one or more genes that are not found in its native parent (i.e., non-recombinant) cell, a cell that expresses one or more native genes in an amount that is different than its native parent cell, and/or a cell that expresses one or more native genes under different conditions than its native parent cell. Recombinant nucleic acids may differ from a native sequence by one or more nucleotides, be operably linked to heterologous sequences (e.g., a heterologous promoter, a sequence encoding a non-native or variant signal sequence, etc.), be devoid of intronic sequences, and/or be in an isolated form. Recombinant polypeptides/enzymes may differ from a native sequence by one or more amino acids, may be fused with heterologous sequences, may be truncated or have internal deletions of amino acids, may be expressed in a manner not found in a native cell (e.g., from a recombinant cell that over-expresses the polypeptide due to the presence in the cell of an expression vector encoding the polypeptide), and/or be in an isolated form. It is emphasized that in some embodiments, a recombinant polynucleotide or polypeptide/enzyme has a sequence that is identical to its wild-type counterpart but is in a non-native form (e.g., in an isolated or enriched form).

The terms "plasmid", "vector" and "cassette" refer to an extra chromosomal element that carries a polynucleotide sequence of interest, e.g., a gene of interest to be expressed in a cell (an "expression vector" or "expression cassette"). Such elements are generally in the form of double-stranded DNA and may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. The polynucleotide sequence of interest may be a gene encoding a polypeptide or functional RNA that is to be expressed in the target cell. Expression cassettes/vectors generally contain a gene with operably linked elements that allow for expression of that gene in a host cell.

As used herein, a polypeptide referred to as a "Cas endonuclease" or having "Cas endonuclease activity" relates to a CRISPR associated (Cas) polypeptide encoded by a Cas gene where the Cas protein is capable of cutting a target DNA sequence when functionally coupled with one or more guide polynucleotides (see, e.g., U.S. Pat. No. 8,697,359 entitled "CRISPR-Cas systems and methods for altering expression of gene products"). Variants of Cas endonucleases that retain guide polynucleotide directed endonuclease activity are also included in this definition, including Cas variants that have nicking endonuclease activity, i.e., they introduce single strand nick at a double-stranded DNA target site (see definition below). (It is noted that wild-type Cas endonucleases identified to date introduce double-strand breaks at the target site.) A Cas endonuclease is guided by the guide polynucleotide to recognize and cleave a specific target site in double stranded DNA, e.g., at a target site in the genome of a cell. Several different types of CRISPR-Cas systems have been described and can be classified as Type I, Type II, and Type III CRISPR-Cas systems (see, e.g., the description in Liu and Fan, CRISPR-Cas system: a powerful tool for genome editing. Plant Mol Biol (2014) 85:209-218). In certain aspects, the CRISPR-Cas system is a Type II CRISPR-Cas system employing a Cas9 endonuclease or variant thereof (including, e.g., a Cas nickase). The Cas9 endonuclease may be any convenient Cas9 endonuclease, including but not limited to Cas9 endonucleases, and functional fragments thereof, from the following bacterial species: *Streptococcus* sp. (e.g., *S. pyogenes*, *S. mutans*, and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*). Numerous other species of Cas9 can be used. For example, functional Cas9 endonucleases or variants thereof containing an amino acid sequence that has at least 70% identity to any one of SEQ ID NOs:2, 8, and 11-16 may be employed, e.g., at least 80% identity, at least 90% identity, at least 95% identity, at least 96% identity, at least 97% identity, at least 98% identity, at least 99% identity, and including up to 100% identity to any one of SEQ ID NOs: 2, 8, and 11-16. In other embodiments, the Cas endonuclease or variant thereof is a Cpf1 endonuclease of the Type II CRISPR-Cas system. Cpf1 mediates robust DNA interference with features distinct from Cas9. Cpf1 lacks tracrRNA and utilizes a T-rich protospacer-adjacent motif. It cleaves DNA via a staggered DNA double-stranded break. See, e.g., Zetsche et al., Cell (2015) 163:759-771.

As used herein, a "Cas nickase" is a Cas endonuclease that, when functionally coupled with one or more guide polynucleotides, is capable of introducing a single-strand nick into a target double stranded DNA sequence. Cas nickases can be generated recombinantly by inactivating one of the two nuclease domains in a parent Cas endonuclease (e.g., by site-directed mutagenesis). One non-limiting example of a Cas nickase is the Cas9 nickase described in Sander and Joung (Nature Biotechnology, 2013, 1-9) in which the RuvC domain is inactivated by a D10A mutation. As mentioned above, the general term "Cas endonuclease" encompasses both double-strand cutting and nicking Cas polypeptides. For example, if a guide RNA is described as being capable of directing a Cas endonuclease to a desired target site, it would do so for both a double-strand cutting Cas endonuclease and a nicking Cas polypeptide (as defined below).

As used herein, the term "guide polynucleotide" relates to a polynucleotide sequence that can form a complex with a Cas endonuclease and enables the Cas endonuclease to recognize and cleave a DNA target site. The guide polynucleotide can be a single molecule or a double molecule. The guide polynucleotide sequence can be a RNA sequence, a DNA sequence, or a combination thereof (a RNA-DNA combination sequence). A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA (also called the "protospacer" or "target site" below) and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. In one embodiment, the size of the fragment of the crRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides). In certain embodiments, the RNA that guides the RNA/Cas9 endonuclease complex is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a crRNA or crRNA fragment and a tracrRNA or tracrRNA fragment of the type II CRISPR/Cas system that can form a complex with a type II Cas endonuclease, wherein the guide RNA/Cas endonuclease complex can direct the Cas endonuclease to a fungal cell genomic target site, enabling the Cas endonuclease to introduce a double strand break into the genomic target site.

One aspect of using a single guide polynucleotide versus a duplex guide polynucleotide is that only one expression cassette needs to be made to express the single guide polynucleotide in a target cell.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence is at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or is 100% complementary. The VT domain can be at least 12, 13, 14, 15, 16, 17, 18, 19, 20, 21, 22, 23, 24, 25, 26, 27, 28, 29 or 30 nucleotides in length. In some embodiments, the VT domain comprises a contiguous stretch of 12 to 30 nucleotides. The VT domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

As used herein, the tem "guide polynucleotide/Cas endonuclease system" (and equivalents) includes a complex of a Cas endonuclease and a guide polynucleotide (single or double) that is capable of introducing a double strand break at a DNA target site. The Cas endonuclease unwinds the DNA duplex in close proximity of the DNA target site and cleaves both DNA strands upon recognition of a target sequence by a guide RNA, but only if the correct protospacer-adjacent motif (PAM) is appropriately oriented at the 3' end of the target sequence.

The term "expression", as used herein, refers to the production of a functional end-product (e.g., an mRNA, guide RNA, or a protein) in either precursor or mature form.

"Introduced" in the context of inserting a polynucleotide or polypeptide into a cell (e.g., a recombinant DNA construct/expression construct) refers to any method for performing such a task, and includes any means of "transfection", "transformation", "transduction", physical means, or the like, to achieve introduction of the desired biomolecule.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance (sometimes referred to herein as "unstable transformation"). Host organisms containing the transformed nucleic acid fragments are referred to as "transgenic" organisms.

"Fungal cell", "fungi", "fungal host cell", and the like, as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., supra) and all mitosporic fungi (Hawksworth et al., supra). In certain embodiments, the fungal host cell is a yeast cell, where by "yeast" is meant ascosporogenous yeast (Endomycetales), basidiosporogenous yeast, and yeast belonging to the Fungi Imperfecti (Blastomycetes). As such, a yeast host cell includes a *Candida, Hansenula, Kluyveromyces, Pichia, Saccharomyces, Schizosaccharomyces*, or *Yarrowia* cell. Species of yeast include, but are not limited to, the following: *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis*, and *Yarrowia lipolytica* cell.

The term "filamentous fungal cell" includes all filamentous forms of the subdivision Eumycotina. Suitable cells of filamentous fungal genera include, but are not limited to, cells of *Acremonium, Aspergillus, Aureobasidium, Bjerkandera, Ceriporiopsis, Chrysosporium, Coprinus, Coriolus, Corynascus, Chaertomium, Cryptococcus, Filobasidium, Fusarium, Gibberella, Humicola, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes*, and *Trichoderma*. Filamentous fungal species include, but are not limited to, cells of *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei*, and *Trichoderma viride*.

When used in the context of a Cas/guide polynucleotide system, the terms "target site", "target sequence", "genomic target site", "genomic target sequence" (and equivalents) are used interchangeably herein and refer to a polynucleotide sequence in the genome of a fungal cell at which a Cas endonuclease cleavage is desired. The context in which this term is used, however, can slightly alter its meaning. For example, the target site for a Cas endonuclease is generally very specific and can often be defined to the exact nucleotide sequence/position, whereas in some cases the target site for a desired genome modification can be defined more broadly than merely the site at which DNA cleavage occurs, e.g., a genomic locus or region where homologous recombination is desired. Thus, in certain cases, the genome modification that occurs via the activity of Cas/guide RNA DNA cleavage is described as occurring "at or near" the target site. The target site can be an endogenous site in the fungal cell genome, or alternatively, the target site can be heterologous to the fungal cell and thereby not be naturally occurring in the genome, or the target site can be found in a heterologous genomic location compared to where it occurs in nature.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The term "derived from" encompasses the terms "originated from," "obtained from," "obtainable from," "isolated from," and "created from," and generally indicates that one specified material find its origin in another specified material or has features that can be described with reference to the another specified material.

As used herein, the term "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm–5° C. (5° C. below the Tm of the probe); "high stringency" at about 5-10° C. below the Tm; "intermediate stringency" at about 10-20° C. below the Tm of the probe; and "low stringency" at about 20-25° C. below the Tm. Alternatively, or in addition, hybridization conditions can be based upon the salt or ionic strength conditions of hybridization, and/or upon one or more stringency washes, e.g.: 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used).

As used herein, the term "hybridization" refers to the process by which a strand of nucleic acid joins with a complementary strand through base pairing, as known in the art. More specifically, "hybridization" refers to the process by which one strand of nucleic acid forms a duplex with, i.e., base pairs with, a complementary strand, as occurs during blot hybridization techniques and PCR techniques. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm–5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while intermediate or low stringency hybridization can be used to identify or detect polynucleotide sequence homologs.

Intermediate and high stringency hybridization conditions are well known in the art. For example, intermediate stringency hybridizations may be carried out with an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/mL denatured sheared salmon sperm DNA, followed by washing the filters in 1×SSC at about 37-50° C. High stringency hybridization conditions may be hybridization at 65° C. and 0.1×SSC (where 1×SSC=0.15 M NaCl, 0.015 M Na citrate, pH 7.0). Alternatively, high stringency hybridization conditions can be carried out at about 42° C. in 50% formamide, 5×SSC, 5×Denhardt's solution, 0.5% SDS and 100 μg/mL denatured carrier DNA followed by washing two times in 2×SSC and 0.5% SDS at room temperature and two additional times in 0.1×SSC and 0.5% SDS at 42° C. And very high stringent hybridization conditions may be hybridization at 68° C. and 0.1×SSC. Those of skill in the art know how to adjust the temperature, ionic strength, etc. as necessary to accommodate factors such as probe length and the like.

The phrase "substantially similar" or "substantially identical," in the context of at least two nucleic acids or polypeptides, means that a polynucleotide or polypeptide comprises a sequence that has at least 90%, at least 91%, at least 92%, at least 93%, at least 94%, at least 95%, at least 96%, at least 97%, at least 98%, or even at least 99% identical to a parent or reference sequence, or does not include amino acid substitutions, insertions, deletions, or modifications made only to circumvent the present description without adding functionality.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) CABIOS 5:151-153; Higgins et al., (1992) Comput Appl Biosci 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) CABIOS 5:151-153; Higgins et al., (1992) Comput Appl Biosci 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" includes a nucleic acid fragment that encodes and is capable to express a functional molecule such as, but not limited to, a specific polypeptide (e.g., an enzyme) or a functional RNA molecule (e.g., a guide RNA, an anti-sense RNA, ribozyme, etc.), and includes regulatory sequences preceding (5' non-coding sequences) and/or following (3' non-coding sequences) the coding sequence. "Native gene" refers to a gene as found in nature with its own regulatory sequences. A recombinant gene refers to a gene that is regulated by a different gene's regulatory sequences which could be from a different organism or the same organism.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated fungal cell is a fungal cell comprising a mutated gene.

As used herein, a "targeted mutation" is a mutation in a native gene that was made by altering a target sequence within the native gene using a method involving a double-strand-break-inducing agent that is capable of inducing a double-strand break in the DNA of the target sequence as disclosed herein or known in the art.

The term "donor DNA" or "donor nucleic acid sequence" or "donor polynucleotide" refers to a polynucleotide that contains a polynucleotide sequence of interest that is to be inserted into a target cell genome. As such, the polynucleotide sequence of interest in the donor DNA may include a novel region to be inserted at or near a target site and/or a modified polynucleotide sequence when compared to the nucleotide sequence to be replaced/edited at or near a target site. In certain embodiments, the donor DNA construct further comprises a first and a second region of homology that flank the polynucleotide sequence of interest. The first and second regions of homology of the donor DNA share homology to a first and a second genomic region, respectively, present in the fungal cell genome. By "homology" is meant DNA sequences that are similar. For example, a "region of homology to a genomic region" that is found on the donor DNA is a region of DNA that has a similar sequence to a given "genomic region" in the fungal cell genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) Molecular Cloning: A Laboratory Manual, (Cold Spring Harbor Laboratory Press, NY); Current Protocols in Molecular Biology, Ausubel et al., Eds (1994) Current Protocols, (Greene Publishing Associates, Inc. and John Wiley & Sons, Inc); and, Tijssen (1993) Laboratory Techniques in Biochemistry and Molecular Biology—Hybridization with Nucleic Acid Probes, (Elsevier, New York).

As used herein, a "genomic region" is a segment of a chromosome in the genome of a fungal cell (e.g., a target cell). The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology. A genomic region can include the regions that surround a Cas/guide RNA target site in the genome.

As used herein, "homologous recombination" includes the exchange of DNA fragments between two DNA molecules at the sites of homology and is well described in the art.

A phenotypic marker is a screenable or selectable marker that includes visual markers and selectable markers whether it is a positive or negative selectable marker. Any phenotypic marker can be used. Specifically, a selectable or screenable marker comprises a DNA segment that allows one to identify, select for, or screen for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds and antibiotics, such as, chlorimuron ethyl, benomyl, Basta, and hygromycin phosphotransferase (HPT); DNA segments that encode products which are otherwise lacking in the recipient cell (e.g., tRNA genes, auxotrophic markers, dominant heterologous marker-amdS); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Methods and Compositions for Modifying a Fungal Cell Genome

As summarized above, the present disclosure provides compositions and methods for employing a helper strain system for promoting genetic alterations in a fungal host cell, e.g., a filamentous fungal host cell.

Before describing the aspects of the present disclosure, it is important to note that a multitude of cellular processes are executed or controlled in different ways between different fungal cell species, e.g., between *T. reesei* and *N. crassa*, e.g., the molecular processes that regulate senescence. In *N. crassa*, introduction of mutations into mus-10, an F-box protein that is a part of the ubiquitin ligase complex (Kato, et al., 2010, Genetics 185, 1257-1269), or fzo-1, a mitofuzin (Kurashima, et al., 2013, Eukaryot. Cell 12 (2), 233-243), cause senescence ending in cell death. When equivalent mutations are introduced into *T. reesei* mus-10 and fzo-1 homologues, cell death is not observed. As such, processes demonstrated in one species (e.g., *N. crassa*) cannot automatically be extrapolated to all others (e.g., *T. reesei*).

*T. reesei* has two main modes by which it incorporates DNA fragments into its genome: homologous integration and ectopic integration. The non-homologous end-joining (NHEJ) machinery is important for ectopic integration, and if a component of this machinery is deleted, the rate of homologous integration increases significantly (Guangtao, et al., 2009, J. Biotechnol. 139, 146-151).

Figure 1:
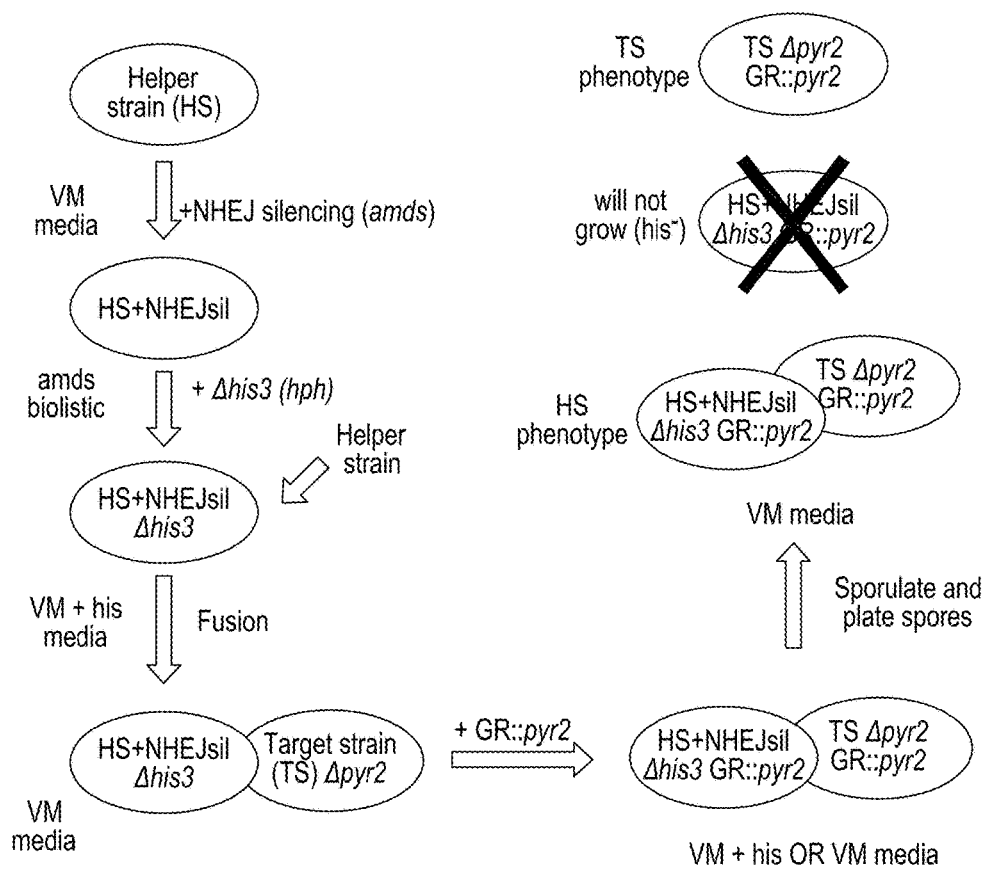
FIG. 1. Schematic presentation of the strategy to use a helper strain with silenced NHEJ to improve homologous integration of targeted DNA cassettes. NHEJsil=Non-Homologous End Joining silencing cassette, GR=Gene Replacement sequence, amdS=gene encoding acetamidase from *Aspergillus nidulans*, his 3=multidomain structural gene encoding histidinol dehydrogenase (EC 1.1.1.23), phosphoribosyl-ATP-pyrophosphohydrolase (EC 3.6.1.31) from *T. reesei*, and phosphoribosyl-AMP cyclohydrolase (EC 3.5.4.19), hph=gene encoding hygromycin phosphotransferase gene from *E. coli*, pyr2=gene encoding orotidine 5'-monophosphate pyrophosphorylase.

Therefore, an alternative way to increase homologous recombination of DNA fragments in a target strain is to use a helper strain in which one or more NHEJ components are silenced (FIG. 1). First, a helper strain (HS) is produced containing an NHEJ gene silencing construct (with amdS selection marker; acetamidase) and a first nutritional marker (Δhis; strain lacks histidinol dehydrogenase). This strain is fused to a target strain (TS) containing a second, different nutritional marker (Δpyr2). For convenience and easier differentiation of target and helper strain, a recessive feature can be added to the target strain (such as altered colony morphology or spore color), but this addition is optional. On minimal medium the shared cytoplasm of the forced heterokaryon allows NHEJ silencing in both strains. This heterokaryon is then transformed with a DNA fragment containing sequences homologous to the target strain genomic DNA (GR) and a selection marker that complements the nutritional marker deficiency of the target strain (pyr2; the construct is indicated as GR::pyr2). Transformants are plated on selective medium, and the predominantly uninucleate conidiospores are harvested. Conidiospores are plated on selective minimal medium without any supplements. Colonies derived from spores that have the target strain nuclei with the homologously integrated gene replacement (GR::pyr2) will grow on selective minimal medium because they are supplemented for the second nutritional marker deficiency (Δpyr). They will also have the recessive phenotype (such as altered colony morphology or spore color). The spores that only have the helper strain nuclei will not grow, since the minimal medium does not contain the first nutritional marker supplement (in this case, L-histidine). Colonies derived from heterokaryotic spores will grow on minimal medium, but their phenotype will be dominant (such as wild type colony morphology or wild type spore color), and they will be eliminated.

By the use of a helper strain silenced for the NHEJ machinery, an increase in homologous recombination can be achieved without modifying the genome of the target strain, reducing the number of laborious and time-consuming steps required for strain development.

Aspects of the disclosure are drawn to compositions and methods for homologous recombination of a donor DNA with a genomic locus in a fungal cell, e.g., a filamentous fungal cell.

Therefore, aspect of the disclosure include methods for homologous recombination of a donor DNA with a genomic locus in a fungal cell, the method comprising: (a) generating a heterokaryon between a helper fungal strain and a target fungal strain, wherein the helper fungal strain comprises an expression construct that silences the non-homologous end joining (NHEJ) mechanism; (b) introducing a donor DNA into the heterokaryon, wherein the donor DNA comprises a region of homology to a genomic locus in the target strain sufficient for homologous recombination at the genomic locus; (c) generating and plating spores from the heterokaryon cells of (b); and (d) identifying cells from the plated spores in which (i) the donor DNA has integrated into the genome by homologous recombination at the genomic locus, and (ii) the expression construct that silences the non-homologous end joining (NHEJ) mechanism is not present.

In certain embodiments, the expression construct silences one or more of: ku80, ku70, rad50, mre11, xrs2, lig4, and xrs. In certain embodiments, the expression construct silences ku80, ku70, or both.

In certain embodiments, the Cas endonuclease is a Cas9 endonuclease or variant thereof. In certain embodiments, the Cas9 endonuclease or variant thereof comprises a full length Cas9 or a functional fragment thereof from a species selected from the group consisting of: *Streptococcus* sp., *S. pyogenes*, *S. mutans*, *S. thermophilus*, *Campylobacter* sp., *C. jejuni*, *Neisseria* sp., *N. meningitides*, *Francisella* sp., *F. novicida*, and *Pasteurella* sp., *P. multocida*.

In certain embodiments, introducing the functional Cas/guide RNA complex into the heterokaryon comprises introducing a DNA construct comprising an expression cassette for the Cas endonuclease into the fungal cells.

In certain embodiments, introducing the functional Cas/guide RNA complex into the heterokaryon comprises introducing a DNA construct comprising an expression cassette for the guide RNA into the fungal cells.

In certain embodiments, the introducing step comprises directly introducing the Cas endonuclease into the fungal cells.

In certain embodiments, the introducing step comprises directly introducing the guide RNA into the fungal cells.

In certain embodiments, the fungal cell is a filamentous fungal cell. In certain embodiments, the fungal cell is a Eumycotina or Pezizomycotina fungal cell. In certain embodiments, the fungal cell is selected from the group consisting of *Trichoderma*, *Penicillium*, *Aspergillus*, *Humicola*, *Chrysosporium*, *Fusarium*, *Myceliophthora*, *Neurospora*, *Hypocrea*, and *Emericella*. In certain embodiments, the fungal cell is a *Trichoderma* sp. cell. In certain embodiments, the fungal cell is a *Trichoderma* sp., e.g., *Trichoderma reesei*.

In some embodiments, the donor DNA has partially integrated into the genome at the genomic locus of the fungal cell. In some embodiments, the donor DNA has completely integrated into the genome at the genomic locus of the fungal cell. By "partially integrated", it may include scenarios where a part of the donor DNA recombined with the genome of the fungal cell, e.g., 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or more of the donor DNA got integrated into the genome of the fungal cell.

In certain embodiments, integration of the donor DNA results in a modification of the genomic locus. In specific embodiments, the modification is selected from the group consisting of a deletion of one or more nucleotides, an insertion of one or more nucleotides, insertion of an expression cassette encoding a protein of interest, a substitution of one or more nucleotides, and any combination thereof. In some embodiments, the modification is originally present in the donor DNA. In certain embodiments, the protein of interest encoded by the expression cassette is an enzyme. In particular embodiments, the protein of interest is a hemicellulase, a peroxidase, a protease, a cellulase, a xylanase, a lipase, a phospholipase, an esterase, a cutinase, a pectinase, a keratinase, a reductase, an oxidase, a phenol oxidase, a lipoxygenase, a ligninase, a pullulanase, a tannase, a pentosanase, a mannanase, a beta-glucanase, an arabinosidase, a hyaluronidase, a chondroitinase, a laccase, an amylase, a glucoamylase, a variant thereof, a functional fragment thereof, or a hybrid or mixture of two or more thereof. In yet other particular embodiments, the protein of interest is a peptide hormone, a growth factor, a clotting factor, a chemokine, a cytokine, a lymphokine, an antibody, a receptor, an adhesion molecule, a microbial antigen, a variant thereof, a functional fragment thereof, or a hybrid or mixture of two or more thereof.

In certain embodiments, the identifying step comprises culturing cells grown from the spores from step (c) under conditions to select for or screen for the integration of the donor DNA at the genomic locus or the modification of the genomic locus. Further detail for each of these aspects is provided below.

Introduction of the Cas endonuclease, guide polynucleotide, and/or the donor DNA can be done in any convenient manner, including transfection, transduction, transformation, electroporation, particle bombardment, cell fusion techniques, etc. Each of these components can be introduced simultaneously or sequentially as desired by the user. For example, a fungal cell can first be stably transfected with a Cas expression DNA construct followed by introduction of a guide polynucleotide into the stable transfectant (either directly or using a guide polynucleotide expressing DNA construct) with. This set up may even be advantageous as the user can generate a population of stable Cas transfectant fungal cells into which different guide polynucleotides can be introduced independently (in some cases, more than one guide polynucleotide can be introduced into the same cells should this be desired). In some embodiments, a Cas expressing fungal cell is obtained by the user, and thus the user does not need to introduce a recombinant DNA construct capable of expressing a Cas endonuclease into the cell, but rather only need introduce a guide polynucleotide into the Cas expressing cell.

In certain embodiments, a guide polynucleotide is introduced into a fungal cell/heterokaryon by introducing a recombinant DNA construct that includes an expression cassette (or gene) encoding the guide polynucleotide. In some embodiments, the expression cassette is operably linked to a eukaryotic RNA pol III promoter. These promoters are of particular interest as transcription by RNA pol III does not lead to the addition of a 5' cap structure or polyadenylation that occurs upon transcription by RNA polymerase II from an RNA pol II dependent promoter. In certain embodiments, the RNA pol III promoter is a filamentous fungal cell U6 polymerase III promoter (e.g., SEQ ID NO:3 and functional variants thereof, e.g., SEQ ID NO:4; described in further detail below). In certain embodiments, the gene controlled by the U6 polymerase III promoter includes the U6 gene intron (SEQ ID NO:5) and/or the U6 gene transcriptional terminator (SEQ ID NO:6).

We have found in filamentous fungi that non-homologous insertion of transformed DNA at the double-strand break is highly favored over simple end-joining between the two ends of the chromosomal DNA at a double-strand break. Therefore, in cases where the Cas endonuclease or guide RNA is provided by transformation with an expression cassette containing DNA construct or constructs, those DNA constructs, or fragments thereof, are inserted at the double-strand break at high frequency. This insertion occurs in the absence of homology between DNA sequences on the Cas endonuclease or guide RNA expression constructs and the sequences around the double-strand break. This process is also problematic when homologous recombination between a donor DNA and a genomic locus is desired, as insertion of the entire donor DNA is favored over homologous recombination. We have found that undesirable insertion of transformed DNA occurs even when it is in the form of a vector including telomere sequences that is expected to be maintained autonomously in the fungal cell.

Certain embodiments of the present disclosure include integrating a Cas endonuclease expression cassette (and optionally a selectable marker) in the genome of a helper strain to produce a Cas endonuclease expressing helper strain. These helper cells can be employed in numerous ways to obtain a genetic modification of interest in a target strain, e.g., including homologous recombination of a donor DNA with the genome of a target strain.

For example, a Cas endonuclease expressing host cell can be used to create a "helper strain" that can provide, in trans, the Cas endonuclease to a "target strain". In brief, a heterokaryon can be created between the helper strain and the target strain, e.g., by fusion of protoplasts from each strain or by anastomosis of hyphae depending on the species of filamentous fungus. Maintenance of the heterokaryon will depend on appropriate nutritional or other marker genes or mutations in each parental strain and growth on suitable selective medium such that the parental strains are unable to grow whereas the heterokaryon, due to complementation, is able to grow. Either at the time of heterokaryon formation or subsequently, a guide RNA is introduced by transfection (and optionally a donor DNA). The guide RNA may be directly introduced or introduced via a DNA construct having a Cas endonuclease expression cassette and a selectable marker gene. Cas endonuclease is expressed from the gene in the helper strain nucleus and is present in the cytoplasm of the heterokaryon. The Cas endonuclease associates with the guide RNA to create an active complex that is targeted to the desired target site(s) in the genome. Subsequently, spores are recovered from the heterokaryon and subjected to selection or screening to recover the target strain with a modification at or near the target site (e.g., homologous recombination with the donor DNA at a genomic locus). In cases in which an expression cassette is used to introduce the guide RNA, heterokaryons are chosen in which the guide RNA expression construct is not stably maintained.

As noted above, methods of the present disclosure include introducing a DNA construct into the cell (or donor DNA) that has DNA sequence homology with regions of the chromosomal DNA (e.g., on each side of the target site of the Cas/guide RNA complex). The intent is for the DNA fragment (e.g., a linear DNA fragment) to integrate by homologous integration/recombination into the target cell genome.

With respect to DNA repair in fungal cells, we have found that in the presence of a functioning NHEJ pathway, error-prone repair is highly favored over homologous recombination at a double strand break site. In other words, with respect to DNA repair of a double strand break (e.g., those introduced at a target site by a Cas/guide RNA complex) in filamentous fungal cells, we have found that in the presence of a functioning NHEJ pathway, non-homologous insertion of DNA at the break is highly favored over (1) non-homologous end joining without DNA insertion and (2) homologous recombination at the double strand break site with a donor DNA. Therefore, in certain aspects of the present invention, the functioning of the non-homologous end joining (NHEJ) pathway at the target site in the fungal cell in the population is inhibited, not activated, non-functional, or reduced. This may be achieved in any convenient manner, some of which are described below.

In some instances, the donor DNA includes a first region and a second region that are homologous to corresponding first and second regions in the genome of the fungal cell. For example, the regions of homology can include or surround the target site at which the genomic DNA is cleaved by a Cas endonuclease. These regions of homology promote homologous recombination with their corresponding genomic regions of homology resulting in exchange of DNA between the donor DNA and the genome. As such, the provided methods result in the integration of the polynucleotide of interest of the donor DNA at a homologous region in the target cell genome of a heterokaryon, which, upon applying appropriate sporulation/selection criteria to the heterokaryon, generates an altered genome in the target cell.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the fungal cell genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, such that the sequences undergo homologous recombination.

The donor DNA may be introduced by any convenient means (as discussed elsewhere herein).

In certain embodiments in which a Cas/guide RNA system is employed, the Cas endonuclease is a Cas9 endonuclease (see, e.g., WO 2013141680 entitled "RNA-directed DNA Cleavage by the Cas9-crRNA Complex"). Examples of Cas9 endonucleases include those from *Streptococcus* sp. (e.g., *S. pyogenes, S. mutans*, and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*) (e.g., SEQ ID NOs:8 and 11 to 16, functional fragments thereof, and sequences having at least 80% sequence identity to any one of these sequences that retain functional activity) (see, e.g., Cas9 endonucleases described in Fonfara et al., Nucleic Acids Res., 2013, pages 1-14: incorporated herein by reference). In some embodiments, the Cas endonuclease is encoded by an optimized Cas9 endonuclease gene, e.g., optimized for expression in a fungal cell (e.g., Cas9 encoding genes containing SEQ ID NO:7, e.g., SEQ ID NO:1, as described below).

In certain instances, the Cas endonuclease gene is operably linked to one or more polynucleotides encoding nuclear localization signals such that the Cas endonuclease/guide polynucleotide complex that is expressed in the cell is efficiently transported to the nucleus. Any convenient nuclear localization signal may be used, e.g., a polynucleotide encoding an SV40 nuclear localization signal present upstream of and in-frame with the Cas codon region and a polynucleotide encoding a nuclear localization signal derived from the *T. reesei* blr2 (blue light regulator 2) gene present downstream and in frame with the Cas codon region. Other nuclear localization signals can be employed. For example, the Cas endonuclease can be operably linked to one or more nuclear targeting signal (also referred to as a nuclear localization signal/sequence; NLS). SEQ ID NO:1 and SEQ ID NO:2 provide an example of a filamentous fungal cell optimized Cas9 gene with NLS sequences at the N- and C-termini and the encoded amino acid sequence, respectively. Many different NLSs are known in eukaryotes. They include monopartite, bipartite and tripartite types. Any convenient NLS can be used, the monopartite type being somewhat more convenient with examples including the SV40 NLS, a NLS derived from the *T. reesei* blr2 (blue light regulator 2) gene, or a combination of both.

In certain embodiments of the disclosure, the guide polynucleotide is a guide RNA that includes a crRNA region (or crRNA fragment) and a tracrRNA region (or tracrRNA fragment) of the type II CRISPR/Cas system that can form a complex with a type II Cas endonuclease. As indicated above, the guide RNA/Cas endonuclease complex can direct the Cas endonuclease to a fungal cell genomic target site, enabling the Cas endonuclease to introduce a double strand break into the genomic target site. In some cases, the RNA that guides the RNA/Cas9 endonuclease complex is a duplex that includes a crRNA and a separate tracrRNA. In other instances, the guide RNA is a single RNA molecule that includes both a crRNA region and a tracrRNA region (sometimes referred to herein as a fused guide RNA). One advantage of using a fused guide RNA versus a duplexed crRNA-tracrRNA is that only one expression cassette needs to be made to express the fused guide RNA.

Virtually any site in a fungal cell genome may be targeted by a Cas endonuclease using the disclosed methods, so long as the target site includes the required protospacer adjacent motif (PAM). In the case of the *S. pyogenes* Cas9, the PAM has the sequence NGG (5' to 3'; where N is A, G, C or T), and thus does not impose significant restrictions on the selection of a target site in the genome. Other known Cas9 endonucleases have different PAM sites (see, e.g., Cas9 endonuclease PAM sites described in Fonfara et al., Nucleic Acids Res., 2013, pages 1-14: incorporated herein by reference).

The length of the target site can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The cleavage site can be within the target sequence or the cleavage site could be outside of the target sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs.

In some cases, active variant target sequences in the genome of the fungal cell can also be used, meaning that the target site is not 100% identical to the relevant sequence in the guide polynucleotide (within the crRNA sequence of the guide polynucleotide). Such active variants can comprise at least 65%, 70%, 75%, 80%, 85%, 90%, 91%, 92%, 93%, 94%, 95%, 96%, 97%, 98%, 99% or more sequence identity to the given target site, wherein the active variant target sequences retain biological activity and hence are capable of being recognized and cleaved by a Cas endonuclease. Assays to measure the double-strand break of a target site by an endonuclease are known in the art and generally measure the overall activity and specificity of the agent on DNA substrates containing recognition sites.

Target sites of interest include those located within a region of a gene of interest. Non-limiting examples of regions within a gene of interest include an open reading frame, a promoter, a transcriptional regulatory element, a translational regulatory element, a transcriptional terminator sequence, an mRNA splice site, a protein coding sequence, an intron site, and an intron enhancing motif. In certain cases, when the donor DNA comprises a region of homology to a genomic locus of the fungal cells, the Cas endonuclease and guide RNA introduced to the fungal cells are capable of forming a complex that enables the Cas endonuclease to act at a target site in or near the genomic locus of the fungal cells. In some embodiments, the Cas endonuclease cut site (or target site) on the genomic DNA is in the homologous region between the donor DNA and the genomic locus, where homologous recombination can occur. In other embodiments, the cut site is near the homologous region between the donor DNA and the genomic locus which can be anywhere from 1 bp to about 10 kb away from the homologous region, e.g., 1 bp, 2 bp, 5 bp, 10 bp, 20 bp, 50 bp, 100 bp, 250 bp, 500 bp, 1 kb, 2 kb, 3 kb, 4 kb, 5 kb, 6 kb, 7 kb, 8 kb, 9 kb, or 10 kb away from the site of homologous region.

In certain embodiments, modification of the genome of the fungal cell results in a phenotypic effect that can be detected and, in many instances, is a desired outcome of the user. Non-limiting examples include acquisition of a selectable cell growth phenotype (e.g., resistance to or sensitivity to an antibiotic, gain or loss of an auxotrophic characteristic, increased or decreased rate of growth, etc.), expression of a detectable marker (e.g., fluorescent marker, cell-surface molecule, chromogenic enzyme, etc.), and the secretion of an enzyme the activity of which can be detected in culture supernatant.

When modification of the genome of the fungal cell results in a phenotypic effect, a donor DNA is often employed that includes a polynucleotide of interest that is (or encodes) a phenotypic marker. Any convenient phenotypic marker can be used, including any selectable or screenable marker that allows one to identify, select for, or screen for or against a fungal cell that contains it, often under particular culture conditions. Thus, in some aspects of the present invention, the identification of fungal cells having a desired genome modification includes culturing the fungal population of cells that have received the Cas endonuclease and guide polynucleotide (and optionally a donor DNA) under conditions to select for or screen for cells having the modification at the target site. Any type of selection system may be employed, including assessing for the gain or loss of an enzymatic activity in the fungal cell (also referred to as a selectable marker), e.g., the acquisition of antibiotic resistance or gain/loss of an auxotrophic marker.

In some instances, the genomic modification in the fungal cells is detected directly using any convenient method, including sequencing, PCR, Southern blot, restriction enzyme analysis, and the like, including combinations of such methods.

In some embodiments, specific genes are targeted for modification using the disclosed methods, including genes encoding enzymes, e.g., acetyl esterases, aminopeptidases, amylases, arabinases, arabinofuranosidases, carboxypeptidases, catalases, cellulases, chitinases, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, transferases, transport proteins, transglutaminases, xylanases, hexose oxidases, and combinations thereof.

Aspects of the present disclosure are drawn to recombinant fungal cells produced by the methods described above as well as those for use as parental host cells in performing the methods.

Additional embodiments of the methods and compositions of the present disclosure are shown herein. Non-limiting examples or embodiments of the methods and compositions disclosed herein are as follows:

1. A method for homologous recombination of a donor DNA with a genomic locus in a fungal cell, the method comprising:
   (a) generating a heterokaryon between a helper fungal strain and a target fungal strain, wherein the helper fungal strain comprises an expression construct that silences the non-homologous end joining (NHEJ) mechanism;
   (b) introducing a donor DNA into the heterokaryon, wherein the donor DNA comprises a region of homology to a genomic locus in the target strain sufficient for homologous recombination at the genomic locus;
   (c) generating and plating spores from the heterokaryon cells of (b); and
   (d) identifying cells from the plated spores in which (i) the donor DNA has integrated into the genome by homologous recombination at the genomic locus, and (ii) the expression construct that silences the non-homologous end joining (NHEJ) mechanism is not present.
2. The method of embodiment 1, wherein the expression construct silences one or more of: ku80, ku70, rad50, mre11, xrs2, lig4, and xrs.
3. The method of embodiment 2, wherein the expression construct silences ku80, ku70, or both.
4. The method of any one of embodiments 1 to 3, further comprising introducing a functional Cas/guide RNA complex into the heterokaryon, wherein the Cas/guide RNA complex has a target site within the genomic locus.
5. The method of embodiment 4, wherein the Cas is a Cas nickase.
6. The method of any preceding embodiment, wherein the donor DNA comprises a polynucleotide sequence of interest, wherein homologous recombination at the genomic locus results in insertion of the polynucleotide sequence of interest in the genomic locus.
7. The method of any preceding embodiment, wherein the Cas endonuclease is a Cas9 endonuclease or variant thereof.
8. The method of embodiment 7, wherein the Cas9 endonuclease or variant thereof comprises a full length Cas9 or a functional fragment thereof from a species selected from the group consisting of: *Streptococcus* sp., *S. pyogenes*, *S. mutans*, *S. thermophilus*, *Campylobacter* sp., *C. jejuni*, *Neisseria* sp., *N. meningitides*, *Francisella* sp., *F. novicida*, and *Pasteurella* sp., *P. multocida*.
9. The method of any one of embodiments 4 to 8, wherein introducing the functional Cas/guide RNA complex into the heterokaryon comprises introducing a DNA construct comprising an expression cassette for the Cas endonuclease into the fungal cells.
10. The method of any one of embodiments 4 to 9, wherein introducing the functional Cas/guide RNA complex into the heterokaryon comprises introducing a DNA construct comprising an expression cassette for the guide RNA into the fungal cells.
11. The method of any one of embodiments 4 to 8 or 10, wherein the introducing step comprises directly introducing the Cas endonuclease into the fungal cells.
12. The method of any one of embodiments 4 to 9 or 11, wherein the introducing step comprises directly introducing the guide RNA into the fungal cells.
13. The method of any preceding embodiment, wherein the fungal cell is a filamentous fungal cell.
14. The method of any preceding embodiment, wherein the fungal cell is a Eumycotina or Pezizomycotina fungal cell.
15. The method of any preceding embodiment, wherein filamentous fungal cell is selected from the group consisting of *Trichoderma*, *Penicillium*, *Aspergillus*, *Humicola*, *Chrysosporium*, *Fusarium*, *Myceliophthora*, *Neurospora*, *Hypocrea*, and *Emericella*.
16. The method of any preceding embodiment, wherein the fungal cell is a *Trichoderma* sp. cell.
17. The method of embodiment 16, wherein the *Trichoderma* sp. is *Trichoderma reesei*.
18. The method of any preceding embodiment, wherein the donor DNA has partially integrated into the genome at the genomic locus.
19. The method of any preceding embodiment, wherein integration of the donor DNA results in a modification of the genomic locus.
20. The method of embodiment 19, wherein the modification is selected from the group consisting of a deletion of one or more nucleotides, an insertion of one or more nucleotides, insertion of an expression cassette encoding a protein of interest, a substitution of one or more nucleotides, and any combination thereof.
21. The method of any preceding embodiment, wherein the identifying step comprises culturing cells grown from the spores from step (c) under conditions to select for or screen for the integration of the donor DNA at the genomic locus or the modification of the genomic locus.
22. A recombinant fungal cell produced by the method of any preceding embodiment.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

This helper strain-based concept can provide benefits to any project where *T. reesei* or another filamentous fungus is used as a host, and where a high rate of homologous integration is required.

Example 1

Use of Helper Strain for Complementing Colonial Growth and Determining Allele Dominance Experiments were performed to use a helper strain for complementing colonial growth and determining allele dominance. The work flow and the result of one of such experiments are shown in FIG. 7. Steps of this experiment include:

1) Fusing helper strain (HS) and target strain (CS, or Colonial Strain in FIG. 7) to form a heterokaryon;
2) Generating conidiospores from the heterokaryon;
3) Harvesting the conidiospores and diluting to appropriate concentration;
4) Plating conidiospores on selective media and counting colonies to score the phenotype and auxotrophy; and
5) Confirming the strains obtained.

In this particular experiment the helper strain (HS) is a RL-P37 Δcbh1 Δcbh2 Δegl1 Δegl2 Δhis3 strain with wild type colony growth rates and conidiation, and the target colonial strain (CS) is a RL-P37 Δcbh1 Δcbh2 Δegl1 Δegl2 Δpyr2 strain with deletion of a gene of interest which changes a feature of interest (in this experiment the feature of interest is normal colony growth rates and conidiation, so the gene deletion strain has reduced colony growth rates and conidiation). Protoplasts of the HS strain and the CS strain were co-inoculated on minimal medium plates supplemented with sorbitol. After the strains fused to form a heterokaryon and started growing, they were transferred to minimal medium plates without supplements and grown in conditions that promote production of conidiospores at 28° C. and a 12 h light-dark cycle. The heterokaryon had a wild type colony growth and conidiation equivalent to the helper strain, indicating that the reduced colony growth and conidiation of the CS strain are complemented and that the mutation in the gene of interest is recessive. Mature conidiospores were harvested from the heterokaryon, and serial dilutions of conidiospores were plated on selective minimal medium supplemented with either histidine or uridine. Colonies that grew upon transfer to minimal medium were identified as heterokaryons and eliminated. All the strains that grew on minimal medium supplemented with histidine had wild type colony growth and conidiation, features associate with the helper strain. All the strains that grew on minimal medium supplemented with uridine had reduced colony growth and conidiation, features associated with the recessive mutation in the gene of interest. This indicated that the strain with sub-optimal reduced colony growth and conidiation containing the recessive mutation in the gene of interest could be rescued from the heterokaryon.

Example 2

Silencing of NHEJ Mechanism in Fungal Cells with DNA Constructs Constructs

The pAVTrku80sil construct for silencing ku80 (FIG. 2A) contains a sense and antisense ku80 DNA sequence interrupted with an intron sequence, and is driven by a divergent promoter. The divergent promoter also drives the expression of *Ptilosarcus* sp. green fluorescent protein (PtGFP), which serves as an indicator of the antisense cassette expression. The construct also contains the amdS selective marker.

The intermediate construct for silencing both ku80 and ku70 (pAVTrku70ku80sil, FIG. 2B), and another construct for silencing ku70, lig4 and ku80 (pAVTrku70lig4ku80sil, FIG. 2C) have been generated and verified. They contain approximately 500 bp sense sequences of the respective genes, an intron and the equivalent antisense sequences, followed by the ku70 terminator sequence in the yeast pRS426 vector backbone.

The gene replacement construct fragments incorporated into the pRS426 vector have been assembled in vitro and cloned in yeast. The gene replacement cassette with the pyr2 marker will be amplified from this construct.

Strains

Figure 2A:
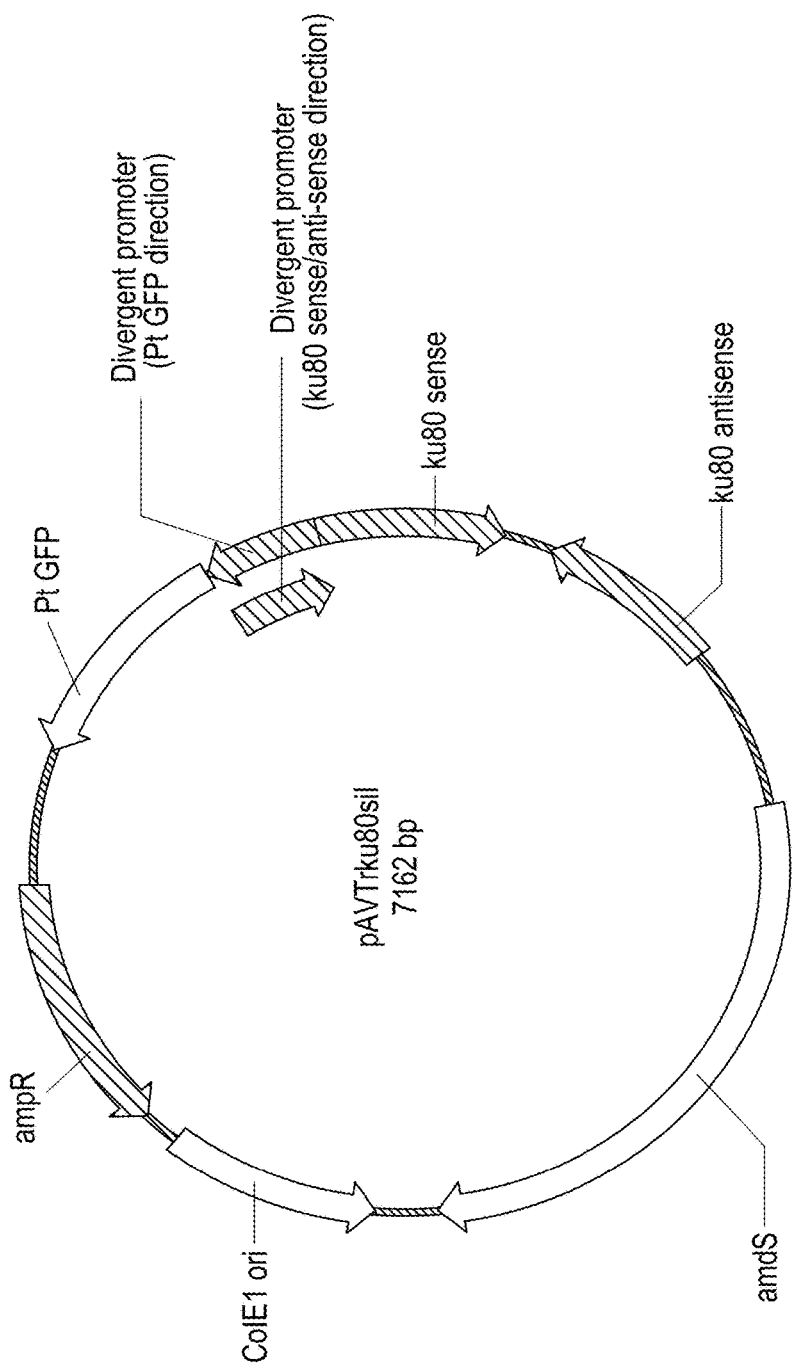
FIGS. 2A-2C. Illustrations of Ku80 silencing constructs: pAVTrku80sil (FIG. 2A), pAVTrku70ku80sil (FIG. 2B), and pAVTrku70lig4ku80sil (FIG. 2C).
Figure 2B:
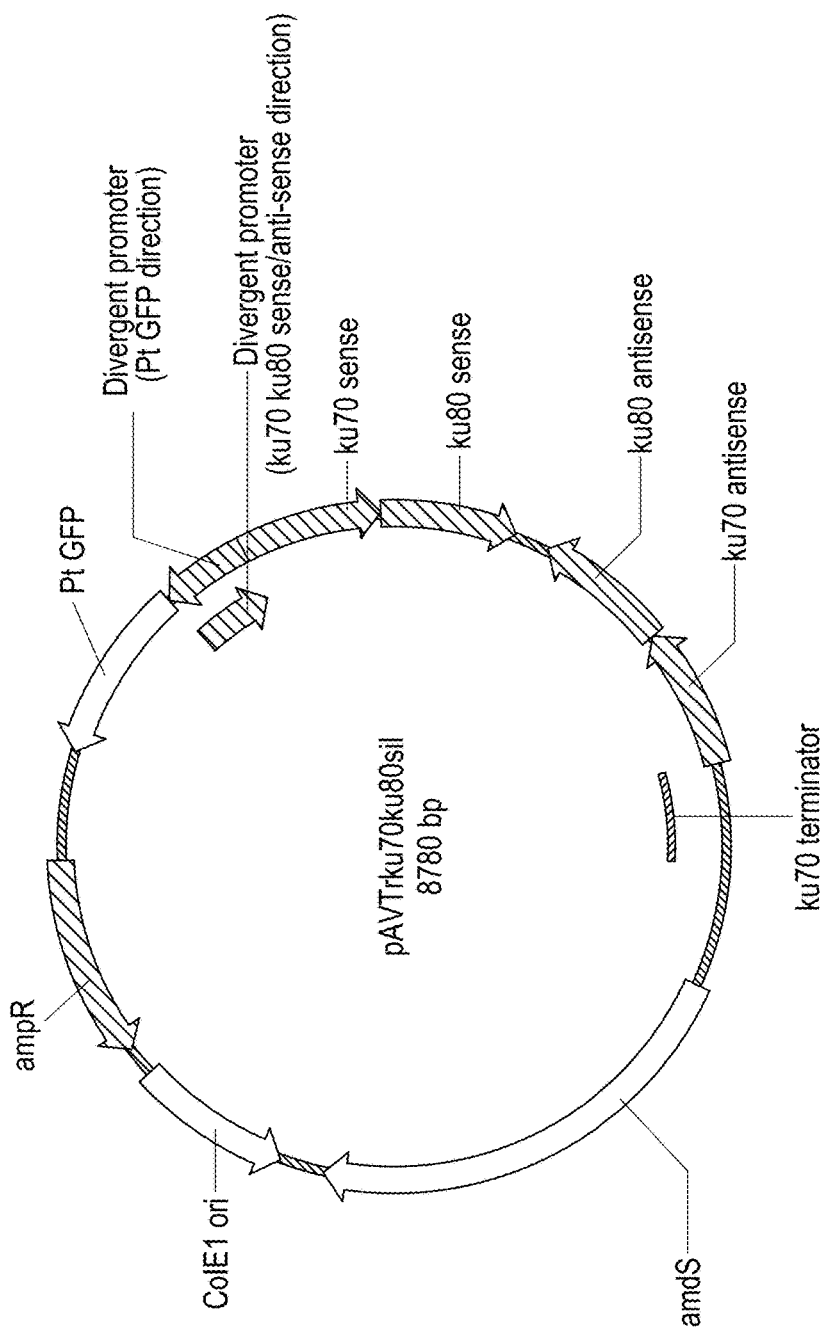
Figure 2C:
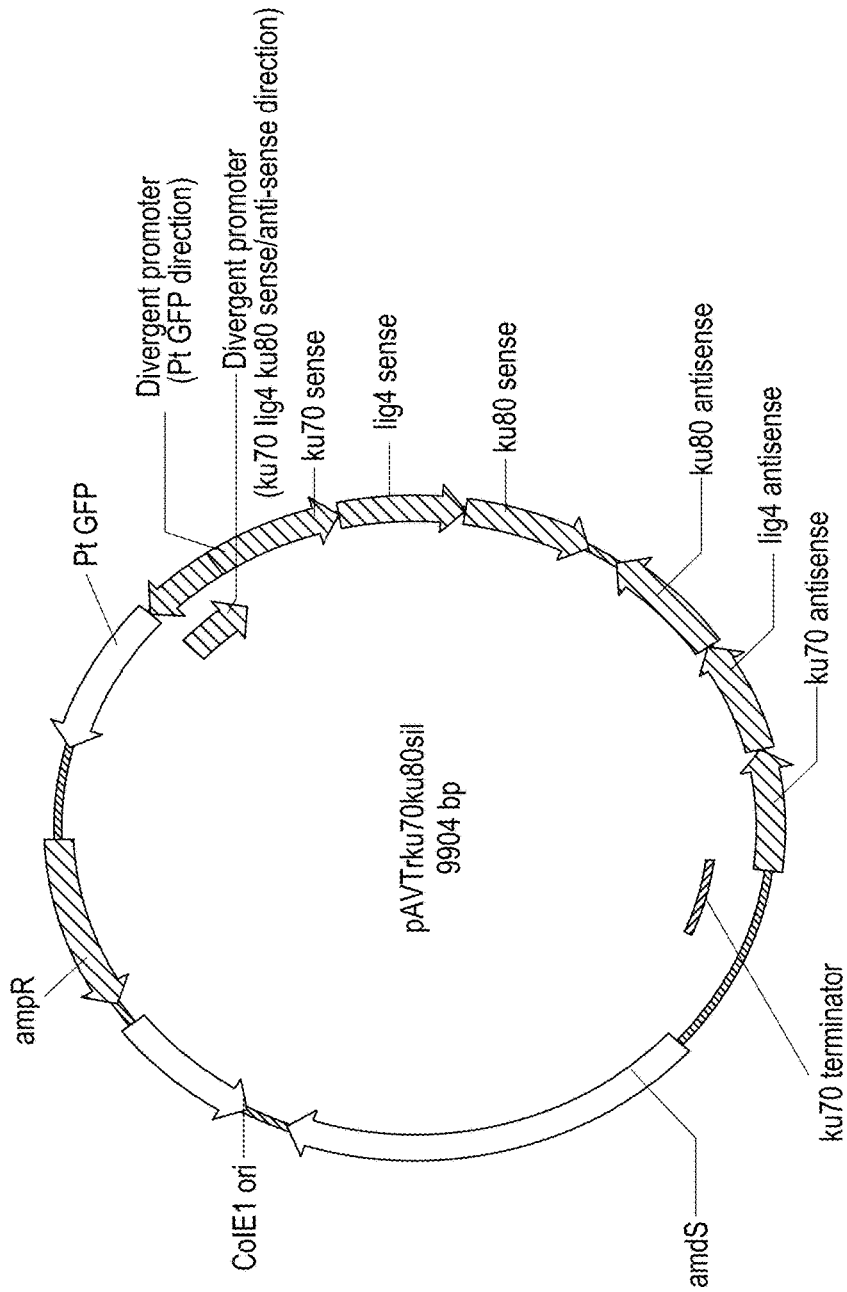

A *T. reesei* strain (RL-P37 Δcbh1 Δcbh2 Δegl1 Δegl2) was transformed with the *T. reesei* ku80 gene silencing construct (FIG. 2A). Six stable candidates with a strong GFP signal were selected, verified and spore-purified. Four spore-purified isolates from each of the six candidates were grown in 24-well plates and the intensity of the GFP signal, indicative of the level of silencing, was assessed. One spore-purified isolate from each candidate with the highest GFP signal was selected for transformation with a Δhis3::hph deletion construct.

Protocol

Figure 3:
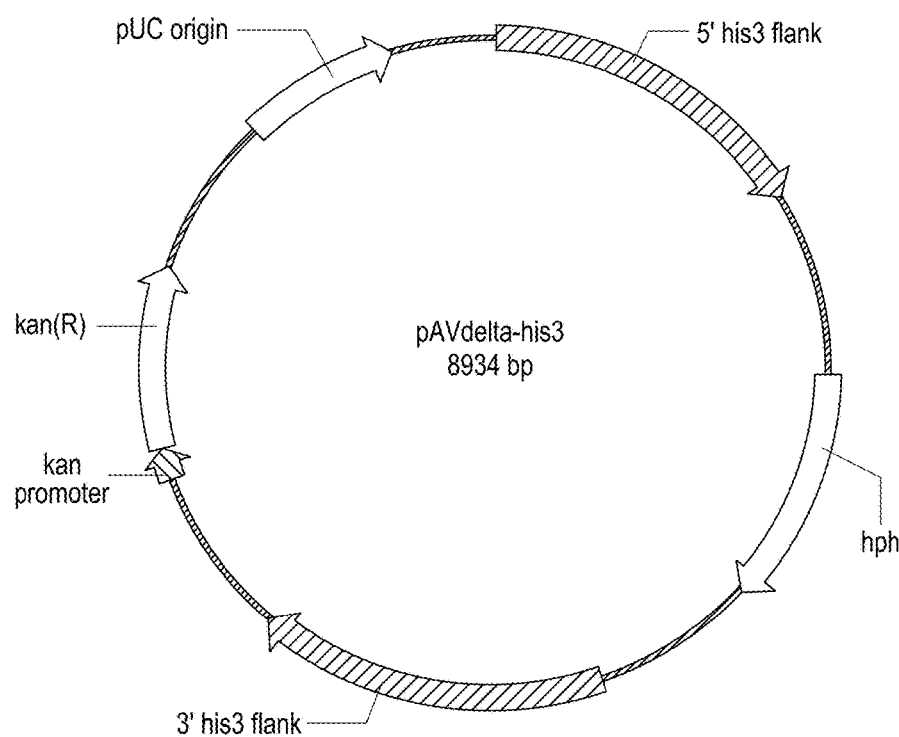
FIG. 3. Illustration of a his3 deletion construct pAVdelta-his3. hph=hygromycin resistance gene encoding hygromycin phosphotransferase from *E. coli*, kan(R)=kanamycin resistance gene encoding phosphotransferase.
Figure 4:
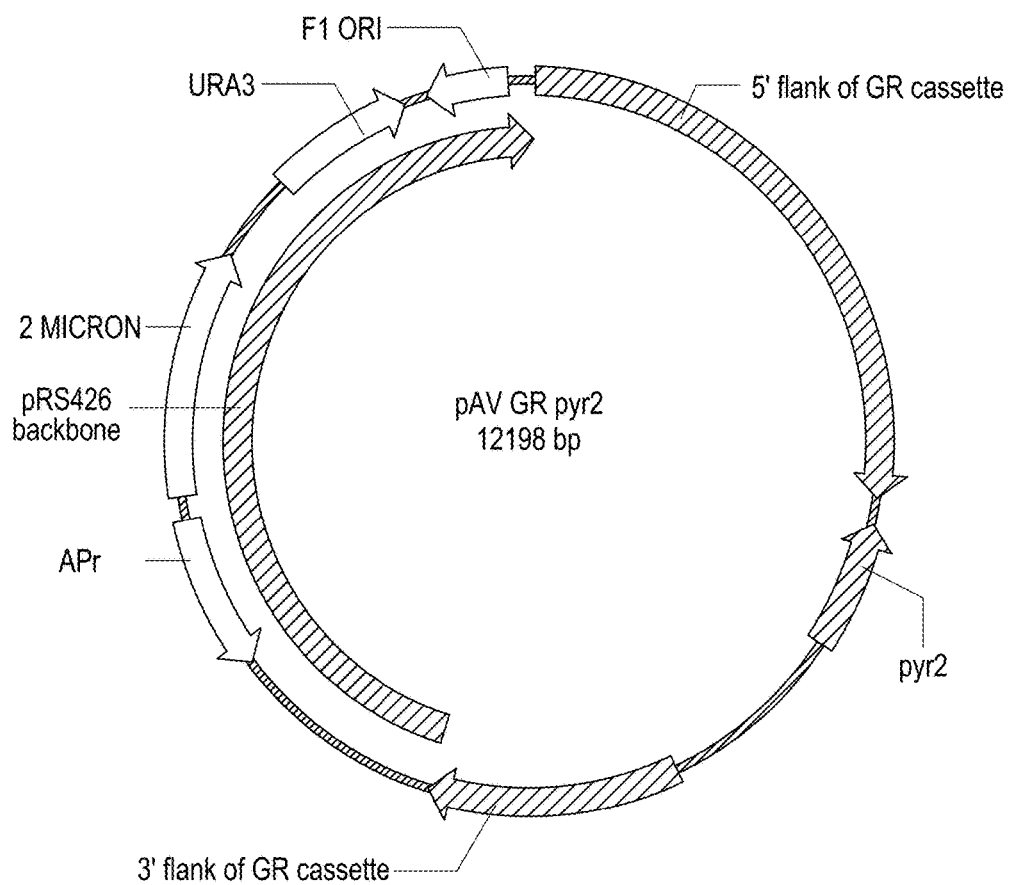
FIG. 4. Gene replacement (GR) construct pAV GR pyr2. pyr2=gene encoding orotidine 5'-monophosphate pyrophosphorylase, Apr=ampicillin resistance gene encoding β-lactamase, F1 ORI=F1 origin of replication, URA3=*Saccharomyces cerevisiae* gene encoding orotidine 5'-phosphate decarboxylase, 2 MICRON=*S. cerevisiae* 2-micron plasmid-originating sequence.

Spore-purified strains from above containing the silencing constructs with the highest level of GFP expression were tested for the efficiency of homologous integration by transforming with a linear his3 deletion cassette (FIG. 3) containing the hph selective marker. The silencing strain with the highest proportion of transformants containing the Δhis3 deletion (60%), indicating highest levels of NHEJ silencing, was selected and will be used as the helper strain. The helper strain will be fused with a host strain that has a non-functional pyr2 locus (a nutritional marker), and optionally an altered colony morphology (a recessive feature). The forced heterokaryon grown on minimal medium will then be transformed by PEG transformation with a linear gene replacement construct (FIG. 4) containing a functional pyr2 marker as the selective marker (this marker is also a nutritional marker), and plated on minimal medium. Conidiospores will be harvested and serial dilutions plated on minimal medium. Colonies that grow on minimal medium (and have altered colony morphology, if that feature was included) will be assessed for homologous recombination of the deletion construct, and efficiency of homologous recombination will be determined.

Specific, non-limiting examples of how the helper strain compositions and methods can be employed are described below.

Example 3

Use of cre Recombinase in a Helper Strain or Heterokaryon for Removal of DNA Fragments in a Target Cell In one embodiment, a user can express cre recombinase in a helper strain and use it for removal of any DNA fragment in a target cell flanked by loxP sites.

Figure 6:
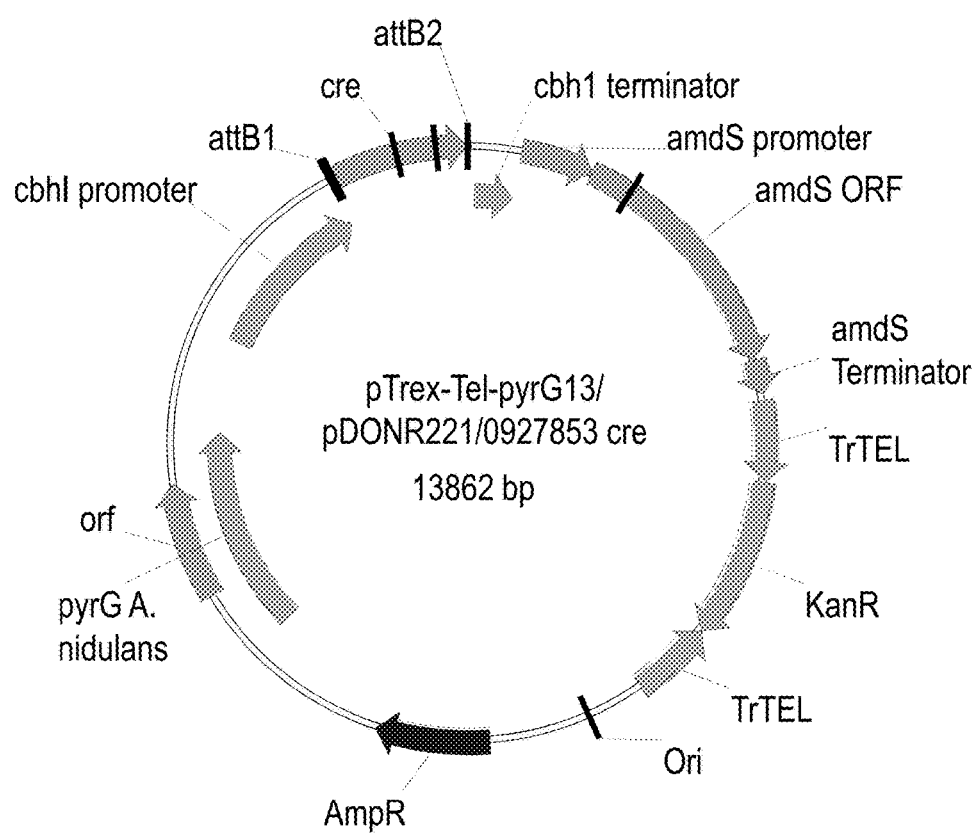
FIG. 6. Telomeric vector containing the cre recombinase gene (Expression Clone/pTrex-Tel-pyrG13/pDONR221/0927853cre).

In another embodiment, a user can introduce a telomeric vector expressing cre recombinase into a heterokaryon, and simultaneously remove one or more DNA fragments flanked by loxP sites in each of the helper and target strains. A schematic example is shown in FIG. 5. Two deletion strains, each with a deletion cassette containing the hph marker flanked by two loxP sites at the ad3A (Strain 2) or his3 (Strain 1) loci of a wild type strain, were obtained by homologous recombination. To recycle the hph marker and concurrently remove it from one or both strains, Strain 1 and Strain 2 were first fused into a forced heterokaryon using the procedure described in Example 1. The heterokaryon was then transformed with a cre-containing telomeric vector (FIG. 6) carrying an amdS marker by biolistic or PEG transformation, and then propagated on appropriate acetamide-containing plates to maintain the vector. While under selection, the telomeric vector provided Cre to both component strains without integrating into the genomes, allowing recombination at loxP sites and looping-out of the hph marker in one or both contributing genomes. Conidiospores from the transformed heterokaryon were harvested and plated on PDA medium supplemented with adenine and histidine. After a defined number of transfers on supplemented PDA medium, individual colonies were tested for auxotrophies, and resistance to hygromycin B. Strains with ad3A and his3 deletions that have looped-out the hph cassette were not resistant to hygromycin B. To ensure that the rare event of telomeric vector incorporation into the genome did not occur, the strains were tested for the presence of a telomeric vector DNA fragment by PCR analysis, and candidates that had incorporated the cre-containing telomeric vector were eliminated. A wild type Δhis3 Δhph strain was confirmed by diagnostic PCR. The results indicate that the cre recombinase expressed from the telomeric vector introduced into the heterokaryon were able to successfully remove one or more DNA fragments flanked by loxP sites in each of the helper and target strains without integration of the vector into the genome.

Example 4

Use of Cas RNA-Guided Endonuclease in a Helper Strain for Creating Targeted Double-Strand DNA Breaks in a Target Cell In another embodiment a user can express a Cas RNA-guided endonuclease in a helper strain which preferably has silenced NHEJ- and use it to create targeted double-strand DNA breaks in a target cell. One benefit is that a double-strand DNA break stimulates integration of a donor DNA fragment by homologous recombination at the target site. Silencing NHEJ minimizes the frequency with which the donor DNA fragment integrates via the NHEJ pathway. In one experiment, a helper strain containing a NHEJ-silencing DNA construct as described in Example 2 and which has exhibited efficient homologous recombination is transformed with a Cas9 expression vector (FIG. 8) similar to those disclosed in PCT application no. PCT/CN2014/093914 (filed Dec. 16, 2014, hereby incorporated by reference). This vector uses a mutant version of the T. reesei als1 gene that confers resistance to chlorimuron ethyl as selectable marker and transformants that have stably integrated the vector into the chromosomal DNA are selected as a new helper strain. This helper strain is fused with a target strain (with non-functional pyr2 gene) to create a forced heterokaryon on selective medium lacking histidine and uridine. The heterokaryon is then co-transformed with a mix of sgRNA (single-guide RNA) and a donor DNA fragment for which integration at a defined target site within the genome of the target cell is desired. The sgRNA is designed to direct cas9 endonuclease to said defined target site and is generated using an in vitro transcription reaction as described in PCT application no. PCT/CN2014/093916 (filed Dec. 16, 2014, hereby incorporated by reference)). Examples of sequences of sgRNAs designed to direct Cas9 to the ad3A, glucoamylase (TrGA), or pyr2 gene of T. reesei are provided as follows.

sgRNA: gAd3A TS1;

SEQ ID NO: 17 guccucgagcaaaaggugccGUUUUAGAGCUAGAAAUAGCAAGUUAAAAU
AAGGCUAGUCCGUUAUCAACUUGAAAAAGUGGCACCGAGUCGGUGGUGC.

sgRNA: gTrGA TS2;

SEQ ID NO: 18 guucagugcaauaggcgucuGUUUUAGAGCUAGAAAUAGCAAGUUAAAAU
AAGGCUAGUCCGUUAUCAACUUGAAAAAGUGGCACCGAGUCGGUGGUGC sgRNA: gTrGA TS11;

SEQ ID NO: 19 gccaauggcgacggcagcacGUUUUAGAGCUAGAAAUAGCAAGUUAAAAU
AAGGCUAGUCCGUUAUCAACUUGAAAAAGUGGCACCGAGUCGGUGGUGC sgRNA: gPyr2 TS6;

SEQ ID NO: 20 gcacagcgggaugcccuuguGUUUUAGAGCUAGAAAUAGCAAGUUAAAAU
AAGGCUAGUCCGUUAUCAACUUGAAAAAGUGGCACCGAGUCGGUGGUGC Alternatively, in place of the sgRNA a DNA construct including a sgRNA expression cassette is included in the co-transformation. The DNA fragment for which integration at a defined target site is desired includes terminal regions of homology with the flanking DNA regions on either side of the cas9 target site. It also includes a selectable marker (such as pyr2) and an expression cassette for a gene of interest. Upon sporulation of the heterokaryon and plating of spores, colonies with the target cell phenotype but prototrophic for uridine (pyr2+) are isolated and screened for integration of the DNA fragment at the target site. Advantageously, this method allows efficient generation of transformants having different genes of interest integrated at the same target site.

Although the foregoing compositions and methods have been described in some detail by way of illustration and example for purposes of clarity of understanding, it is readily apparent to those of ordinary skill in the art in light of the teachings herein that certain changes and modifications may be made thereto without departing from the spirit or scope of the appended claims.

Accordingly, the preceding merely illustrates the principles of the present compositions and methods. It will be appreciated that those skilled in the art will be able to devise various arrangements which, although not explicitly described or shown herein, embody the principles of the present compositions and methods and are included within its spirit and scope. Furthermore, all examples and conditional language recited herein are principally intended to aid the reader in understanding the principles of the present compositions and methods and the concepts contributed by the inventors to furthering the art, and are to be construed as being without limitation to such specifically recited examples and conditions. Moreover, all statements herein reciting principles, aspects, and embodiments of the present compositions and methods as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present compositions and methods, therefore, is not intended to be limited to the exemplary embodiments shown and described herein.

SEQUENCES

SEQ ID NO: 1
Codon optimized *Streptococcus pyogenes* Cas9-encoding gene; with N- and C- terminal NLS sequences
atggcaccgaagaagaagcgcaaggtgatggacaagaagtacagcatcgg
cctcgacatcggcaccaactcggtgggctgggccgtcatcacggacgaat
ataaggtccccgtcgaagaagttcaaggtcctcggcaatacagaccgccac
agcatcaagaaaaacttgatcggcgccctcctgttcgatagcggcgagac
gcgcgaggcgaccaggctcaagaggaccgccaggagacggtacactaggc
gcaagaacaggatctgctacctgcaggagatcttcagcaacgagatggcg
aaggtggacgactccttcttccaccgcctggaggaatcattcctggtgga
ggaggacaagaagcatgagcggcacccaatcttcggcaacatcgtcgacg
aggtggcctaccacgagaagtacccgacaatctaccacctccggaagaaa
ctggtggacagcacagacaaggcggacctccggctcatcaccttgcct
cgcgcatatgatcaagttccgcggccacttcctcatcgaggggcaactt
acccggacaactccgacgtggcaagctgttcatccagctcgtgcagacg
tacaatcaactgttcgaggagaaccccataaacgctagcggcgtggacgc
caaggccatcctctcggccaggctctcgaaatcaagaaggctggagaacc
ttatcgccgcagttgccaggcgaaaagaacggcctcttcggcaacctt
attgcgctcagcctcggcctgaccgccgaacttcaaatcaaacttcgacct
cgcggaggacgccaagctccagctctcaaaggacacctacgacgacgacc
tcgacaacctcctggcccagatagagaccagtacgcggacctcttcctc
gccgccaagaacctctccgacgctatcctgctcagcgacatccttcggt
caacaccgaaattaccaaggcaccgctgtccgccagcatgattaaacgct
acgacgagcaccatcaggacctcacgctgctcaaggcactcgtccgccag
cagctccccgagaagtacaaggagatcttcttcgaccaatcaaaaacgg
ctacgcgggatatatcgacggcggtgccagccaggaagagttctacaagt
tcatcaaaccaatcctggagaagatggacggcaccggaggagttgctggtc
aagctcaacagggaggacctcctcaggaagcagaggaccttcgacaacgg
ctccatcccgcatcagatccacctgggcgaactgcatgccatcctgcgc
gccaggaggacttctacccgttcctgaaggataacccgggagaagatcgag
aagtcttgacgttccgcatcccatactacgtgggccgctggctcgcgg
caactcccggttcgcctggatgacccggaagtcggaggagaccatcacac
cctggaactttgaggaggtggtcgataaggccgctagcgctcagagcttc
atcgagcgcatgaccaacttcgataaaaacctgcccaatgaaaaagtcct
ccccaagcactcgctgctctacgagtacttcaccgtgtacaacgagctca
ccaaggtcaaatacgtcaccgagggcatgcggaagccggcgttcctgagc
ggcgagcagaagaaggcgatagtggacctcctcttcaagaccaacaggaa
ggtgaccgtgaagcaattaaaagaggactacttcaagaaaatagagtgct
tcgactccgtggagatctcgggcgtggagatcggttcaacgcctcactc
ggcacgtatcacgacctcctcaagatcattaagacaaggacttcctcga
caacgaggagaacgaggacatcctcgaggacatcgtcctcacccctgaccc
tgttcgaggaccgcgaaatgatcgaggagaggctgaagacctacgcgcac
ctgttcgacgacaaggtcatgaaacagctcaagaggcgccgctacactgg
ttgggggaaggctgtcccgcaagctcattaatggcatcagggacaagcaga
gcgggcaagaccatcctggacttcctcaagtccgacggggttcgccaacgc
aacttcatgcagctcattcacgacgactgctcacgttcaaggaagacat
ccagaaggcacaggtgagcgggcagggtgactccctccacgaacacatcg
ccaacctggccggctcgcggccattaaaaaggcatcctgcagacggtc
aaggtcgtcgacgagctcgtgaaggtgatgggccggcacaagcccgaaaa
tatcgtcatagagatggccaggagaaccagaccaccccaaaaagggcaga
agaactcgcgcgagcggatgaaacggatcgagagggcattaaagagctc
gggtcccagatcctgaaggagcacccgtggaaaatacccagctccagaa
tgaaaagctctacctctactacctgcagaacggccgcgacatgtacgtgg
accaggagctggacattaatcggctatcggactacgacgtgaccacatc
gtgccgcagtcgttcctcaaggacgatagcatcgacaacaaggtgctcac
ccggtcggataaaaatcggggcaagcgacaacgtgcccagcgaggagg
tcgtgaaagaagatgaaaaactactggcgcagctcctcaacgcgaaactg
atcacccagcgcaagttcgacaacctgacgaaggcggaacggtggctt
gagcgaactcgataaggcgggcttcataaaaaggcagctggtcgagacgc
gccagatcacgaaggcatgtccgccaagtcctggacagccgcgcatgaatact
aagtacgatgaaaacgacaagctgatccggagggtgaaggtgatcacgct
gaagtccaagctcgtgtcggacttccgcaaggacttccagttctacaagg
tccgcgagatcaacaactaccaccacgcccacgacgcctacctgaatgcg
gtggtcgggaccgccctgatcaagaaagtacccgaagctggagtcggagtt
cgtgtacggcgactacaaggtctacgacgtgcgcaaaatgatcgccaagt
ccgagcaggacgactcggcaaggccacggcaaaatacttcttctactcgaac
atcatgaacttcttcaagaccgagatcaccctcgcgaacggcgagatccg
caagcgcccgctcatcgaaaccaacggcgagacgggcgagatcgtctggg
ataagggggattcgcgacggtccgcaaggtgctctccatgccgcaa
gtcaatatcgtgaaaaagaccgaggtccagaccgggcgggttcagcaagga
gtccatcctcccgaagcgcaactccgacaagctcatcgcgaggaagaagg
attgggacccgaaaaatatgcggcttcgacagcccgaccgtcgcatac
agcgtcctcgtcgtggcgaaggtggagaagggcaagtcaaagaagctcaa
gtccgtgaaggagctgctcgggatcacgattatgagcggtcctcctcg agaagaacccgatcgacttcctagaggccaagggatataaggaggtcaag
aaggacctgattattaaactgccgaagtactcgctcttcgagctggaaaa
cggccgcaagaggatgctcgcctccgcaggcgagttgcagaagggcaag
agctcgccctcccgagcaaatacgtcaatttcctgtacctcgctagccac
tatgaaaagctcaagggcagcccggaggacaacgagcagaagcagctctt
cgtggagcagcacaagcattacctggacgagatcatcgagcagatcagcg
agttctcgaagcgggtgatcctcgccgacgcgaacctggacaaggtgctg
tcggcatataacaagcaccgcgacaaaaccaatacgcggacaggccgaaaa
tatcatccacctcttcaccctcaccaacctcggcgctccggcagccttca
agtacttcgacaccacgattgaccggaagcggtacacgagcacgaaggag
gtgctcgatgcgacgctgatccaccagagcatcacagggctctatgaaac
acgcatcgacctgagccagctgggcggagacaagaagaagaagctcaagc
tctag SEQ ID NO: 2
*Streptococcus pyogenes* Cas9 encoded by SEQ ID NO: 1; with N- and C-terminal NLS sequences
MAPKKKRKVMDKKYSIGLDIGTNSVGWAVITDEYKVPSKKFKVLGNTDRH
SIKKNLIGALLFDSGETAEATRLKRTARRRYTRRKNRICYLQEIFSNEMA
KVDDSFFHRLEESFLVEEDKKHERHPIFGNIVDEVAYHEKYPTIYHLRKK
LVDSTDKADLRLIYLALAHMIKFRGHFLIEGDLNPDNSDVDKLFIQLVQT
YNQLFEENPINASGVDAKAILSARLSKSRRLENLIAQLPGEKKNGLFGNL
IALSLGLTPNFKSNFDLAEDAKLQLSKDTYDDDLDNLLAQIGDQYADLFL
AAKNLSDAILLSDILRVNTEITKAPLSASMIKRYDEHHQDLTLLKALVRQ
QLPEKYKEIFFDQSKNGYAGYIDGGASQEEFYKFIKPILEKMDGTEELLV
KLNREDLLRKQRTFDNGSIPHQIHLGELHAILRRQEDFYPFLKDNREKIE
KILTFRIPYYVGPLARGNSRFAWMTRKSEETITPWNFEEVVDKGASAQSF
IERMTNFDKNLPNEKVLPKHSLLYEYFTVYNELTKVKYVTEGMRKPAFLS
GEQKKAIVDLLFKTNRKVTVKQLKEDYFKKIECFDSVEISGVEDRFNASL
GTYHDLLKIIKDKDFLDNEENEDILEDIVLTLTLFEDREMIEERLKTYAH
LFDDKVMKQLKRRYTGWGRLSRKLINGIRDKQSGKTILDFLKSDGFANR
NFMQLIHDDSLTFKEDIQKAQVSGQGDSLHEHIANLAGSPAIKKGILQTV
KVVDELVKVMGRHKPENIVIEMARENQTTQKGQKNSRERMKRIEEGIKEL
GSQILKEHPVENTQLQNEKLYLYYLQNGRDMYVDQELDINRLSDYDVDHI
VPQSFLKDDSIDNKVLTRSDKNRGKSDNVPSEEVVKKMKNYWRQLLNAKL
ITQRKFDNLTKAERGGLSELDKAGFIKRQLVETRQITKHVAQILDSRMNT
KYDENDKLIREVKVITLKSKLVSDFRKDFQFYKVREINNYHHAHDAYLNA
VVGTALIKKYPKLESEFVYGDYKVYDVRKMIAKSEQEIGKATAKYFFYSN
IMNFFKTEITLANGEIRKRPLIETNGETGEIVWDKGRDFATVRKVLSMPQ
VNIVKKTEVQTGGFSKESILPKRNSDKLIARKKDWDPKKYGGFDSPTVAY
SVLVVAKVEKGKSKKLKSVKELLGITIMERSSFEKNPIDFLEAKGYKEVK
KDLIIKLPKYSLFELENGRKRMLASAGELQKGNELALPSKYVNFLYLASH
YEKLKGSPEDNEQKQLFVEQHKHYLDEIIEQISEFSKRVILADANLDKVL
SAYNKHRDKPIREQAENIIHLFTLTNLGAPAAFKYFDTTIDRKRYTSTKE
VLDATLIHQSITGLYETRIDLSQLGGDKKKKLKL SEQ ID NO: 3
Full U6 gene promoter sequence (not including transcription start site)
AAAAAACACTAGTAAGTACTTACTTATGTATTATTAACTACTTTAGCTAA
CTTCTGCAGTACTACCTAAGAGGCTAGGGGTAGTTTTATAGCAGACTTAT
AGCTATTATTTTTATTTAGTAAAGTGCTTTTAAAGTAAGGTCTTTTTTAT
AGCACTTTTTATTTATTAATATATATTATATAATAATTTTAAGCCTGG
AATAGTAAAGAGGCTTATATAATAATTTATAGTAATAAAAAGCTTAGCAGC
TGTAATATAATTCCTAAAGAAACAGCATGAAATGGTATTATGTAAGAGCT
ATAGTCTAAAGGCACTCTGCTGGATAAAAATAGTGGCTATAAGTCTGCTG
CAAAACTACCCCCAACCTCGTAGGTATATAAGTACTGTTTGATGGTAGTC
TATC SEQ ID NO: 4
Truncated/shorter U6 gene promoter sequence (not including transcription start site)
AATTCCTAAAGAAACAGCATGAAATGGTATTATGTAAGAGCTATAGTCTA
AAGGCACTCTGCTGGATAAAAATAGTGGCTATAAGTCTGCTGCAAAACTA
CCCCCAACCTCGTAGGTATATAAGTACTGTTTGATGGTAGTCTATC SEQ ID NO: 5
U6 gene intron
GTTCGTTTCGGCTTTTCCTCGGAACCCCCAGAGGTCATCAGTTCGAATCG
CTAACAG SEQ ID NO: 6
U6 gene transcriptional terminator sequence
TTTTTTTTCTCTT

SEQUENCES

SEQ ID NO: 7
Filamentous fungal cell Codon optimized
Streptococcus pyogenes Cas9-encoding gene; no NLS
atggacaagaagtacagcatcggcctcgacatcggcaccaactcggtggg
ctgggccgtcatcacggacgaatataaggtccccgtcgaagaagttcaagg
tcctcggcaatacagaccgccacagcatcaagaaaaacttgatcggcgcc
ctcctgttcgatagcggcgagaccgcggaggcgaccaggctcaagaggac
cgccaggagacggtactaggcgcaagaacaggatctgctacctgcagg
agatcttcagcaacgagatggcgaaggtggacgactccttcttccaccgc
ctggaggaatcattcctggtggaggaggacaagaagcatgagcggcaccc
aatcttcggcaacatcgtcgacgaggtggcctaccacgagaagtaccga
caatctaccacctccggaagaaacttggtggacagcagacaagggcgac
ctccggctcatctaccttgccctcgcgcatatgatcaagttccgcggcca
cttcctcatcgagggcgacctgaacccggacaactccgacgtggacaagc
tgttcatccagctcgtgcagacgtacaatcaactgttcgaggagaacccc
ataaacgctacgacgacgccttcctggcccagatgaggag
accagtacgcggaccctcttcctcgccgccaagaacctctccgacgtatc
ctgctcagcgacatccttcggtcaacaccgaaattaccaaggcaccgct
gtccgccagcatgattaaacgctacgacgagcaccatcaggacctcacgc
tgctcaaggcactcgtccgccagcagctccccgagaagtacaaggagatc
ttcttcgaccaatcaaaaaacggctacgcggatatatcgacggcggtgc
cagccaggaagagttctacaagttcatcaaaccaatcctggagaagatgg
acggcaccgaggagttgctggtcaagctcaacagggaggacctcctcagg
aagcaggaccgcttcgacaacggctccatccccgcatcagatccaccgtgg
cgaactgcatgccatccgtgggcgcaaggggacttctaccgttctga
aggataaccggggagaagatcgagaagatcttgacgttccgcatcccata
cacgtgggccgctggctcgcggcaactcccggttcgcctggatgaccca
gaagtcggaggagacctcacaccctggaactttgaggaggtggtcgata
agggcgctagcgctcagagcttcatcgagcgtgatgaccaacttcgataaa
aacctgcccaatgaaaaagtcctccccccaagcactcgctgctctacgagta
cttcaccgtgtacaacgagctcaccaaggtaaatacgtcaccgagggcat
gcggaagccggcgttcctgagcggcgagcagaagaaggcgatagtggacc
tcctcttcaagaccaacaggaagtgaccgtgaagcaattaaagaggcaac
tacttcaagaaaatagagtcgttcgactccgtggagatctcgggcgtgga
ggatcggttcaacgcctcactcggcacgtatcacgacctcctcaagatca
ttaaagacaaggacttcctcgacaacgaggagaacgaggacatcctcgag
gacatcgtcctcacccttgacctgttcgaggaccgcgaaatgatcgagga
ggctgaagacctacgcgcacctgttcgacgacaagtgcatgaaacagc
tcaagaggcgccgctacactggttgggaaggctgtcccgcaagctcatt
aatggcatcagggacaagcagagcggcaagaccatcctggacttcctcaa
gtccgacggttcgccaaccgcaacttcatgcagctcattcacgacgact
cgctcacgttcaaggaagacatccagaaggcacaggtgagcggcaggt
gactccctccacgaacacatcgccaacctggccggctcgccggccattaa
aaagggcatcctgcagacggtcaaggtcgtcgacgagctcgtgaaggtga
tgggccggcacaagcccgaaaatatcgtcatagagatggcgaggagaac
cagacacccaaaaaggcagaagaactcgcgcgagcggatgaaacggat
cgaggagggcattaaagagctcgggtccagatcctgaaggagcaccccg
tggaaaataccagctccagaatgaaaagtctacctctactacctgcag
aacggccgcgacatgtacgtggaccaggacgtggacattaatcggctatc
ggactacgacgtcgaccacatcgtgccgcagtcgttcctcaaggacgta
gcatcgacaacaaggtgctcacccggtcggataaaaatcggggcaagagc
gacaacgtgcccagcgaggaggtcgtgaagaagatgaaaaactactggcg
ccagctcctcaacgcgaaactgatcaccccagcgcaagttcgacaacctga
cgaaggcggaacgcggtggcttgagcgaactgtcaaggcgggcttcata
aaaaggcagctggtcgagcgcgcagatcacgaagcatgtcgcccgat
cctggacagccgcatgaatactaagtacgatgaaaacgacaagctgatcc
gggaggtgaaggtgatcacgctgaagtccaagtccgtgtcggacttccgc
aaggacttccagttctacaaggtccgcgagatcaacaactaccaccgc
ccacgacgctacctgaatgcggtggtcgggacggcctcgatcaagagt
acccgaagctggagtcggagttcgtgtacggcgactacaaggtctacga
gtgcgcaaaatgatcgccaagtccgagcaggagatcggcaaggccacggc
aaatacttcttctactcgaacatcatgaacttcttcaagaccgagatca
ccctcgccaacggcgagatccgcaagcgccctcatcgaaaccaacgga
gagacgggcgagatcgtctgggataagggccgggattcgcgacggtccg
caaggtgctctccatgccgcaagtcaatatcgtgaaaaagacggaggtcc
agacgggcgggttcagcaaggagtccatcctccccgaagcgcaactccgac
aagctcatcgcgaggaagaaggattgggaccggaaaaaatggcggctt
cgacagccgaccgtcgcatacgagcgtcctcgtcgtggcgaagtggaga
agggcaagtcaaagaagctcaagtccgtgaaggagctgctcgggatcacg
attatggagcggtcctccttcgagaagaacccgatcgacttcctagaggc
caagggcatataaggaggtcaagaaggacctgattattaaactgccgaagt
actcgctcttcgagctggaaaacgccgcaagaggatgctcgcctccgca
ggcgagttgcagaagggcaacgagctcgccctccccgagcaaatacgtcaa tttcctgtacctcgctagccactatgaaaagctcaagggcagcccggagg
acaacgagcagaagcagctcttcgtggagcagcacaagcattacctggac
gagatcatcgagcagatcagcgagttctcgaagcgggtgatcctcgccga
cgcgaacctggacaaggtgctgtcggcatataacaagcaccgcgacaaac
caatacgcgagcaggccgaaaatatcatccacctcttcaccctcaccaac
ctcggcgctccggcagccttcaagtacttcgacaccacgattgaccggaa
gcggtacacgagcacgaaggaggtgctcgatgcgacgctgatccaccaga
gcatcacagggctctatgaaacacgcatcgacctgagccagctgggcgga
gac SEQ ID NO: 8
Streptococcus pyogenes Cas9 encoded by SEQ ID
NO: 7; no NLS
MDKKYSIGLDIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVK
MGRHKPENIVIEMARENQTTQKGQKNSRERMKRIEEGIKELGSQILKEHP
VENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGD

SEQ ID NO: 9
SV40 NLS
PKKKRKV

SEQ NO: 10
T. reesei blr2 (blue light regulator 2) gene NLS
KKKKLKL

SEQ ID NO: 11
Streptococcus thermophilus LMD-9 Cas9
MTKPYSIGLDIGTNSVGWAVTTDNYKVPSKKMKVLGNTSKKYIKKNLLGV
LLFDSGITAEGRRLKRTARRRYTRRRNRILYLQEIFSTEMATLDDAFFQR
LDDSFLVPDDKRDSKYPIFGNLVEEKAYHDEFPTIYHLRKYLADSTKKAD
LRLVYLALAHMIKYRGHFLIEGEFNSKNNDIQKNFQDFLDTYNAIFESDL
SLENSKQLEEIVKDKISKLEKKDRILKLFPGEKNSGIFSEFLKLIVGNQA
DFRKCFNLDEKASLHFSKESYDEDLETLLGYIGDDYSDVFLKAKKLYDAI
LLSGFLTVTDNETEAPLSSAMIKRYNEHKEDLALLKEYIRNISLKTYNEV
FKDDTKNGYAGYIDGKTNQEDFYVYLKKLLAEFEGADYFLEKIDREDFLR
KQRTFDNGSIPYQIHLQEMRAILLDKQAKFYPFLAKNKERIEKILTFRIPY
YVGPLARGNSDFAWSIRKRNEKITPWNFEDVIDKESSAEAFINRMTSFDL
YLPEEKVLPKHSLLYETFNVYNELTKVRFIAESMRDYQFLDSKQKKDIVR
LYFKDKRKVTDKDIIIEYLHAIYGYDGIELKGIEKQFNSLSTYHDLLNII
NDKEFLDDSSNEAIIEEIIHTLTIFEDREMIKQRLSKFENIFDKSVLKKL
SRRHYTGWGKLSAKLINGIRDEKSGNTILDYLIDDGISNRNFMQLIHDDA
LSFKKKIQKAQIIGDEDKGNIKEVVKSLPGSPAIKKGILQSIKIVDELVK
VMGGRKPESIVVEMARENQYTNQGKSNSQQRLKRLEKSLKELGSKILKEN
IPAKLSKIDNNALQNDRLYLYYLQNGKDMYTGDDLDIDRLSNYDIDHIIP
QAFLKDNSIDNKVLVSSASNRGKSDDVPSLEVVKKRKTFWYQLLKSKLIS
QRKFDNLTKAERGGLSPEDKAGFIQRQLVETRQITKHVARLLDEKFNNKK
DENNRAVRTVKIITLKSTLVSQFRKDFELYKVREINDFHHAHDAYLNAVV
ASALLKKYPKLEPEFVYGDYPKYNSFRERKSATEKVYFYSNIMNIFKKSI
SLADGRVIERPLIEVNEETGESVWNKESDLATVRRVLSYPQVNVVKKVEE
QNHGLDRGKPKGLFNANLSSKPKPNSNENLVGAKEYLDPKKYGGYAGISN
SFTVLVKGTIEKGAKKKITNVLEFQGISILDRINYRKDKLNFLLEKGYKD
IELIIELPKYSLFELSDGSRRMLASILSTNNKRGEIHKGNQIFLSQKFVK LLYHAKRISNTINENHRKYVENHKKEFEELFYYILEFNENYVGAKKNGKL
LNSAFQSWQNHSIDELCSSFIGPTGSERKGLFELTSRGSAADFEFLGVKI
PRYRDYTPSSLLKDATLIHQSVTGLYETRIDLAKLGEG SEQ ID NO: 12
Streptococcus mutans UA159 Cas9
MKKPYSIGLDIGTNSVGWAVVTDDYKVPAKKMKVLGNTDKSHIEKNLLGA
LLFDSGNTAEDRRLKTARRRYTRRRNRILYLQEIFSEEMGKVDDSFFHR
LEDSFLVTEDKRGERHPIFGNLEEEVKYHENPPTIYHLRQYLADNPEKVD
LRLVYLALAHIIKFRGHFLIEGKFDTRNNDVQRLFQEFLAVYDNTFENSS
LQEQNVQVEEILTDKISKSAKKDRVLKLFPNEKSNGRFAEFLKLIVGNQA
DFKKHFELEEKAPLQFSKDTYEEELEVLLAQIGDNYAELFLSAKKLYDSI
LLSGILTVTDVGTKAPLSASMIQRYNEHQMDLAQLKQFIRQKLSDKYNEV
FSDVSKDGYAGYIDGKTNQEAFYKYLKGLLNKIEGSGYFLDKIEREDFLR
KQRTFDNGSIPHQIHLQEMRAIIRRQAEFYPPLADNQDRIEKLLTFRIPY
YVGPLARGKSDFAWLSRKSADKITPWNFDEIVDKESSAEAFINRMTNYDL
YLPNQKVLPKHSLLYEKFTVYNELTKVKYKTEQGKTAFFDANMKQEIFDG
VFKVYRKVTKDKLMDFLEKEFDEFRIVDLTGLDKENKVFNASYGTYHDLC
KILDKDFLDNSKNEKILEDIVLTLTLFEDREMIRKRLENYSDLLTKEQVK
KLERRHYTGWGRLSAELIHGIRNKESRKTILDYLIDDGNSNRNFMQLIND
DALSFKEEIAKAQVIGETDNLNQVVSDIAGSPAIKKGILQSLKIVDELVK
IMGHOPENIVVEMARENQFTNQGRRNSQQRLKGLTDSIKEFGSQILKEHP
VENSQLQNDRLFLYYLQNGRDMYTGEELDIDYLSQYDIDHIIPQAFIKDN
SIDNRVLTSSKENRGKSDDVPSKDVVRKMKSYWSKLLSAKLITQRKFDNL
TKAERGGLTDDDKAGFIKRQLVETRQITKHVARILDERFNTETEDNNKKI
RQVKIVTLKSNLVSNFRKEFELYKVREINDYHHAHDAYLNAVIGKALLGV
YPQLEPEFVYGDYPHFGHKENKATAKKFFYSNIMNFFKKDDVRTDKNGE
IIWKKDEHISNIKKVLSYPQVNIVKKVEEQTGGFSKESILPKGNSDKLIP
RKTKKFYWDTKKYGGFDSPIVAYSILVIADIEKGKSKKLKTVKALVGVTI
MEKMTFERDPVAFLERKGYRNVQEENIIKLPKYSLFKLENGRKRLLASAR
ELQKGNEIVLPNHLGTLLYHAKNIHKVDEPKHLDYVDKHKDEFKELLDVV
SNFSKKYTLAEGNLEKIKELYAQNNGEDLKELASSFINLLTFTAIGAPAT
FKFFDKNIDRKRYTSTTEILNATLIHQSITGLYETRIDLNKLGGD SEQ ID NO: 13
Campylobacter jejuni Cas9
MARILAFDIGISSIGWAFSENDELKDCGVRIFTKVENPKTGESLALPRRL
ARSARKRLARRKARLNHLKHLIANEFKLNYEDYQSFDESLAKAYKGSLIS
PYELRFRALNELLSKQDFARVILHIAKRRGYDDIKNSDDKEKGAILKAIK
QNEEKLANYQSVGEYLYKEYFQKFKENSKEFTNVRNKKESYERCIAQSFL
KDELKLIFKKQREFGFSFSKKFEEEVLSVAFYKRALKDFSHLVGNCSFFT
DEKRAPKNSPLAFMFVALTRIINLLNNLKNTEGILYTKDDLNALLNEVLK
NGTLTYKQTKKLLGLSDDYEFKGEKGTYFIEFKKYKEFIKALGEHNLSQD
DLNEIAKDITLIKDEIKLKKALAKYDLNQNQIDSLSKLEFKDHLNISFKA
LKLVTPLMLEGKKYDEACNELNLKVAINEDKKDFLPAFNETYYKDEVTNP
VVLRAIKEYRKVLNALLKKYGKVHKINIELAREVGKNHSQRAKIEKEQNE
NYKAKKDAELECEKLGLKINSKNILKLRLFKEQKEFCAYSGEKIKISDLQ
DEKMLEIDHIYPYSRSFDDSYMNKVLVFTKQNQEKLNQTPFEAFGNDSAK
WQKIEVLAKNLPTKKQKRILDKNQKEQKNFKDRNLNDTRYIARLVLNY
TKDYLDFLPLSDDENTKLNDTQKGSKVHVEAKSGMLTSALRHTWGFSAKD
RNNHLHHAIDAVIIAYANNSIVKAFSDFKKEQESNSAELYAKKISELDYK
NKRKFFEPFSGFRQKVLDKIDEIFVSKPERKKPSGALHEETFRKEEEFYQ
SYGGKEGVLKALELGKIRKVNGKIVKNGDMFRVDIFKHKKTNKFYAVPIY
TMDFALKVLPNKAVARSKKGEIKDWILMDENYEFCFSLYKDSLILIQTKD
MQEPEFVYYNAFTSSTVSLIVSKHDNKFETLSKNQKILFKNANEKEVIAK
SIGIQNLKVFEKYIVSALGEVTKAEFRQREDFKK SEQ ID NO: 14
Neisseria meningitides Cas9
MAAFKPNSINYILGLDIGIASVGWAMVEIDEEENPIRLIDLGVRVFERAE
VPKTGDSLAMARRLARSVRRLTRRRAHRLLRTRRLLKREGVLQAANFDEN
GLIKSLPNTPWQLRAAALDRKLTPLEWSAVLLHLIKHRGYLSQRKNEGET
ADKELGALLKGVAGNAHALQTGDFRTPAELALNKFEKESGHIRNQRSDYS
HTFSRKDLQAELILLFEKQKEFGNPHVSGGLKEGIETLLMTQRPALSGDA
VQKMLGHCTFEPAEPKAAKNTYTAERFIWLTKLNNLRILEQGSERPLTDT
ERATLMDEPYRKSKLTYAQARKLLGLEDTAPFKGLRYGNEAASTLMEM
KAYHAISRALEKEGLKDKKSPLNLSPELQDEIGTAFSLFKTDEDITGRLK
DRIQPEILEALLKHISFDKFVQISLKALRRIVPLMEQGKRYDEACAEIYG
DHYGKKNTEEKIYLPPIPADEIRNPVVLRALSQARKVINGVVRRYGSPAR
IHIETAREVGKSFKDRKEIEKRQEENRKDREKAAAKFREYFPNFVGEPKS
KDILKLRLYEQQHGKCLYSGKEINLGRLNEKGYVEIDHALPFSRTWDDSF
NNKVLVLGSENQNKGNQTPYEYFNGKDNSREWQEFKARVETSRFPNSKKQ
RILLQKFDEDGFKERNLNDTRYVNRFLCQFVADRMRLTGKGKKRVFASNG
QITNLLRGFWGLRKVRAENDRHHALDAVVVACSTVAMQQKITRFVRYKEM
NAFDGKTIDKETGEVLHQKTHFPQPWEFFAQEVMIRVFGKPDGKPEFEEA
DTLEKLRTLLAEKLSSSPEAVHEYVTPLFVSRAPNRKMSGQGHMETVKSA
KRLDEGVSVLRVPLTQLKLKDLEKMVNREREPKLYEALKARLEAHKDDPA KAFAEPFYKYDKAGNRTQQVKAVRVEQVQKTGVWVRNHNGIADNATMVRV
DVFEKGDKYYLVPIYSWQVAKGILPDRAVVQGKDEEDWQLIDDSFNFKFS
LHPNDLVEVITKKARMFGYFASCHRGTGNINIRIHDLDHKIGKNGILEGI
GVKTALSFQKYQIDELGKEIRPCRLKKRPPVR SEQ ID NO: 15
Francisella tularensis subsp. novicida Cas9
MNFKILPIAIDLGVKNTGVFSAFYQKGTSLERLDNKNGKVYELSKDSYTL
LMNNRTARRHQRRGIDRKQLVKRLFKLIWTEQLNLEWDKDTQQAISFLFN
RRGFSFITDGYSPEYLNIVPEQVKAILMDIFDDYNGEDDLDSYLKLATEQ
ESKISEIYNKLMQKILEFKLMKLCTDIKDDKVSTKTLKEITSYEFELLAD
YLANYSESLKTQKFSYTDKQGNLKELSYYHHDKYNIQEFLKRHATINDRI
LDTLLTDDLDIWNFNFEKFDFDKNEEKLQNQEDKDHIQAHLHHFVFAVNK
IKSEMASSGGRHRSQYFQEITNVLDENNHQEGYLKNFCENLHNKKYSNLSV
KNLVNLIGNLSNLELKPLRKYFNDKIHAKADHWDEQKFTETYCHWILGEW
RVGVKDQDKKDGAKYSYKDLCNELKQKVTKAGLVDFLLELDPCRTIPPYL
DNNNRKPPKCQSLILNPKFLDNQYPNWQQYLQELKKLQSIQNYLDSFETD
LKVLKSSKDOPYFVEYKSSNQQ1ASGQRDYKDLDARILQFIFDRVKASDE
LLLNEIYFQAKKLKQKASSELEKLESSKKLDEVIANSQLSQILKSQHTNG
IFEQGTFLHLVCKYYKQRQRARDSRLYIMPEYRYDKKLHKYNNTGRFDDD
NQLLTYCNHKPRQKRYQLLNDLAGVLQVSPNFLKDKIGSDDDLFISKWLV
EHIRGFKKACEDSLKIQKDNRGLLNHKINIARNTKGKCEKEIFNLICKIE
GSEDKKGNYKHGLAYELGVLLFGEPNEASKPEFDRKIKKFNSIYSFAQIQ
QIAFAERKGNANTCAVCSADNAHRMQQIKITEPVEDNKDKIILSAKAQRL
PAIPTRIVDGAVKKMATILAKNIVDDNWQNIKQVLSAKHQLHIPIITESN
AFEFEPALADVKGKSLDRRKKALERISPENIFKDKNNRIKEFAKGISAY
SGANLTDGDFDGAKEELDHIIPRSHKKYGTLNDEANLICVTRGDNKNKGN
RIFCLRDLADKVFLKQFETTDDLEIEKKIADTIWDANKKDFKFGNYRSFI
NLTPQEQKAFRHALFLADENPIKQAVIRAINNRNRTFVNGTQRYFAEVLA
NNIYLRAKKENLNTDKISFDYFGIPTIGNGRGIAEIRQLYEKVDSDIQAY
AKGDKPQASYSHLIDAMLAFCIAADEHRNDGSIGLEIDKNYSLYPLDKNT
GEVFTKDIFSQIKITDNEFSDKKLVRKKAIEGFNTHRQMTRDGIYAENYL
PILIHKELNEVRKGYTWKNSEEIKIFKGKKYDIQQLNNLVYCLKFVDKPI
SIDIQISTLEELRNILTTNNIAATAEYYYINLKTQKLHEYYIENYNTALG
YKKYSKEMEFLRSLAYRSERVKIKSIDDVKQVLDKDSNFIIGKITLPFKK
EWQRLYREWQNTTIKDDYEFLKSFFNVKSITKLHKKVRKDFSLPISTNEG
KFLVKRKTWDNNFIYQILNDSDSRADGTKPFIPAFDISKNEIVEAAIIDSF
TSKNIFWLPKNIELQKVDNKNIFAIDTSKWFEVETPSDLRDIGIATIQYK
IDNNSRPKVRVKLDYVIDDDSKINYFMNHSLLKSRYPDKVLEILKQSTII
EFESSGFNKTIKEMLGMKLAGIYNETSNN SEQ ID NO: 16
Pasteurella multocida Cas9
MQTTNLSYILGLDLGIASVGWAVVEINENEDPIGLIDVGVRIFERAEVPK
TGESLALSRRLARSTRRLIRRRAHRLLLAKRFLKREGILSTIDLEKGLPN
QAWELRVAGLERRLSAIEWGAVLLHLIKHRGYLSKRKNESQTNNKELGAL
LSGVAQNHQLLQSDDYRTPAELALKKFAKEEGHIRNQRGAYTHTFNRLDL
LAELNLLFAQQHQFGNPHCKEHIQQYMTELLMWQKPALSGEAILKMLGKC
THEKNEFKAAKHTYSAERFVWLTKLNNLRILEDGAERALNEEERQLLINH
PYEKSKLTYAQVRKLLGLSEQAIFKHLRYSKENAESATFMELKAWHAIRK
ALENQGLKDTWQDLAKKPDLLDEIGTAFSLYKTDEDIQQYLTNKVPNSVI
NALLVSLNFDKFIELSLKSLRKILPLMEQGKRYDQACREIYGHHYGEANQ
KTSQLLPAIPAQEIRNPVVLRTLSQARKVINAIIRQYGSPARVHIETGRE
LGKSFKERREIQKQQEDNRTKRESAVQKPKELFSDFSSEPKSKDILKFRL
YEQQHGKCLYSGKEINIHRLNEKGYVEIDHALPFSRTWDDSFNNKVLVLA
SENQNKGNQTPYEWLQGKINSERWKNFVALVLGSQCSAAKKQRLLTQVID
DNKFIDRNLNDTRYIARFLSNYIQENLLLVGKNKKNVFTPNGQITALLRS
RWGLIKARENNNRHHALDAIVVACATPSMQQKITRFIRFKEVHPYKIENR
YEMVDQESGEIISPHFPEPWAYFRQEVNIVFDHNPDTVLKEMLPDRPQA
NHQFVQPLFVSRAPTRKMSGQGHMETIKSAKRLAEGISVLRIPLTQLKPN
LLENMVNKEREPALYAGLKARLAEFNQDPAKAFATPFYKQGGQQVKAIRV
EQVQKSGVLVRENNGVADNASIVRTDVFIKNNKFFLVPIYTWQVAKGILP
NKAIVAHKNEDEWEEMDEGAKFKFSLFPNDLVELKTKKEYFFGYYIGLDR
ATGNISLKEHDGEISKGKDGVYRVGVKLALSFEKYQVDELGKNRQICRPQ
QRQPVR SEQ ID NO: 17
sgRNA: gAd3A TS1
guccucgagcaaaaggugccGUUUUAGAGCUAGAAAUAGCAAGUUAAAAU
AAGGCUAGUCCGUUAUCAACUUGAAAAAGUGGCACCGAGUCGGUGGUGC.

SEQ ID NO: 18
sgRNA: gTrGA TS2
guucagugcaauaggcgucGUUUUAGAGCUAGAAAUAGCAAGUUAAAAU
AAGGCUAGUCCGUUAUCAACUUGAAAAAGUGGCACCGAGUCGGUGGUGC

| SEQUENCES |
| --- |
| SEQ ID NO: 19<br>sgRNA: gTrGA TS11<br>gccaauggcgacggcagcacGUUUUAGAGCUAGAAAUAGCAAGUUAAAAU<br>AAGGCUAGUCCGUUAUCAACUUGAAAAAGUGGCACCGAGUCGGUGGUGC |

| SEQUENCES |
| --- |
| SEQ ID NO: 20<br>sgRNA: gPyr2 TS6<br>gcacagcgggaugcccuuguGUUUUAGAGCUAGAAAUAGCAAGUUAAAAU<br>AAGGCUAGUCCGUUAUCAACUUGAAAAAGUGGCACCGAGUCGGUGGUGC |

That which is claimed:

1. A method for homologous recombination of a donor DNA with a genomic locus in a *Trichoderma* sp. cell; the method comprising:

(a) generating a heterokaryon between a helper *Trichoderma* species (sp.) strain and a target *Trichoderma* sp. strain, wherein the helper *Trichoderma* sp. strain comprises an expression construct that silences the non-homologous end joining (NHEJ) mechanism, wherein the expression construct silences one or more of: ku80, ku70 and liq 4:

(b) introducing a donor DNA into the heterokaryon, wherein the donor DNA comprises a region of homology to a genomic locus in the target strain sufficient for homologous recombination at the genomic locus;

(c) generating and plating spores from the heterokaryon cells of (b); and, (d) identifying cells from the plated spores in which (i) the donor DNA has integrated into the genome by homologous recombination at the genomic locus, and (ii) the expression construct that silences the non-homologous end joining (NHEJ) mechanism is not present.

2. The method of claim 1, further comprising introducing a functional Cas/guide RNA complex into the heterokaryon, wherein the Cas/guide RNA complex has a target site within the genomic locus.

3. The method of claim 2, wherein the Cas is a Cas nickase.

4. The method of claim 1, wherein the donor DNA comprises a polynucleotide sequence of interest, wherein homologous recombination at the genomic locus results in insertion of the polynucleotide sequence of interest in the genomic locus.

5. The method of claim 2, wherein the Cas is a Cas9 endonuclease or variant thereof.

6. The method of claim 5, wherein the Cas9 endonuclease or variant thereof comprises a full length Cas9 or a functional fragment thereof from a cell type selected from the group consisting of: *Streptococcus* sp., *S. pyogenes*, *S. mutans*, *S. thermophiles*, *Campylobacter* sp., *C. jejuni*, *Neisseria* sp., *N. meningitides*, *Francisella* sp., *F. novicida*, *Pasteurella* sp., and *P. multocida*.

7. The method of claim 1, wherein introducing the functional Cas/guide RNA complex into the heterokaryon comprises introducing a DNA construct comprising an expression cassette for the Cas endonuclease into the *Trichoderma* sp. cells.

8. The method of claim 1, wherein introducing the functional Cas/guide RNA complex into the heterokaryon comprises introducing a DNA construct comprising an expression cassette for the guide RNA into the *Trichoderma* sp. cells.

9. The method of claim 1, wherein the introducing step comprises directly introducing the Cas endonuclease into the *Trichoderma* sp. cells.

10. The method of claim 1, wherein the introducing step comprises directly introducing the guide RNA into the *Trichoderma* sp. cells.

11. The method of claim 1, wherein the *Trichoderma* sp. is *Trichoderma reesei*.

12. The method of claim 1, wherein the donor DNA has partially integrated into the genome at the genomic locus.

13. The method of claim 1, wherein integration of the donor DNA results in a modification of the genomic locus.

14. The method of claim 13, wherein the modification is selected from the group consisting of a deletion of one or more nucleotides, an insertion of one or more nucleotides, insertion of an expression cassette encoding a protein of interest, a substitution of one or more nucleotides, and any combination thereof.

15. The method of claim 1, wherein the identifying step comprises culturing cells grown from the spores from step (c) under conditions to select for or screen for the integration of the donor DNA at the genomic locus or the modification of the genomic locus.

* * * * *

SEQUENCE LISTING

<160> NUMBER OF SEQ ID NOS: 20

<210> SEQ ID NO 1
<211> LENGTH: 4155
<212> TYPE: DNA
<213> ORGANISM: Artificial Sequence
<220> FEATURE:
<223> OTHER INFORMATION: Streptococcus pyogenes Cas9-encoding gene

<400> SEQUENCE: 1

```
atggcaccga agaagaagcg caaggtgatg gacaagaagt acagcatcgg cctcgacatc      60
ggcaccaact cggtgggctg gccgtcatc acggacgaat ataaggtccc gtcgaagaag      120
ttcaaggtcc tcggcaatac agaccgccac agcatcaaga aaaacttgat cggcgccctc      180
ctgttcgata gcggcgagac cgcggaggcg accaggctca agaggaccgc caggagacgg      240
tacactaggc gcaagaacag gatctgctac ctgcaggaga tcttcagcaa cgagatggcg      300
aaggtggacg actccttctt ccaccgcctg gaggaatcat tcctggtgga ggaggacaag      360
aagcatgagc ggcaccccaat cttcggcaac atcgtcgacg aggtggccta ccacgagaag      420
tacccgacaa tctaccacct ccggaagaaa ctggtggaca gcacagacaa ggcggacctc      480
cggctcatct accttgccct cgcgcatatg atcaagttcc gcggccactt cctcatcgag      540
ggcgacctga acccggacaa ctccgacgtg acaagctgt catccagct cgtgcagacg      600 tacaatcaac tgttcgagga aaaccccata aacgctagcg gcgtggacgc caaggccatc      660
ctctcggcca ggctctcgaa atcaagaagg ctggagaacc ttatcgcgca gttgccaggc      720
gaaaagaaga acggcctctt cggcaacctt attgcgctca gcctcggcct gacgccgaac      780
ttcaaatcaa acttcgacct cgcggaggac gccaagctcc agctctcaaa ggacacctac      840
gacgacgacc tcgacaacct cctggcccag ataggagacc agtacgcgga cctcttcctc      900
gccgccaaga acctctccga cgctatcctg ctcagcgaca tccttcgggt caacaccgaa      960
attaccaagg caccgctgtc cgccagcatg attaaacgct acgacgagca ccatcaggac     1020
ctcacgctgc tcaaggcact cgtccgccag cagctccccg agaagtacaa ggagatcttc     1080
ttcgaccaat caaaaaacgg ctacgcggga tatatcgacg gcggtgccag ccaggaagag     1140
ttctacaagt tcatcaaacc aatcctggag aagatggacg gcaccgagga gttgctggtc     1200
aagctcaaca gggaggacct cctcaggaag cagaggacct cgacaacgg ctccatcccg     1260 catcagatcc acctgggcga actgcatgcc atcctgcggc gccaggagga cttctacccg     1320
ttcctgaagg ataaccggga gaagatcgag aagatcttga cgttccgcat cccatactac     1380
gtgggcccgc tggctcgcgg caactcccgg ttcgcctgga tgacccggaa gtcggaggag     1440
accatcacac cctggaactt tgaggaggtg gtcgataagg gcgctagcgc tcagagcttc     1500
atcgagcgca tgaccaactt cgataaaaac ctgcccaatg aaaaagtcct ccccaagcac     1560
tcgctgctct acgagtactt caccgtgtac aacgagctca ccaaggtcaa atacgtcacc     1620
gagggcatgc ggaagccggc gttcctgagc ggcgagcaga agaaggcgat agtggaccct     1680
```

```
ctcttcaaga ccaacaggaa ggtgaccgtg aagcaattaa aagaggacta cttcaagaaa    1740
atagagtgct tcgactccgt ggagatctcg ggcgtggagg atcggttcaa cgcctcactc    1800
ggcacgtatc acgacctcct caagatcatt aaagacaagg acttcctcga caacgaggag    1860
aacgaggaca tcctcgagga catcgtcctc accctgaccc tgttcgagga ccgcgaaatg    1920
atcgaggaga ggctgaagac ctacgcgcac ctgttcgacg acaaggtcat gaaacagctc    1980
aagaggcgcc gctacactgg ttggggaagg ctgtcccgca agctcattaa tggcatcagg    2040
gacaagcaga gcggcaagac catcctggac ttcctcaagt ccgacgggtt cgccaaccgc    2100
aacttcatgc agctcattca cgacgactcg ctcacgttca aggaagacat ccagaaggca    2160
caggtgagcg ggcagggtga ctccctccac gaacacatcg ccaacctggc cggctcgccg    2220
gccattaaaa agggcatcct gcagacggtc aaggtcgtcg acgagctcgt gaaggtgatg    2280
ggccggcaca agcccgaaaa tatcgtcata gagatggcca gggagaacca gaccacccaa    2340
aaagggcaga agaactcgcg cgagcggatg aaacggatcg aggagggcat taaagagctc    2400
gggtcccaga tcctgaagga gcaccccgtg gaaaataccc agctccagaa tgaaaagctc    2460
tacctctact acctgcagaa cggccgcgac atgtacgtgg accaggagct ggacattaat    2520
cggctatcgg actacgacgt cgaccacatc gtgccgcagt cgttcctcaa ggacgatagc    2580
atcgacaaca aggtgctcac ccggtcggat aaaaatcggg gcaagagcga caacgtgccc    2640
agcgaggagg tcgtgaagaa gatgaaaaac tactggcgcc agctcctcaa cgcgaaactg    2700
atcacccagc gcaagttcga caacctgacg aaggcggaac gcggtggctt gagcgaactc    2760
gataaggcgg gcttcataaa aaggcagctg gtcgagacgc gccagatcac gaagcatgtc    2820
gcccagatcc tggacagccg catgaatact aagtacgatg aaaacgacaa gctgatccgg    2880
gaggtgaagg tgatcacgct gaagtccaag ctcgtgtcgg acttccgcaa ggacttccag    2940
ttctacaagg tccgcgagat caacaactac caccacgccc acgacgccta cctgaatgcg    3000
gtggtcgggc cgcccctgat caagaagtac ccgaagctgg agtcggagtt cgtgtacggc    3060
gactacaagg tctacgacgt gcgcaaaatg atcgccaagt ccgagcagga gatcggcaag    3120
gccacggcaa atacttcttc tactcgaac atcatgaact tcttcaagac cgagatcacc    3180
ctcgcgaacg gcgagatccg caagcgcccg ctcatcgaaa ccaacggcga cgggcgag    3240 atcgtctggg ataagggccg ggatttcgcg acgtccgca aggtgctctc catgccgcaa    3300
gtcaatatcg tgaaaaagac ggaggtccag acgggcgggt tcagcaagga gtccatcctc    3360
ccgaagcgca actccgacaa gctcatcgcg aggaagaagg attgggaccc gaaaaaatat    3420
ggcggcttcg acagcccgac cgtcgcatac agcgtcctcg tcgtggcgaa ggtggagaag    3480
ggcaagtcaa agaagctcaa gtccgtgaag gagctgctcg ggatcacgat tatgagcgg    3540 tcctccttcg agaagaaccc gatcgacttc ctagaggcca agggatataa ggaggtcaag    3600
aaggacctga ttattaaact gccgaagtac tcgctcttcg agctgaaaaa cggccgcaag    3660
aggatgctcg cctccgcagg cgagttgcag aagggcaacg agctcgccct cccgagcaaa    3720
tacgtcaatt tcctgtacct cgctagccac tatgaaaagc tcaagggcag cccggaggac    3780
aacgagcaga agcagctctt cgtggagcag cacaagcatt acctgacgga gatcatcgag    3840
cagatcagcg agttctcgaa gcgggtgatc ctcgccgacg cgaacctgga caaggtgctg    3900
tcggcatata caaagcaccg cgacaaacca atacgcgagc aggccgaaaa tatcatccac    3960
ctcttcaccc tcaccaacct cggcgctccg gcagccttca gtacttcga caccacgatt    4020 gaccggaagc ggtacacgag cacgaaggag gtgctctgatg cgacgctgat ccaccagagc    4080
```

```
atcacagggc tctatgaaac acgcatcgac ctgagccagc tgggcggaga caagaagaag      4140
aagctcaagc tctag                                                       4155
```

<210> SEQ ID NO 2
<211> LENGTH: 1384
<212> TYPE: PRT
<213> ORGANISM: Artificial Sequence
<220> FEATURE:
<223> OTHER INFORMATION: Streptococcus pyogenes Cas9 Codon optimized
      sequence

<400> SEQUENCE: 2

```
Met Ala Pro Lys Lys Lys Arg Lys Val Met Asp Lys Lys Tyr Ser Ile
1               5                   10                  15

Gly Leu Asp Ile Gly Thr Asn Ser Val Gly Trp Ala Val Ile Thr Asp
            20                  25                  30

Glu Tyr Lys Val Pro Ser Lys Lys Phe Lys Val Leu Gly Asn Thr Asp
        35                  40                  45

Arg His Ser Ile Lys Lys Asn Leu Ile Gly Ala Leu Leu Phe Asp Ser
    50                  55                  60

Gly Glu Thr Ala Glu Ala Thr Arg Leu Lys Arg Thr Ala Arg Arg Arg
65                  70                  75                  80

Tyr Thr Arg Arg Lys Asn Arg Ile Cys Tyr Leu Gln Glu Ile Phe Ser
                85                  90                  95

Asn Glu Met Ala Lys Val Asp Asp Ser Phe Phe His Arg Leu Glu Glu
            100                 105                 110

Ser Phe Leu Val Glu Glu Asp Lys Lys His Glu Arg His Pro Ile Phe
        115                 120                 125

Gly Asn Ile Val Asp Glu Val Ala Tyr His Glu Lys Tyr Pro Thr Ile
    130                 135                 140

Tyr His Leu Arg Lys Lys Leu Val Asp Ser Thr Asp Lys Ala Asp Leu
145                 150                 155                 160

Arg Leu Ile Tyr Leu Ala Leu Ala His Met Ile Lys Phe Arg Gly His
                165                 170                 175

Phe Leu Ile Glu Gly Asp Leu Asn Pro Asp Asn Ser Asp Val Asp Lys
            180                 185                 190

Leu Phe Ile Gln Leu Val Gln Thr Tyr Asn Gln Leu Phe Glu Glu Asn
        195                 200                 205

Pro Ile Asn Ala Ser Gly Val Asp Ala Lys Ala Ile Leu Ser Ala Arg
    210                 215                 220

Leu Ser Lys Ser Arg Arg Leu Glu Asn Leu Ile Ala Gln Leu Pro Gly
225                 230                 235                 240

Glu Lys Lys Asn Gly Leu Phe Gly Asn Leu Ile Ala Leu Ser Leu Gly
                245                 250                 255

Leu Thr Pro Asn Phe Lys Ser Asn Phe Asp Leu Ala Glu Asp Ala Lys
            260                 265                 270

Leu Gln Leu Ser Lys Asp Thr Tyr Asp Asp Asp Leu Asp Asn Leu Leu
        275                 280                 285

Ala Gln Ile Gly Asp Gln Tyr Ala Asp Leu Phe Leu Ala Ala Lys Asn
    290                 295                 300

Leu Ser Asp Ala Ile Leu Leu Ser Asp Ile Leu Arg Val Asn Thr Glu
305                 310                 315                 320

Ile Thr Lys Ala Pro Leu Ser Ala Ser Met Ile Lys Arg Tyr Asp Glu
                325                 330                 335
```

-continued

His His Gln Asp Leu Thr Leu Leu Lys Ala Leu Val Arg Gln Gln Leu
            340                 345                 350

Pro Glu Lys Tyr Lys Glu Ile Phe Phe Asp Gln Ser Lys Asn Gly Tyr
        355                 360                 365

Ala Gly Tyr Ile Asp Gly Gly Ala Ser Gln Glu Glu Phe Tyr Lys Phe
    370                 375                 380

Ile Lys Pro Ile Leu Glu Lys Met Asp Gly Thr Glu Glu Leu Leu Val
385                 390                 395                 400

Lys Leu Asn Arg Glu Asp Leu Leu Arg Lys Gln Arg Thr Phe Asp Asn
                405                 410                 415

Gly Ser Ile Pro His Gln Ile His Leu Gly Glu Leu His Ala Ile Leu
            420                 425                 430

Arg Arg Gln Glu Asp Phe Tyr Pro Phe Leu Lys Asp Asn Arg Glu Lys
        435                 440                 445

Ile Glu Lys Ile Leu Thr Phe Arg Ile Pro Tyr Tyr Val Gly Pro Leu
    450                 455                 460

Ala Arg Gly Asn Ser Arg Phe Ala Trp Met Thr Arg Lys Ser Glu Glu
465                 470                 475                 480

Thr Ile Thr Pro Trp Asn Phe Glu Glu Val Val Asp Lys Gly Ala Ser
                485                 490                 495

Ala Gln Ser Phe Ile Glu Arg Met Thr Asn Phe Asp Lys Asn Leu Pro
            500                 505                 510

Asn Glu Lys Val Leu Pro Lys His Ser Leu Leu Tyr Glu Tyr Phe Thr
        515                 520                 525

Val Tyr Asn Glu Leu Thr Lys Val Lys Tyr Val Thr Glu Gly Met Arg
    530                 535                 540

Lys Pro Ala Phe Leu Ser Gly Glu Gln Lys Lys Ala Ile Val Asp Leu
545                 550                 555                 560

Leu Phe Lys Thr Asn Arg Lys Val Thr Val Lys Gln Leu Lys Glu Asp
                565                 570                 575

Tyr Phe Lys Lys Ile Glu Cys Phe Asp Ser Val Glu Ile Ser Gly Val
            580                 585                 590

Glu Asp Arg Phe Asn Ala Ser Leu Gly Thr Tyr His Asp Leu Leu Lys
        595                 600                 605

Ile Ile Lys Asp Lys Asp Phe Leu Asp Asn Glu Glu Asn Glu Asp Ile
    610                 615                 620

Leu Glu Asp Ile Val Leu Thr Leu Thr Leu Phe Glu Asp Arg Glu Met
625                 630                 635                 640

Ile Glu Glu Arg Leu Lys Thr Tyr Ala His Leu Phe Asp Asp Lys Val
                645                 650                 655

Met Lys Gln Leu Lys Arg Arg Arg Tyr Thr Gly Trp Gly Arg Leu Ser
            660                 665                 670

Arg Lys Leu Ile Asn Gly Ile Arg Asp Lys Gln Ser Gly Lys Thr Ile
        675                 680                 685

Leu Asp Phe Leu Lys Ser Asp Gly Phe Ala Asn Arg Asn Phe Met Gln
    690                 695                 700

Leu Ile His Asp Asp Ser Leu Thr Phe Lys Glu Asp Ile Gln Lys Ala
705                 710                 715                 720

Gln Val Ser Gly Gln Gly Asp Ser Leu His Glu His Ile Ala Asn Leu
                725                 730                 735

Ala Gly Ser Pro Ala Ile Lys Lys Gly Ile Leu Gln Thr Val Lys Val
            740                 745                 750

```
Val Asp Glu Leu Val Lys Val Met Gly Arg His Lys Pro Glu Asn Ile
            755                 760                 765

Val Ile Glu Met Ala Arg Glu Asn Gln Thr Thr Gln Lys Gly Gln Lys
770                 775                 780

Asn Ser Arg Glu Arg Met Lys Arg Ile Glu Glu Gly Ile Lys Glu Leu
785                 790                 795                 800

Gly Ser Gln Ile Leu Lys Glu His Pro Val Glu Asn Thr Gln Leu Gln
                805                 810                 815

Asn Glu Lys Leu Tyr Leu Tyr Tyr Leu Gln Asn Gly Arg Asp Met Tyr
            820                 825                 830

Val Asp Gln Glu Leu Asp Ile Asn Arg Leu Ser Asp Tyr Asp Val Asp
            835                 840                 845

His Ile Val Pro Gln Ser Phe Leu Lys Asp Asp Ser Ile Asp Asn Lys
            850                 855                 860

Val Leu Thr Arg Ser Asp Lys Asn Arg Gly Lys Ser Asp Asn Val Pro
865                 870                 875                 880

Ser Glu Glu Val Val Lys Lys Met Lys Asn Tyr Trp Arg Gln Leu Leu
                885                 890                 895

Asn Ala Lys Leu Ile Thr Gln Arg Lys Phe Asp Asn Leu Thr Lys Ala
            900                 905                 910

Glu Arg Gly Gly Leu Ser Glu Leu Asp Lys Ala Gly Phe Ile Lys Arg
            915                 920                 925

Gln Leu Val Glu Thr Arg Gln Ile Thr Lys His Val Ala Gln Ile Leu
            930                 935                 940

Asp Ser Arg Met Asn Thr Lys Tyr Asp Glu Asn Asp Lys Leu Ile Arg
945                 950                 955                 960

Glu Val Lys Val Ile Thr Leu Lys Ser Lys Leu Val Ser Asp Phe Arg
                965                 970                 975

Lys Asp Phe Gln Phe Tyr Lys Val Arg Glu Ile Asn Asn Tyr His His
            980                 985                 990

Ala His Asp Ala Tyr Leu Asn Ala Val Val Gly Thr Ala Leu Ile Lys
            995                 1000                1005

Lys Tyr Pro Lys Leu Glu Ser Glu Phe Val Tyr Gly Asp Tyr Lys
    1010                1015                1020

Val Tyr Asp Val Arg Lys Met Ile Ala Lys Ser Glu Gln Glu Ile
    1025                1030                1035

Gly Lys Ala Thr Ala Lys Tyr Phe Phe Tyr Ser Asn Ile Met Asn
    1040                1045                1050

Phe Phe Lys Thr Glu Ile Thr Leu Ala Asn Gly Glu Ile Arg Lys
    1055                1060                1065

Arg Pro Leu Ile Glu Thr Asn Gly Glu Thr Gly Glu Ile Val Trp
    1070                1075                1080

Asp Lys Gly Arg Asp Phe Ala Thr Val Arg Lys Val Leu Ser Met
    1085                1090                1095

Pro Gln Val Asn Ile Val Lys Lys Thr Glu Val Gln Thr Gly Gly
    1100                1105                1110

Phe Ser Lys Glu Ser Ile Leu Pro Lys Arg Asn Ser Asp Lys Leu
    1115                1120                1125

Ile Ala Arg Lys Lys Asp Trp Asp Pro Lys Lys Tyr Gly Gly Phe
    1130                1135                1140

Asp Ser Pro Thr Val Ala Tyr Ser Val Leu Val Val Ala Lys Val
    1145                1150                1155
```

| | | | | | | | | | | |
|---|---|---|---|---|---|---|---|---|---|---|
|Glu|Lys|Gly|Lys|Ser|Lys|Lys|Leu|Lys|Ser|Val|Lys|Glu|Leu|Leu|
| |1160| | | |1165| | | |1170| | | | | |

Gly Ile Thr Ile Met Glu Arg Ser Ser Phe Glu Lys Asn Pro Ile
    1175            1180                1185

Asp Phe Leu Glu Ala Lys Gly Tyr Lys Glu Val Lys Lys Asp Leu
    1190            1195                1200

Ile Ile Lys Leu Pro Lys Tyr Ser Leu Phe Glu Leu Glu Asn Gly
    1205            1210                1215

Arg Lys Arg Met Leu Ala Ser Ala Gly Glu Leu Gln Lys Gly Asn
    1220            1225                1230

Glu Leu Ala Leu Pro Ser Lys Tyr Val Asn Phe Leu Tyr Leu Ala
    1235            1240                1245

Ser His Tyr Glu Lys Leu Lys Gly Ser Pro Glu Asp Asn Glu Gln
    1250            1255                1260

Lys Gln Leu Phe Val Glu Gln His Lys His Tyr Leu Asp Glu Ile
    1265            1270                1275

Ile Glu Gln Ile Ser Glu Phe Ser Lys Arg Val Ile Leu Ala Asp
    1280            1285                1290

Ala Asn Leu Asp Lys Val Leu Ser Ala Tyr Asn Lys His Arg Asp
    1295            1300                1305

Lys Pro Ile Arg Glu Gln Ala Glu Asn Ile Ile His Leu Phe Thr
    1310            1315                1320

Leu Thr Asn Leu Gly Ala Pro Ala Ala Phe Lys Tyr Phe Asp Thr
    1325            1330                1335

Thr Ile Asp Arg Lys Arg Tyr Thr Ser Thr Lys Glu Val Leu Asp
    1340            1345                1350

Ala Thr Leu Ile His Gln Ser Ile Thr Gly Leu Tyr Glu Thr Arg
    1355            1360                1365

Ile Asp Leu Ser Gln Leu Gly Gly Asp Lys Lys Lys Leu Lys
    1370            1375                1380

Leu

<210> SEQ ID NO 3
<211> LENGTH: 404
<212> TYPE: DNA
<213> ORGANISM: Artificial Sequence
<220> FEATURE:
<223> OTHER INFORMATION: Full U6 gene promoter sequence

<400> SEQUENCE: 3
aaaaaacact agtaagtact tacttatgta ttattaacta ctttagctaa cttctgcagt    60
actacctaag aggctagggg tagttttata gcagacttat agctattatt tttatttagt   120
aaagtgcttt taaagtaagg tcttttttat agcactttt atttattata atatatatta   180
tataataatt ttaagcctgg aatagtaaag aggcttatat aataatttat agtaataaaa   240
gcttagcagc tgtaatataa ttcctaaaga aacagcatga aatggtatta tgtaagagct   300
atagtctaaa ggcactctgc tggataaaaa tagtggctat aagtctgctg caaaactacc   360
cccaaccctcg taggtatata agtactgttt gatggtagtc tatc                   404

<210> SEQ ID NO 4
<211> LENGTH: 146
<212> TYPE: DNA
<213> ORGANISM: Artificial Sequence
<220> FEATURE:
<223> OTHER INFORMATION: truncated/shorter U6 gene promoter sequence

<400> SEQUENCE: 4
aattcctaaa gaaacagcat gaaatggtat tatgtaagag ctatagtcta aaggcactct      60
gctggataaa aatagtggct ataagtctgc tgcaaaacta cccccaacct cgtaggtata     120
taagtactgt ttgatggtag tctatc                                          146

<210> SEQ ID NO 5
<211> LENGTH: 57
<212> TYPE: DNA
<213> ORGANISM: Artificial Sequence
<220> FEATURE:
<223> OTHER INFORMATION: U6 gene intron

<400> SEQUENCE: 5
gttcgtttcg gcttttcctc ggaaccccca gaggtcatca gttcgaatcg ctaacag        57

<210> SEQ ID NO 6
<211> LENGTH: 13
<212> TYPE: DNA
<213> ORGANISM: Artificial Sequence
<220> FEATURE:
<223> OTHER INFORMATION: U6 gene transcriptional terminator sequence

<400> SEQUENCE: 6 tttttttttct ctt                                                       13

<210> SEQ ID NO 7
<211> LENGTH: 4104
<212> TYPE: DNA
<213> ORGANISM: Artificial Sequence
<220> FEATURE:
<223> OTHER INFORMATION: Filamentous fungal cell codon optimised
      Streptococcus pyogenes Cas9-encoding gene

<400> SEQUENCE: 7
atggacaaga agtacagcat cggcctcgac atcggcacca actcggtggg ctgggccgtc      60
atcacggacg aatataaggt cccgtcgaag aagttcaagg tcctcggcaa tacagaccgc     120
cacagcatca agaaaaactt gatcggcgcc ctcctgttcg atagcggcga gaccgcggag     180
gcgaccaggc tcaagaggac cgccaggaga cggtacacta ggcgcaagaa caggatctgc     240
tacctgcagg agatcttcag caacgagatg gcgaaggtgg acgactcctt cttccaccgc     300
ctggaggaat cattcctggt ggaggaggac aagaagcatg agcggcaccc aatcttcggc     360
aacatcgtcg acgaggtggc ctaccacgag aagtacccga caatctacca cctccggaag     420
aaactggtgg acagcacaga caaggcggac ctccggctca tctaccttgc cctcgcgcat     480
atgatcaagt tccgcggcca cttcctcatc gagggcgacc tgaacccgga caactccgac     540
gtggacaagc tgttcatcca gctcgtgcag acgtacaatc aactgttcga ggagaacccc     600
ataaacgcta cggcgtggga cgccaaggcc atcctctcgg ccaggctctc gaaatcaaga     660
aggctggaga accttatcgc gcagttgcca ggcgaaaaga gaacggcct cttcggcaac     720 cttattgcgc tcagcctcgg cctgacgccg aacttcaaat caaacttcga cctcgcggag     780
gacgccaagc tccagctctc aaaggacacc tacgacgacg acctcgacaa cctcctggcc     840
cagataggag accagtacgc ggacctcttc ctcgccgcca gaacctctc cgacgctatc     900 ctgctcagcg acatccttcg ggtcaacacc gaaattacca aggcaccgct gtccgccagc     960
atgattaaac gctacgacga gcaccatcag gacctcacgc tgctcaaggc actcgtccgc    1020
cagcagctcc ccgagaagta caaggagatc ttcttcgacc aatcaaaaaa cggctacgcg    1080

-continued

```
ggatatatcg acggcggtgc cagccaggaa gagttctaca agttcatcaa accaatcctg    1140
gagaagatgg acggcaccga ggagttgctg gtcaagctca acagggagga cctcctcagg    1200
aagcagagga ccttcgacaa cggctccatc ccgcatcaga tccacctggg cgaactgcat    1260
gccatcctgc ggcgccagga ggacttctac ccgttcctga aggataaccg ggagaagatc    1320
gagaagatct tgacgttccg catcccatac tacgtgggcc cgctggctcg cggcaactcc    1380
cggttcgcct ggatgacccg gaagtcgagc gagaccatca cccctggaa ctttgaggag     1440 gtggtcgata agggcgctag cgctcagagc ttcatcgagc gcatgaccaa cttcgataaa    1500
aacctgccca tgaaaaagt cctccccaag cactcgctgc tctacgagta cttcaccgtg     1560
tacaacgagc tcaccaaggt caaatacgtc accgagggca tgcggaagcc ggcgttcctg    1620
agcggcgagc agaagaaggc gatagtggac ctcctcttca agaccaacag gaaggtgacc    1680
gtgaagcaat aaaagagga ctacttcaag aaaatagagt gcttcgactc cgtggagatc     1740
tcgggcgtgg aggatcggtt caacgcctca ctcggcacgt atcacgacct cctcaagatc    1800
attaaagaca aggacttcct cgacaacgag gagaacgagg acatcctcga ggacatcgtc    1860
ctcaccctga ccctgttcga ggaccgcgaa atgatcgagg agaggctgaa gacctacgcg    1920
cacctgttcg acgacaaggt catgaaacag ctcaagaggc gccgctacac tggttgggga    1980
aggctgtccc gcaagctcat taatggcatc agggacaagc agagcggcaa gaccatcctg    2040
gacttcctca gtccgacgg gttcgccaac cgcaacttca tgcagctcat tcacgacgac    2100
tcgctcacgt tcaaggaaga catccagaag gcacaggtga gcgggcaggg tgactccctc    2160
cacgaacaca tcgccaacct ggccggctcg ccggccatta aaaagggcat cctgcagacg    2220
gtcaaggtcg tcgacgagct cgtgaaggtg atgggccggc acaagcccga aaatatcgtc    2280
atagagatgg ccaggagaa ccagaccacc caaaaagggc agaagaactc gcgcgagcgg    2340
atgaaacgga tcgaggaggg cattaaagag ctcgggtccc agatcctgaa ggagcacccc    2400
gtggaaaata cccagctcca gaatgaaaag ctctacctct actacctgca gaacggccgc    2460
gacatgtacg tggaccagga gctggacatt aatcggctat cggactacga cgtcgaccac    2520
atcgtgccgc agtcgttcct caaggacgat agcatcgaca caaggtgct cacccggtcg     2580 gataaaaatc ggggcaagag cgacaacgtg cccagcgagg aggtcgtgaa gaagatgaaa    2640
aactactggc gccagctcct caacgcgaaa ctgatcaccc agcgcaagtt cgacaacctg    2700
acgaaggcgg aacgcggtgg cttgagcgaa ctcgataagg cgggcttcat aaaaaggcag    2760
ctggtcgaga cgcgccagat cacgaagcat gtcgcccaga tcctggacag ccgcatgaat    2820
actaagtacg atgaaaacga caagctgatc cgggaggtga aggtgatcac gctgaagtcc    2880
aagctcgtgt cggacttccg caaggacttc cagttctaca aggtccgcga gatcaacaac    2940
taccaccacg cccacgacgc ctacctgaat gcggtggtcg ggaccgccct gatcaagaag    3000
tacccgaagc tggagtcgga gttcgtgtac ggcgactaca aggtctacga cgtgcgcaaa    3060
atgatcgcca agtccgagca ggagatcggc aaggccacgg caaaatactt cttctactcg    3120
aacatcatga acttcttcaa gaccgagatc accctcgcga acggcgagat ccgcaagcgc    3180
ccgctcatcg aaaccaacgg cgagacgggc gagatcgtct gggataaggg ccgggatttc    3240
gcgacggtcc gcaaggtgct ctccatgccg caagtcaata tcgtgaaaaa gacggaggtc    3300
cagacgggcg ggttcagcaa ggagtccatc ctcccgaagc gcaactccga caagctcatc    3360
gcgaggaaga aggattggga cccgaaaaaa tatggcggct cgacagcccc gaccgtcgca    3420
tacagcgtcc tcgtcgtggc gaaggtggag aagggcaagt caaagaagct caagtccgtg    3480
```

-continued

```
aaggagctgc tcgggatcac gattatggag cggtcctcct tcgagaagaa cccgatcgac    3540
ttcctagagg ccaagggata taaggaggtc aagaaggacc tgattattaa actgccgaag    3600
tactcgctct tcgagctgga aaacggccgc aagaggatgc tcgcctccgc aggcgagttg    3660
cagaagggca acgagctcgc cctcccgagc aaatacgtca atttcctgta cctcgctagc    3720
cactatgaaa agctcaaggg cagcccggag gacaacgagc agaagcagct cttcgtggag    3780
cagcacaagc attacctgga cgagatcatc gagcagatca gcgagttctc gaagcgggtg    3840
atcctcgccg acgcgaacct ggacaaggtg ctgtcggcat ataacaagca ccgcgacaaa    3900
ccaatacgcg agcaggccga aaatatcatc cacctcttca ccctcaccaa cctcggcgct    3960
ccggcagcct tcaagtactt cgacaccacg attgaccgga agcggtacac gagcacgaag    4020
gaggtgctcg atgcgacgct gatccaccag agcatcacag ggctctatga aacacgcatc    4080
gacctgagcc agctgggcgg agac                                            4104
```

<210> SEQ ID NO 8
<211> LENGTH: 1368
<212> TYPE: PRT
<213> ORGANISM: Artificial Sequence
<220> FEATURE:
<223> OTHER INFORMATION: Streptococcus pyogenes Cas9 Codon optimized
      sequence

<400> SEQUENCE: 8

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240
```

```
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
```

-continued

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

-continued

Thr Gly Glu Ile Val Trp Asp Lys Gly Arg Asp Phe Ala Thr Val
1070              1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
    1355                1360                1365

<210> SEQ ID NO 9
<211> LENGTH: 7
<212> TYPE: PRT
<213> ORGANISM: Artificial Sequence
<220> FEATURE:
<223> OTHER INFORMATION: SV40 NLS

<400> SEQUENCE: 9

Pro Lys Lys Lys Arg Lys Val
1               5

<210> SEQ ID NO 10
<211> LENGTH: 7
<212> TYPE: PRT
<213> ORGANISM: Artificial Sequence

```
<220> FEATURE:
<223> OTHER INFORMATION: Trichoderma reesei blr2 gene NLS

<400> SEQUENCE: 10

Lys Lys Lys Lys Leu Lys Leu
1               5

<210> SEQ ID NO 11
<211> LENGTH: 1388
<212> TYPE: PRT
<213> ORGANISM: Artificial Sequence
<220> FEATURE:
<223> OTHER INFORMATION: Streptococcus thermophilus LMD-9 Cas9

<400> SEQUENCE: 11

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320
```

```
Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
            405                 410                 415

Gln Glu Met Arg Ala Ile Leu Asp Lys Gln Ala Lys Phe Tyr Pro Phe
        420                 425                 430

Leu Ala Lys Asn Lys Glu Arg Ile Glu Lys Ile Leu Thr Phe Arg Ile
    435                 440                 445

Pro Tyr Tyr Val Gly Pro Leu Ala Arg Gly Asn Ser Asp Phe Ala Trp
450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
            485                 490                 495

Ser Phe Asp Leu Tyr Leu Pro Glu Glu Lys Val Leu Pro Lys His Ser
        500                 505                 510

Leu Leu Tyr Glu Thr Phe Asn Val Tyr Asn Glu Leu Thr Lys Val Arg
    515                 520                 525

Phe Ile Ala Glu Ser Met Arg Asp Tyr Gln Phe Leu Asp Ser Lys Gln
530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
            565                 570                 575

Ile Glu Leu Lys Gly Ile Glu Lys Gln Phe Asn Ser Ser Leu Ser Thr
        580                 585                 590

Tyr His Asp Leu Leu Asn Ile Ile Asn Asp Lys Glu Phe Leu Asp Asp
    595                 600                 605

Ser Ser Asn Glu Ala Ile Ile Glu Glu Ile Ile His Thr Leu Thr Ile
610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
            645                 650                 655

Gly Trp Gly Lys Leu Ser Ala Lys Leu Ile Asn Gly Ile Arg Asp Glu
        660                 665                 670

Lys Ser Gly Asn Thr Ile Leu Asp Tyr Leu Ile Asp Asp Gly Ile Ser
    675                 680                 685

Asn Arg Asn Phe Met Gln Leu Ile His Asp Asp Ala Leu Ser Phe Lys
690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
            725                 730                 735
```

Gly Ile Leu Gln Ser Ile Lys Ile Val Asp Glu Leu Val Lys Val Met
            740                 745                 750

Gly Gly Arg Lys Pro Glu Ser Ile Val Val Glu Met Ala Arg Glu Asn
            755                 760                 765

Gln Tyr Thr Asn Gln Gly Lys Ser Asn Ser Gln Gln Arg Leu Lys Arg
            770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
                805                 810                 815

Arg Leu Tyr Leu Tyr Leu Gln Asn Gly Lys Asp Met Tyr Thr Gly
            820                 825                 830

Asp Asp Leu Asp Ile Asp Arg Leu Ser Asn Tyr Asp Ile Asp His Ile
            835                 840                 845

Ile Pro Gln Ala Phe Leu Lys Asp Asn Ser Ile Asp Asn Lys Val Leu
            850                 855                 860

Val Ser Ser Ala Ser Asn Arg Gly Lys Ser Asp Asp Val Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
            900                 905                 910

Gly Gly Leu Ser Pro Glu Asp Lys Ala Gly Phe Ile Gln Arg Gln Leu
            915                 920                 925

Val Glu Thr Arg Gln Ile Thr Lys His Val Ala Arg Leu Leu Asp Glu
            930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
            965                 970                 975

Phe Glu Leu Tyr Lys Val Arg Glu Ile Asn Asp Phe His His Ala His
            980                 985                 990

Asp Ala Tyr Leu Asn Ala Val Val Ala Ser Ala Leu Leu Lys Lys Tyr
            995                 1000                1005

Pro Lys Leu Glu Pro Glu Phe Val Tyr Gly Asp Tyr Pro Lys Tyr
            1010                1015                1020

Asn Ser Phe Arg Glu Arg Lys Ser Ala Thr Glu Lys Val Tyr Phe
            1025                1030                1035

Tyr Ser Asn Ile Met Asn Ile Phe Lys Lys Ser Ile Ser Leu Ala
            1040                1045                1050

Asp Gly Arg Val Ile Glu Arg Pro Leu Ile Glu Val Asn Glu Glu
            1055                1060                1065

Thr Gly Glu Ser Val Trp Asn Lys Glu Ser Asp Leu Ala Thr Val
            1070                1075                1080

Arg Arg Val Leu Ser Tyr Pro Gln Val Asn Val Val Lys Lys Val
            1085                1090                1095

Glu Glu Gln Asn His Gly Leu Asp Arg Gly Lys Pro Lys Gly Leu
            1100                1105                1110

Phe Asn Ala Asn Leu Ser Ser Lys Pro Lys Pro Asn Ser Asn Glu
            1115                1120                1125

Asn Leu Val Gly Ala Lys Glu Tyr Leu Asp Pro Lys Lys Tyr Gly
            1130                1135                1140

Gly Tyr Ala Gly Ile Ser Asn Ser Phe Thr Val Leu Val Lys Gly
    1145                1150                1155

Thr Ile Glu Lys Gly Ala Lys Lys Lys Ile Thr Asn Val Leu Glu
    1160                1165                1170

Phe Gln Gly Ile Ser Ile Leu Asp Arg Ile Asn Tyr Arg Lys Asp
    1175                1180                1185

Lys Leu Asn Phe Leu Leu Glu Lys Gly Tyr Lys Asp Ile Glu Leu
    1190                1195                1200

Ile Ile Glu Leu Pro Lys Tyr Ser Leu Phe Glu Leu Ser Asp Gly
    1205                1210                1215

Ser Arg Arg Met Leu Ala Ser Ile Leu Ser Thr Asn Asn Lys Arg
    1220                1225                1230

Gly Glu Ile His Lys Gly Asn Gln Ile Phe Leu Ser Gln Lys Phe
    1235                1240                1245

Val Lys Leu Leu Tyr His Ala Lys Arg Ile Ser Asn Thr Ile Asn
    1250                1255                1260

Glu Asn His Arg Lys Tyr Val Glu Asn His Lys Lys Glu Phe Glu
    1265                1270                1275

Glu Leu Phe Tyr Tyr Ile Leu Glu Phe Asn Glu Asn Tyr Val Gly
    1280                1285                1290

Ala Lys Lys Asn Gly Lys Leu Leu Asn Ser Ala Phe Gln Ser Trp
    1295                1300                1305

Gln Asn His Ser Ile Asp Glu Leu Cys Ser Ser Phe Ile Gly Pro
    1310                1315                1320

Thr Gly Ser Glu Arg Lys Gly Leu Phe Glu Leu Thr Ser Arg Gly
    1325                1330                1335

Ser Ala Ala Asp Phe Glu Phe Leu Gly Val Lys Ile Pro Arg Tyr
    1340                1345                1350

Arg Asp Tyr Thr Pro Ser Ser Leu Leu Lys Asp Ala Thr Leu Ile
    1355                1360                1365

His Gln Ser Val Thr Gly Leu Tyr Glu Thr Arg Ile Asp Leu Ala
    1370                1375                1380

Lys Leu Gly Glu Gly
    1385

<210> SEQ ID NO 12
<211> LENGTH: 1345
<212> TYPE: PRT
<213> ORGANISM: Artificial Sequence
<220> FEATURE:
<223> OTHER INFORMATION: Streptococcus mutans UA159 CAS9

<400> SEQUENCE: 12

Met Lys Lys Pro Tyr Ser Ile Gly Leu Asp Ile Gly Thr Asn Ser Val
1               5                   10                  15

Gly Trp Ala Val Val Thr Asp Asp Tyr Lys Val Pro Ala Lys Lys Met
            20                  25                  30

Lys Val Leu Gly Asn Thr Asp Lys Ser His Ile Glu Lys Asn Leu Leu
        35                  40                  45

Gly Ala Leu Leu Phe Asp Ser Gly Asn Thr Ala Glu Asp Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Glu Glu Met Gly Lys Val Asp Asp Ser
                85                  90                  95

```
Phe Phe His Arg Leu Glu Asp Ser Phe Leu Val Thr Glu Asp Lys Arg
            100                 105                 110

Gly Glu Arg His Pro Ile Phe Gly Asn Leu Glu Glu Val Lys Tyr
115                 120                 125

His Glu Asn Phe Pro Thr Ile Tyr His Leu Arg Gln Tyr Leu Ala Asp
            130                 135                 140

Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
            195                 200                 205

Glu Glu Ile Leu Thr Asp Lys Ile Ser Lys Ser Ala Lys Lys Asp Arg
210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255

Glu Leu Glu Glu Lys Ala Pro Leu Gln Phe Ser Lys Asp Thr Tyr Glu
            260                 265                 270

Glu Glu Leu Glu Val Leu Leu Ala Gln Ile Gly Asp Asn Tyr Ala Glu
            275                 280                 285

Leu Phe Leu Ser Ala Lys Lys Leu Tyr Asp Ser Ile Leu Leu Ser Gly
            290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
                325                 330                 335

Gln Phe Ile Arg Gln Lys Leu Ser Asp Lys Tyr Asn Glu Val Phe Ser
            340                 345                 350

Asp Val Ser Lys Asp Gly Tyr Ala Gly Tyr Ile Asp Gly Lys Thr Asn
            355                 360                 365

Gln Glu Ala Phe Tyr Lys Tyr Leu Lys Gly Leu Leu Asn Lys Ile Glu
370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
                405                 410                 415

Gln Glu Met Arg Ala Ile Ile Arg Arg Gln Ala Glu Phe Tyr Pro Phe
            420                 425                 430

Leu Ala Asp Asn Gln Asp Arg Ile Glu Lys Leu Leu Thr Phe Arg Ile
            435                 440                 445

Pro Tyr Tyr Val Gly Pro Leu Ala Arg Gly Lys Ser Asp Phe Ala Trp
450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
                485                 490                 495

Asn Tyr Asp Leu Tyr Leu Pro Asn Gln Lys Val Leu Pro Lys His Ser
            500                 505                 510
```

-continued

Leu Leu Tyr Glu Lys Phe Thr Val Tyr Asn Glu Leu Thr Lys Val Lys
         515                 520                 525

Tyr Lys Thr Glu Gln Gly Lys Thr Ala Phe Phe Asp Ala Asn Met Lys
         530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
                 565                 570                 575

Val Asp Leu Thr Gly Leu Asp Lys Glu Asn Lys Val Phe Asn Ala Ser
             580                 585                 590

Tyr Gly Thr Tyr His Asp Leu Cys Lys Ile Leu Asp Lys Asp Phe Leu
         595                 600                 605

Asp Asn Ser Lys Asn Glu Lys Ile Leu Glu Asp Ile Val Leu Thr Leu
         610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
                 645                 650                 655

Tyr Thr Gly Trp Gly Arg Leu Ser Ala Glu Leu Ile His Gly Ile Arg
             660                 665                 670

Asn Lys Glu Ser Arg Lys Thr Ile Leu Asp Tyr Leu Ile Asp Asp Gly
         675                 680                 685

Asn Ser Asn Arg Asn Phe Met Gln Leu Ile Asn Asp Asp Ala Leu Ser
         690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
                 725                 730                 735

Gly Ile Leu Gln Ser Leu Lys Ile Val Asp Glu Leu Val Lys Ile Met
             740                 745                 750

Gly His Gln Pro Glu Asn Ile Val Val Glu Met Ala Arg Glu Asn Gln
         755                 760                 765

Phe Thr Asn Gln Gly Arg Arg Asn Ser Gln Gln Arg Leu Lys Gly Leu
         770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
                 805                 810                 815

Gln Asn Gly Arg Asp Met Tyr Thr Gly Glu Glu Leu Asp Ile Asp Tyr
             820                 825                 830

Leu Ser Gln Tyr Asp Ile Asp His Ile Ile Pro Gln Ala Phe Ile Lys
         835                 840                 845

Asp Asn Ser Ile Asp Asn Arg Val Leu Thr Ser Ser Lys Glu Asn Arg
         850                 855                 860

Gly Lys Ser Asp Asp Val Pro Ser Lys Asp Val Val Arg Lys Met Lys
865                 870                 875                 880

Ser Tyr Trp Ser Lys Leu Leu Ser Ala Lys Leu Ile Thr Gln Arg Lys
                 885                 890                 895

Phe Asp Asn Leu Thr Lys Ala Glu Arg Gly Gly Leu Thr Asp Asp Asp
             900                 905                 910

Lys Ala Gly Phe Ile Lys Arg Gln Leu Val Glu Thr Arg Gln Ile Thr
         915                 920                 925

-continued

```
Lys His Val Ala Arg Ile Leu Asp Glu Arg Phe Asn Thr Glu Thr Asp
    930                 935                 940
Glu Asn Asn Lys Lys Ile Arg Gln Val Lys Ile Val Thr Leu Lys Ser
945                 950                 955                 960
Asn Leu Val Ser Asn Phe Arg Lys Glu Phe Glu Leu Tyr Lys Val Arg
                965                 970                 975
Glu Ile Asn Asp Tyr His His Ala His Asp Ala Tyr Leu Asn Ala Val
                980                 985                 990
Ile Gly Lys Ala Leu Leu Gly Val Tyr Pro Gln Leu Glu Pro Glu Phe
        995                 1000                1005
Val Tyr Gly Asp Tyr Pro His Phe His Gly His Lys Glu Asn Lys
    1010                1015                1020
Ala Thr Ala Lys Lys Phe Phe Tyr Ser Asn Ile Met Asn Phe Phe
    1025                1030                1035
Lys Lys Asp Asp Val Arg Thr Asp Lys Asn Gly Glu Ile Ile Trp
    1040                1045                1050
Lys Lys Asp Glu His Ile Ser Asn Ile Lys Lys Val Leu Ser Tyr
    1055                1060                1065
Pro Gln Val Asn Ile Val Lys Lys Val Glu Glu Gln Thr Gly Gly
    1070                1075                1080
Phe Ser Lys Glu Ser Ile Leu Pro Lys Gly Asn Ser Asp Lys Leu
    1085                1090                1095
Ile Pro Arg Lys Thr Lys Lys Phe Tyr Trp Asp Thr Lys Lys Tyr
    1100                1105                1110
Gly Gly Phe Asp Ser Pro Ile Val Ala Tyr Ser Ile Leu Val Ile
    1115                1120                1125
Ala Asp Ile Glu Lys Gly Lys Ser Lys Lys Leu Lys Thr Val Lys
    1130                1135                1140
Ala Leu Val Gly Val Thr Ile Met Glu Lys Met Thr Phe Glu Arg
    1145                1150                1155
Asp Pro Val Ala Phe Leu Glu Arg Lys Gly Tyr Arg Asn Val Gln
    1160                1165                1170
Glu Glu Asn Ile Ile Lys Leu Pro Lys Tyr Ser Leu Phe Lys Leu
    1175                1180                1185
Glu Asn Gly Arg Lys Arg Leu Leu Ala Ser Ala Arg Glu Leu Gln
    1190                1195                1200
Lys Gly Asn Glu Ile Val Leu Pro Asn His Leu Gly Thr Leu Leu
    1205                1210                1215
Tyr His Ala Lys Asn Ile His Lys Val Asp Glu Pro Lys His Leu
    1220                1225                1230
Asp Tyr Val Asp Lys His Lys Asp Glu Phe Lys Glu Leu Leu Asp
    1235                1240                1245
Val Val Ser Asn Phe Ser Lys Lys Tyr Thr Leu Ala Glu Gly Asn
    1250                1255                1260
Leu Glu Lys Ile Lys Glu Leu Tyr Ala Gln Asn Asn Gly Glu Asp
    1265                1270                1275
Leu Lys Glu Leu Ala Ser Ser Phe Ile Asn Leu Leu Thr Phe Thr
    1280                1285                1290
Ala Ile Gly Ala Pro Ala Thr Phe Lys Phe Phe Asp Lys Asn Ile
    1295                1300                1305
Asp Arg Lys Arg Tyr Thr Ser Thr Thr Glu Ile Leu Asn Ala Thr
    1310                1315                1320
```

-continued

Leu Ile His Gln Ser Ile Thr Gly Leu Tyr Glu Thr Arg Ile Asp
1325                1330                1335

Leu Asn Lys Leu Gly Gly Asp
1340                1345

<210> SEQ ID NO 13
<211> LENGTH: 984
<212> TYPE: PRT
<213> ORGANISM: Artificial Sequence
<220> FEATURE:
<223> OTHER INFORMATION: Campylobacter jejuni Cas9

<400> SEQUENCE: 13

Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
        35                  40                  45

Arg Leu Ala Arg Ser Ala Arg Lys Arg Leu Ala Arg Arg Lys Ala Arg
    50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
    130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
    210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
    290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

-continued

Glu Phe Ile Lys Ala Leu Gly Glu His Asn Leu Ser Gln Asp Asp Leu
                340                 345                 350

Asn Glu Ile Ala Lys Asp Ile Thr Leu Ile Lys Asp Glu Ile Lys Leu
                355                 360                 365

Lys Lys Ala Leu Ala Lys Tyr Asp Leu Asn Gln Asn Gln Ile Asp Ser
            370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
            435                 440                 445

Asn Pro Val Val Leu Arg Ala Ile Lys Glu Tyr Arg Lys Val Leu Asn
        450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
            515                 520                 525

Leu Phe Lys Glu Gln Lys Glu Phe Cys Ala Tyr Ser Gly Glu Lys Ile
        530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
            595                 600                 605

Lys Asn Leu Pro Thr Lys Lys Gln Lys Arg Ile Leu Asp Lys Asn Tyr
        610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
            675                 680                 685

Ala Leu Arg His Thr Trp Gly Phe Ser Ala Lys Asp Arg Asn Asn His
        690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
            755                 760                 765

Lys Ile Asp Glu Ile Phe Val Ser Lys Pro Arg Lys Lys Pro Ser
770                 775                 780

Gly Ala Leu His Glu Glu Thr Phe Arg Lys Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
            835                 840                 845

Ile Tyr Thr Met Asp Phe Ala Leu Lys Val Leu Pro Asn Lys Ala Val
            850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
            915                 920                 925

Glu Thr Leu Ser Lys Asn Gln Lys Ile Leu Phe Lys Asn Ala Asn Glu
            930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
            980

<210> SEQ ID NO 14
<211> LENGTH: 1082
<212> TYPE: PRT
<213> ORGANISM: Artificial Sequence
<220> FEATURE:
<223> OTHER INFORMATION: Neisseria meningitidis Cas9

<400> SEQUENCE: 14

Met Ala Ala Phe Lys Pro Asn Ser Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

Glu Asn Pro Ile Arg Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Thr Arg Arg Leu Leu Lys Arg Glu Gly Val Leu Gln Ala Ala Asn
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

```
Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Gly Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
                180                 185                 190

Arg Asn Gln Arg Ser Asp Tyr Ser His Thr Phe Ser Arg Lys Asp Leu
                195                 200                 205

Gln Ala Glu Leu Ile Leu Leu Phe Glu Lys Gln Lys Glu Phe Gly Asn
210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
                260                 265                 270

Thr Ala Glu Arg Phe Ile Trp Leu Thr Lys Leu Asn Asn Leu Arg Ile
                275                 280                 285

Leu Glu Gln Gly Ser Glu Arg Pro Leu Thr Asp Thr Glu Arg Ala Thr
290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
                340                 345                 350

Tyr His Ala Ile Ser Arg Ala Leu Glu Lys Glu Gly Leu Lys Asp Lys
                355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
                420                 425                 430

Pro Leu Met Glu Gln Gly Lys Arg Tyr Asp Glu Ala Cys Ala Glu Ile
                435                 440                 445

Tyr Gly Asp His Tyr Gly Lys Lys Asn Thr Glu Glu Lys Ile Tyr Leu
                450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
                500                 505                 510

Phe Lys Asp Arg Lys Glu Ile Glu Lys Arg Gln Glu Glu Asn Arg Lys
                515                 520                 525

Asp Arg Glu Lys Ala Ala Ala Lys Phe Arg Glu Tyr Phe Pro Asn Phe
530                 535                 540
```

```
Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
                580                 585                 590

Ser Arg Thr Trp Asp Asp Ser Phe Asn Asn Lys Val Leu Val Leu Gly
        595                 600                 605

Ser Glu Asn Gln Asn Lys Gly Asn Gln Thr Pro Tyr Glu Tyr Phe Asn
        610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
                660                 665                 670

Val Asn Arg Phe Leu Cys Gln Phe Val Ala Asp Arg Met Arg Leu Thr
                675                 680                 685

Gly Lys Gly Lys Lys Arg Val Phe Ala Ser Asn Gly Gln Ile Thr Asn
690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Val Ala
                725                 730                 735

Met Gln Gln Lys Ile Thr Arg Phe Val Arg Tyr Lys Glu Met Asn Ala
                740                 745                 750

Phe Asp Gly Lys Thr Ile Asp Lys Glu Thr Gly Glu Val Leu His Gln
                755                 760                 765

Lys Thr His Phe Pro Gln Pro Trp Glu Phe Phe Ala Gln Glu Val Met
770                 775                 780

Ile Arg Val Phe Gly Lys Pro Asp Gly Lys Pro Glu Phe Glu Glu Ala
785                 790                 795                 800

Asp Thr Leu Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
                820                 825                 830

Ala Pro Asn Arg Lys Met Ser Gly Gln Gly His Met Glu Thr Val Lys
                835                 840                 845

Ser Ala Lys Arg Leu Asp Glu Gly Val Ser Val Leu Arg Val Pro Leu
850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
                900                 905                 910

Ala Gly Asn Arg Thr Gln Gln Val Lys Ala Val Arg Val Glu Gln Val
                915                 920                 925

Gln Lys Thr Gly Val Trp Val Arg Asn His Asn Gly Ile Ala Asp Asn
930                 935                 940

Ala Thr Met Val Arg Val Asp Val Phe Glu Lys Gly Asp Lys Tyr Tyr
945                 950                 955                 960
```

```
Leu Val Pro Ile Tyr Ser Trp Gln Val Ala Lys Gly Ile Leu Pro Asp
                965                 970                 975
Arg Ala Val Val Gln Gly Lys Asp Glu Glu Asp Trp Gln Leu Ile Asp
            980                 985                 990
Asp Ser Phe Asn Phe Lys Phe Ser Leu His Pro Asn Asp Leu Val Glu
        995                1000                1005
Val Ile Thr Lys Lys Ala Arg Met Phe Gly Tyr Phe Ala Ser Cys
    1010                1015                1020
His Arg Gly Thr Gly Asn Ile Asn Ile Arg Ile His Asp Leu Asp
    1025                1030                1035
His Lys Ile Gly Lys Asn Gly Ile Leu Glu Gly Ile Gly Val Lys
    1040                1045                1050
Thr Ala Leu Ser Phe Gln Lys Tyr Gln Ile Asp Glu Leu Gly Lys
    1055                1060                1065
Glu Ile Arg Pro Cys Arg Leu Lys Lys Arg Pro Pro Val Arg
    1070                1075                1080

<210> SEQ ID NO 15
<211> LENGTH: 1629
<212> TYPE: PRT
<213> ORGANISM: Artificial Sequence
<220> FEATURE:
<223> OTHER INFORMATION: Francisella tularensis subsp. novicida Cas9

<400> SEQUENCE: 15

Met Asn Phe Lys Ile Leu Pro Ile Ala Ile Asp Leu Gly Val Lys Asn
1               5                   10                  15
Thr Gly Val Phe Ser Ala Phe Tyr Gln Lys Gly Thr Ser Leu Glu Arg
            20                  25                  30
Leu Asp Asn Lys Asn Gly Lys Val Tyr Glu Leu Ser Lys Asp Ser Tyr
        35                  40                  45
Thr Leu Leu Met Asn Asn Arg Thr Ala Arg Arg His Gln Arg Arg Gly
    50                  55                  60
Ile Asp Arg Lys Gln Leu Val Lys Arg Leu Phe Lys Leu Ile Trp Thr
65                  70                  75                  80
Glu Gln Leu Asn Leu Glu Trp Asp Lys Asp Thr Gln Gln Ala Ile Ser
                85                  90                  95
Phe Leu Phe Asn Arg Arg Gly Phe Ser Phe Ile Thr Asp Gly Tyr Ser
            100                 105                 110
Pro Glu Tyr Leu Asn Ile Val Pro Glu Gln Val Lys Ala Ile Leu Met
        115                 120                 125
Asp Ile Phe Asp Asp Tyr Asn Gly Glu Asp Asp Leu Asp Ser Tyr Leu
    130                 135                 140
Lys Leu Ala Thr Glu Gln Glu Ser Lys Ile Ser Glu Ile Tyr Asn Lys
145                 150                 155                 160
Leu Met Gln Lys Ile Leu Glu Phe Lys Leu Met Lys Leu Cys Thr Asp
                165                 170                 175
Ile Lys Asp Asp Lys Val Ser Thr Lys Thr Leu Lys Glu Ile Thr Ser
            180                 185                 190
Tyr Glu Phe Glu Leu Leu Ala Asp Tyr Leu Ala Asn Tyr Ser Glu Ser
        195                 200                 205
Leu Lys Thr Gln Lys Phe Ser Tyr Thr Asp Lys Gln Gly Asn Leu Lys
    210                 215                 220
Glu Leu Ser Tyr Tyr His His Asp Lys Tyr Asn Ile Gln Glu Phe Leu
225                 230                 235                 240
```

```
Lys Arg His Ala Thr Ile Asn Asp Arg Ile Leu Asp Thr Leu Leu Thr
                245                 250                 255

Asp Asp Leu Asp Ile Trp Asn Phe Asn Phe Glu Lys Phe Asp Phe Asp
            260                 265                 270

Lys Asn Glu Glu Lys Leu Gln Asn Gln Glu Asp Lys Asp His Ile Gln
        275                 280                 285

Ala His Leu His His Phe Val Phe Ala Val Asn Lys Ile Lys Ser Glu
    290                 295                 300

Met Ala Ser Gly Gly Arg His Arg Ser Gln Tyr Phe Gln Glu Ile Thr
305                 310                 315                 320

Asn Val Leu Asp Glu Asn Asn His Gln Glu Gly Tyr Leu Lys Asn Phe
                325                 330                 335

Cys Glu Asn Leu His Asn Lys Lys Tyr Ser Asn Leu Ser Val Lys Asn
            340                 345                 350

Leu Val Asn Leu Ile Gly Asn Leu Ser Asn Leu Glu Leu Lys Pro Leu
        355                 360                 365

Arg Lys Tyr Phe Asn Asp Lys Ile His Ala Lys Ala Asp His Trp Asp
    370                 375                 380

Glu Gln Lys Phe Thr Glu Thr Tyr Cys His Trp Ile Leu Gly Glu Trp
385                 390                 395                 400

Arg Val Gly Val Lys Asp Gln Asp Lys Lys Asp Gly Ala Lys Tyr Ser
                405                 410                 415

Tyr Lys Asp Leu Cys Asn Glu Leu Lys Gln Lys Val Thr Lys Ala Gly
            420                 425                 430

Leu Val Asp Phe Leu Leu Glu Leu Asp Pro Cys Arg Thr Ile Pro Pro
        435                 440                 445

Tyr Leu Asp Asn Asn Asn Arg Lys Pro Pro Lys Cys Gln Ser Leu Ile
    450                 455                 460

Leu Asn Pro Lys Phe Leu Asp Asn Gln Tyr Pro Asn Trp Gln Gln Tyr
465                 470                 475                 480

Leu Gln Glu Leu Lys Lys Leu Gln Ser Ile Gln Asn Tyr Leu Asp Ser
                485                 490                 495

Phe Glu Thr Asp Leu Lys Val Leu Lys Ser Ser Lys Asp Gln Pro Tyr
            500                 505                 510

Phe Val Glu Tyr Lys Ser Ser Asn Gln Gln Ile Ala Ser Gly Gln Arg
        515                 520                 525

Asp Tyr Lys Asp Leu Asp Ala Arg Ile Leu Gln Phe Ile Phe Asp Arg
    530                 535                 540

Val Lys Ala Ser Asp Glu Leu Leu Leu Asn Glu Ile Tyr Phe Gln Ala
545                 550                 555                 560

Lys Lys Leu Lys Gln Lys Ala Ser Ser Glu Leu Lys Leu Glu Ser
                565                 570                 575

Ser Lys Lys Leu Asp Glu Val Ile Ala Asn Ser Gln Leu Ser Gln Ile
            580                 585                 590

Leu Lys Ser Gln His Thr Asn Gly Ile Phe Glu Gln Gly Thr Phe Leu
        595                 600                 605

His Leu Val Cys Lys Tyr Tyr Lys Gln Arg Gln Arg Ala Arg Asp Ser
    610                 615                 620

Arg Leu Tyr Ile Met Pro Glu Tyr Arg Tyr Asp Lys Lys Leu His Lys
625                 630                 635                 640

Tyr Asn Asn Thr Gly Arg Phe Asp Asp Asp Asn Gln Leu Leu Thr Tyr
                645                 650                 655
```

-continued

Cys Asn His Lys Pro Arg Gln Lys Arg Tyr Gln Leu Leu Asn Asp Leu
              660                 665                 670

Ala Gly Val Leu Gln Val Ser Pro Asn Phe Leu Lys Asp Lys Ile Gly
          675                 680                 685

Ser Asp Asp Asp Leu Phe Ile Ser Lys Trp Leu Val Glu His Ile Arg
690                 695                 700

Gly Phe Lys Lys Ala Cys Glu Asp Ser Leu Lys Ile Gln Lys Asp Asn
705                 710                 715                 720

Arg Gly Leu Leu Asn His Lys Ile Asn Ile Ala Arg Asn Thr Lys Gly
              725                 730                 735

Lys Cys Glu Lys Glu Ile Phe Asn Leu Ile Cys Lys Ile Glu Gly Ser
          740                 745                 750

Glu Asp Lys Lys Gly Asn Tyr Lys His Gly Leu Ala Tyr Glu Leu Gly
              755                 760                 765

Val Leu Leu Phe Gly Glu Pro Asn Glu Ala Ser Lys Pro Glu Phe Asp
          770                 775                 780

Arg Lys Ile Lys Lys Phe Asn Ser Ile Tyr Ser Phe Ala Gln Ile Gln
785                 790                 795                 800

Gln Ile Ala Phe Ala Glu Arg Lys Gly Asn Ala Asn Thr Cys Ala Val
              805                 810                 815

Cys Ser Ala Asp Asn Ala His Arg Met Gln Gln Ile Lys Ile Thr Glu
          820                 825                 830

Pro Val Glu Asp Asn Lys Asp Lys Ile Ile Leu Ser Ala Lys Ala Gln
          835                 840                 845

Arg Leu Pro Ala Ile Pro Thr Arg Ile Val Asp Gly Ala Val Lys Lys
850                 855                 860

Met Ala Thr Ile Leu Ala Lys Asn Ile Val Asp Asp Asn Trp Gln Asn
865                 870                 875                 880

Ile Lys Gln Val Leu Ser Ala Lys His Gln Leu His Ile Pro Ile Ile
              885                 890                 895

Thr Glu Ser Asn Ala Phe Glu Phe Glu Pro Ala Leu Ala Asp Val Lys
          900                 905                 910

Gly Lys Ser Leu Lys Asp Arg Arg Lys Lys Ala Leu Glu Arg Ile Ser
          915                 920                 925

Pro Glu Asn Ile Phe Lys Asp Lys Asn Asn Arg Ile Lys Glu Phe Ala
930                 935                 940

Lys Gly Ile Ser Ala Tyr Ser Gly Ala Asn Leu Thr Asp Gly Asp Phe
945                 950                 955                 960

Asp Gly Ala Lys Glu Glu Leu Asp His Ile Ile Pro Arg Ser His Lys
              965                 970                 975

Lys Tyr Gly Thr Leu Asn Asp Glu Ala Asn Leu Ile Cys Val Thr Arg
          980                 985                 990

Gly Asp Asn Lys Asn Lys Gly Asn Arg Ile Phe Cys Leu Arg Asp Leu
          995                 1000                1005

Ala Asp Asn Tyr Lys Leu Lys Gln Phe Glu Thr Thr Asp Asp Leu
      1010                1015                1020

Glu Ile Glu Lys Lys Ile Ala Asp Thr Ile Trp Asp Ala Asn Lys
      1025                1030                1035

Lys Asp Phe Lys Phe Gly Asn Tyr Arg Ser Phe Ile Asn Leu Thr
      1040                1045                1050

Pro Gln Glu Gln Lys Ala Phe Arg His Ala Leu Phe Leu Ala Asp
      1055                1060                1065

```
Glu Asn Pro Ile Lys Gln Ala Val Ile Arg Ala Ile Asn Asn Arg
    1070            1075            1080

Asn Arg Thr Phe Val Asn Gly Thr Gln Arg Tyr Phe Ala Glu Val
    1085            1090            1095

Leu Ala Asn Asn Ile Tyr Leu Arg Ala Lys Lys Glu Asn Leu Asn
    1100            1105            1110

Thr Asp Lys Ile Ser Phe Asp Tyr Phe Gly Ile Pro Thr Ile Gly
    1115            1120            1125

Asn Gly Arg Gly Ile Ala Glu Ile Arg Gln Leu Tyr Glu Lys Val
    1130            1135            1140

Asp Ser Asp Ile Gln Ala Tyr Ala Lys Gly Asp Lys Pro Gln Ala
    1145            1150            1155

Ser Tyr Ser His Leu Ile Asp Ala Met Leu Ala Phe Cys Ile Ala
    1160            1165            1170

Ala Asp Glu His Arg Asn Asp Gly Ser Ile Gly Leu Glu Ile Asp
    1175            1180            1185

Lys Asn Tyr Ser Leu Tyr Pro Leu Asp Lys Asn Thr Gly Glu Val
    1190            1195            1200

Phe Thr Lys Asp Ile Phe Ser Gln Ile Lys Ile Thr Asp Asn Glu
    1205            1210            1215

Phe Ser Asp Lys Lys Leu Val Arg Lys Lys Ala Ile Glu Gly Phe
    1220            1225            1230

Asn Thr His Arg Gln Met Thr Arg Asp Gly Ile Tyr Ala Glu Asn
    1235            1240            1245

Tyr Leu Pro Ile Leu Ile His Lys Glu Leu Asn Glu Val Arg Lys
    1250            1255            1260

Gly Tyr Thr Trp Lys Asn Ser Glu Glu Ile Lys Ile Phe Lys Gly
    1265            1270            1275

Lys Lys Tyr Asp Ile Gln Gln Leu Asn Asn Leu Val Tyr Cys Leu
    1280            1285            1290

Lys Phe Val Asp Lys Pro Ile Ser Ile Asp Ile Gln Ile Ser Thr
    1295            1300            1305

Leu Glu Glu Leu Arg Asn Ile Leu Thr Thr Asn Asn Ile Ala Ala
    1310            1315            1320

Thr Ala Glu Tyr Tyr Tyr Ile Asn Leu Lys Thr Gln Lys Leu His
    1325            1330            1335

Glu Tyr Tyr Ile Glu Asn Tyr Asn Thr Ala Leu Gly Tyr Lys Lys
    1340            1345            1350

Tyr Ser Lys Glu Met Glu Phe Leu Arg Ser Leu Ala Tyr Arg Ser
    1355            1360            1365

Glu Arg Val Lys Ile Lys Ser Ile Asp Asp Val Lys Gln Val Leu
    1370            1375            1380

Asp Lys Asp Ser Asn Phe Ile Ile Gly Lys Ile Thr Leu Pro Phe
    1385            1390            1395

Lys Lys Glu Trp Gln Arg Leu Tyr Arg Glu Trp Gln Asn Thr Thr
    1400            1405            1410

Ile Lys Asp Asp Tyr Glu Phe Leu Lys Ser Phe Phe Asn Val Lys
    1415            1420            1425

Ser Ile Thr Lys Leu His Lys Lys Val Arg Lys Asp Phe Ser Leu
    1430            1435            1440

Pro Ile Ser Thr Asn Glu Gly Lys Phe Leu Val Lys Arg Lys Thr
    1445            1450            1455
```

-continued

```
Trp Asp Asn Asn Phe Ile Tyr Gln Ile Leu Asn Asp Ser Asp Ser
    1460                1465                1470

Arg Ala Asp Gly Thr Lys Pro Phe Ile Pro Ala Phe Asp Ile Ser
1475                1480                1485

Lys Asn Glu Ile Val Glu Ala Ile Ile Asp Ser Phe Thr Ser Lys
    1490                1495                1500

Asn Ile Phe Trp Leu Pro Lys Asn Ile Glu Leu Gln Lys Val Asp
    1505                1510                1515

Asn Lys Asn Ile Phe Ala Ile Asp Thr Ser Lys Trp Phe Glu Val
    1520                1525                1530

Glu Thr Pro Ser Asp Leu Arg Asp Ile Gly Ile Ala Thr Ile Gln
    1535                1540                1545

Tyr Lys Ile Asp Asn Asn Ser Arg Pro Lys Val Arg Val Lys Leu
    1550                1555                1560

Asp Tyr Val Ile Asp Asp Ser Lys Ile Asn Tyr Phe Met Asn
    1565                1570                1575

His Ser Leu Leu Lys Ser Arg Tyr Pro Asp Lys Val Leu Glu Ile
    1580                1585                1590

Leu Lys Gln Ser Thr Ile Ile Glu Phe Glu Ser Ser Gly Phe Asn
    1595                1600                1605

Lys Thr Ile Lys Glu Met Leu Gly Met Lys Leu Ala Gly Ile Tyr
    1610                1615                1620

Asn Glu Thr Ser Asn Asn
    1625

<210> SEQ ID NO 16
<211> LENGTH: 1056
<212> TYPE: PRT
<213> ORGANISM: Artificial Sequence
<220> FEATURE:
<223> OTHER INFORMATION: Pasteurella multocida Cas9

<400> SEQUENCE: 16

Met Gln Thr Thr Asn Leu Ser Tyr Ile Leu Gly Leu Asp Leu Gly
1               5                   10                  15

Ala Ser Val Gly Trp Ala Val Val Glu Ile Asn Glu Asn Glu Asp Pro
            20                  25                  30

Ile Gly Leu Ile Asp Val Gly Val Arg Ile Phe Glu Arg Ala Glu Val
        35                  40                  45

Pro Lys Thr Gly Glu Ser Leu Ala Leu Ser Arg Arg Leu Ala Arg Ser
    50                  55                  60

Thr Arg Arg Leu Ile Arg Arg Ala His Arg Leu Leu Leu Ala Lys
65                  70                  75                  80

Arg Phe Leu Lys Arg Glu Gly Ile Leu Ser Thr Ile Asp Leu Glu Lys
                85                  90                  95

Gly Leu Pro Asn Gln Ala Trp Glu Leu Arg Val Ala Gly Leu Glu Arg
            100                 105                 110

Arg Leu Ser Ala Ile Glu Trp Gly Ala Val Leu Leu His Leu Ile Lys
        115                 120                 125

His Arg Gly Tyr Leu Ser Lys Arg Lys Asn Glu Ser Gln Thr Asn Asn
    130                 135                 140

Lys Glu Leu Gly Ala Leu Leu Ser Gly Val Ala Gln Asn His Gln Leu
145                 150                 155                 160

Leu Gln Ser Asp Asp Tyr Arg Thr Pro Ala Glu Leu Ala Leu Lys Lys
                165                 170                 175
```

```
Phe Ala Lys Glu Glu Gly His Ile Arg Asn Gln Arg Gly Ala Tyr Thr
                180                 185                 190
His Thr Phe Asn Arg Leu Asp Leu Leu Ala Glu Leu Asn Leu Leu Phe
            195                 200                 205
Ala Gln Gln His Gln Phe Gly Asn Pro His Cys Lys Glu His Ile Gln
        210                 215                 220
Gln Tyr Met Thr Glu Leu Leu Met Trp Gln Lys Pro Ala Leu Ser Gly
225                 230                 235                 240
Glu Ala Ile Leu Lys Met Leu Gly Lys Cys Thr His Glu Lys Asn Glu
                245                 250                 255
Phe Lys Ala Ala Lys His Thr Tyr Ser Ala Glu Arg Phe Val Trp Leu
            260                 265                 270
Thr Lys Leu Asn Asn Leu Arg Ile Leu Glu Asp Gly Ala Glu Arg Ala
        275                 280                 285
Leu Asn Glu Glu Glu Arg Gln Leu Leu Ile Asn His Pro Tyr Glu Lys
290                 295                 300
Ser Lys Leu Thr Tyr Ala Gln Val Arg Lys Leu Leu Gly Leu Ser Glu
305                 310                 315                 320
Gln Ala Ile Phe Lys His Leu Arg Tyr Ser Lys Glu Asn Ala Glu Ser
                325                 330                 335
Ala Thr Phe Met Glu Leu Lys Ala Trp His Ala Ile Arg Lys Ala Leu
            340                 345                 350
Glu Asn Gln Gly Leu Lys Asp Thr Trp Gln Asp Leu Ala Lys Lys Pro
        355                 360                 365
Asp Leu Leu Asp Glu Ile Gly Thr Ala Phe Ser Leu Tyr Lys Thr Asp
370                 375                 380
Glu Asp Ile Gln Gln Tyr Leu Thr Asn Lys Val Pro Asn Ser Val Ile
385                 390                 395                 400
Asn Ala Leu Leu Val Ser Leu Asn Phe Asp Lys Phe Ile Glu Leu Ser
                405                 410                 415
Leu Lys Ser Leu Arg Lys Ile Leu Pro Leu Met Glu Gln Gly Lys Arg
            420                 425                 430
Tyr Asp Gln Ala Cys Arg Glu Ile Tyr Gly His His Tyr Gly Glu Ala
        435                 440                 445
Asn Gln Lys Thr Ser Gln Leu Leu Pro Ala Ile Pro Ala Gln Glu Ile
450                 455                 460
Arg Asn Pro Val Val Leu Arg Thr Leu Ser Gln Ala Arg Lys Val Ile
465                 470                 475                 480
Asn Ala Ile Ile Arg Gln Tyr Gly Ser Pro Ala Arg Val His Ile Glu
                485                 490                 495
Thr Gly Arg Glu Leu Gly Lys Ser Phe Lys Glu Arg Arg Glu Ile Gln
            500                 505                 510
Lys Gln Gln Glu Asp Asn Arg Thr Lys Arg Glu Ser Ala Val Gln Lys
        515                 520                 525
Phe Lys Glu Leu Phe Ser Asp Phe Ser Ser Glu Pro Lys Ser Lys Asp
530                 535                 540
Ile Leu Lys Phe Arg Leu Tyr Glu Gln Gln His Gly Lys Cys Leu Tyr
545                 550                 555                 560
Ser Gly Lys Glu Ile Asn Ile His Arg Leu Asn Glu Lys Gly Tyr Val
                565                 570                 575
Glu Ile Asp His Ala Leu Pro Phe Ser Arg Thr Trp Asp Asp Ser Phe
            580                 585                 590
```

-continued

Asn Asn Lys Val Leu Val Leu Ala Ser Glu Asn Gln Asn Lys Gly Asn
            595                 600                 605

Gln Thr Pro Tyr Glu Trp Leu Gln Gly Lys Ile Asn Ser Glu Arg Trp
610                 615                 620

Lys Asn Phe Val Ala Leu Val Leu Gly Ser Gln Cys Ser Ala Ala Lys
625                 630                 635                 640

Lys Gln Arg Leu Leu Thr Gln Val Ile Asp Asp Asn Lys Phe Ile Asp
            645                 650                 655

Arg Asn Leu Asn Asp Thr Arg Tyr Ile Ala Arg Phe Leu Ser Asn Tyr
            660                 665                 670

Ile Gln Glu Asn Leu Leu Val Gly Lys Asn Lys Lys Asn Val Phe
            675                 680                 685

Thr Pro Asn Gly Gln Ile Thr Ala Leu Leu Arg Ser Arg Trp Gly Leu
            690                 695                 700

Ile Lys Ala Arg Glu Asn Asn Arg His His Ala Leu Asp Ala Ile
705                 710                 715                 720

Val Val Ala Cys Ala Thr Pro Ser Met Gln Gln Lys Ile Thr Arg Phe
                    725                 730                 735

Ile Arg Phe Lys Glu Val His Pro Tyr Lys Ile Glu Asn Arg Tyr Glu
            740                 745                 750

Met Val Asp Gln Glu Ser Gly Glu Ile Ile Ser Pro His Phe Pro Glu
            755                 760                 765

Pro Trp Ala Tyr Phe Arg Gln Glu Val Asn Ile Arg Val Phe Asp Asn
            770                 775                 780

His Pro Asp Thr Val Leu Lys Glu Met Leu Pro Asp Arg Pro Gln Ala
785                 790                 795                 800

Asn His Gln Phe Val Gln Pro Leu Phe Val Ser Arg Ala Pro Thr Arg
                    805                 810                 815

Lys Met Ser Gly Gln Gly His Met Glu Thr Ile Lys Ser Ala Lys Arg
                    820                 825                 830

Leu Ala Glu Gly Ile Ser Val Leu Arg Ile Pro Leu Thr Gln Leu Lys
            835                 840                 845

Pro Asn Leu Leu Glu Asn Met Val Asn Lys Glu Arg Glu Pro Ala Leu
            850                 855                 860

Tyr Ala Gly Leu Lys Ala Arg Leu Ala Glu Phe Asn Gln Asp Pro Ala
865                 870                 875                 880

Lys Ala Phe Ala Thr Pro Phe Tyr Lys Gln Gly Gly Gln Gln Val Lys
                    885                 890                 895

Ala Ile Arg Val Glu Gln Val Gln Lys Ser Gly Val Leu Val Arg Glu
            900                 905                 910

Asn Asn Gly Val Ala Asp Asn Ala Ser Ile Val Arg Thr Asp Val Phe
            915                 920                 925

Ile Lys Asn Asn Lys Phe Phe Leu Val Pro Ile Tyr Thr Trp Gln Val
            930                 935                 940

Ala Lys Gly Ile Leu Pro Asn Lys Ala Ile Val Ala His Lys Asn Glu
945                 950                 955                 960

Asp Glu Trp Glu Glu Met Asp Glu Gly Ala Lys Phe Lys Phe Ser Leu
                    965                 970                 975

Phe Pro Asn Asp Leu Val Glu Leu Lys Thr Lys Lys Glu Tyr Phe Phe
            980                 985                 990

Gly Tyr Tyr Ile Gly Leu Asp Arg Ala Thr Gly Asn Ile Ser Leu Lys
            995                 1000                1005

```
Glu His Asp Gly Glu Ile Ser Lys Gly Lys Asp Gly Val Tyr Arg
    1010                1015                1020

Val Gly Val Lys Leu Ala Leu Ser Phe Glu Lys Tyr Gln Val Asp
    1025                1030                1035

Glu Leu Gly Lys Asn Arg Gln Ile Cys Arg Pro Gln Gln Arg Gln
    1040                1045                1050

Pro Val Arg
    1055

<210> SEQ ID NO 17
<211> LENGTH: 99
<212> TYPE: RNA
<213> ORGANISM: Artificial Sequence
<220> FEATURE:
<223> OTHER INFORMATION: sgRNA: gAd3A TS1

<400> SEQUENCE: 17
guccucgagc aaaaggugcc guuuuagagc uagaaauagc aaguuaaaau aaggcuaguc      60
cguuaucaac uugaaaaagu ggcaccgagu cgguggugc                           99

<210> SEQ ID NO 18
<211> LENGTH: 99
<212> TYPE: RNA
<213> ORGANISM: Artificial Sequence
<220> FEATURE:
<223> OTHER INFORMATION: sgRNA: gTrGA TS2

<400> SEQUENCE: 18
guucagugca auaggcgucu guuuuagagc uagaaauagc aaguuaaaau aaggcuaguc      60
cguuaucaac uugaaaaagu ggcaccgagu cgguggugc                           99

<210> SEQ ID NO 19
<211> LENGTH: 99
<212> TYPE: RNA
<213> ORGANISM: Artificial Sequence
<220> FEATURE:
<223> OTHER INFORMATION: sgRNA:gTrGA TS11

<400> SEQUENCE: 19
gccaauggcg acggcagcac guuuuagagc uagaaauagc aaguuaaaau aaggcuaguc      60
cguuaucaac uugaaaaagu ggcaccgagu cgguggugc                           99

<210> SEQ ID NO 20
<211> LENGTH: 99
<212> TYPE: RNA
<213> ORGANISM: Artificial Sequence
<220> FEATURE:
<223> OTHER INFORMATION: sgRNA: gPyr2 TS6

<400> SEQUENCE: 20
gcacagcggg augcccuugu guuuuagagc uagaaauagc aaguuaaaau aaggcuaguc      60
cguuaucaac uugaaaaagu ggcaccgagu cgguggugc                           99
```